(12) United States Patent
Araldi et al.

(10) Patent No.: US 7,276,531 B2
(45) Date of Patent: Oct. 2, 2007

(54) G-LACTAM DERIVATIVES AS PROSTAGLANDIN AGONISTS

(75) Inventors: Gian Luca Araldi, Smithtown, NY (US); Srinivasa Karra, Pembroke, MA (US); Zhong Zhao, Wayland, MA (US); Nadia Brugger, Boston, MA (US)

(73) Assignee: Applied Research Systems ARS Holding N.V., Curacao (AN)

( * ) Notice: Subject to any disclaimer, the term of this patent is extended or adjusted under 35 U.S.C. 154(b) by 79 days.

(21) Appl. No.: 10/547,676

(22) PCT Filed: Mar. 2, 2004

(86) PCT No.: PCT/EP2004/050239

§ 371 (c)(1),
(2), (4) Date: Sep. 2, 2005

(87) PCT Pub. No.: WO2004/078103

PCT Pub. Date: Sep. 16, 2004

(65) Prior Publication Data

US 2006/0194865 A1    Aug. 31, 2006

Related U.S. Application Data

(60) Provisional application No. 60/451,829, filed on Mar. 3, 2003.

(51) Int. Cl.
*A61K 31/4015* (2006.01)
*C07D 405/06* (2006.01)
*C07D 401/06* (2006.01)
*C07D 409/06* (2006.01)
*C07D 207/08* (2006.01)

(52) U.S. Cl. .................... 514/422; 514/424; 548/517; 548/518; 548/527; 548/543

(58) Field of Classification Search ............... 548/517, 548/543, 527, 518; 514/422, 424
See application file for complete search history.

(56) References Cited

U.S. PATENT DOCUMENTS

| | | |
|---|---|---|
| 6,235,780 B1 | 5/2001 | Ohuchida et al. |
| 2001/0056060 A1 | 12/2001 | Cameron et al. |
| 2002/0004495 A1 | 1/2002 | Harada et al. |

FOREIGN PATENT DOCUMENTS

| | | |
|---|---|---|
| EP | 1 114 816 | 7/2001 |
| WO | 88/07537 | 10/1988 |
| WO | 99/02164 | 1/1999 |
| WO | 99/33794 | 7/1999 |
| WO | 00/03980 | 1/2000 |
| WO | 01/46140 | 6/2001 |
| WO | 02/24647 | 3/2002 |
| WO | 02/42268 | 5/2002 |
| WO | 03/007941 | 1/2003 |
| WO | 03/008377 | 1/2003 |

OTHER PUBLICATIONS

Sato et al, Tetrahedron Letters, 1997, 38(22), pp. 3931-3934.*
Katz et al, Prostaglandins—Basic and Clinical Considerations, May 1974, Anesthesiology, vol. 40, No. 5, pp. 471-475.*
Buckley et al, Immunde Deficiency Foundation Diagnostic and Clinical Care Guidelines, article retrieved from Internet on Mar. 1, 2007,<< http://www.primaryimmune.org/pubs/book_diag/IDF%20Diagnostic%20and%20Clinical%20Care%20Guidelines%20-%20Final.pdf>>.*
Andersson et al, The pharmacological treatment of urinary incontinence, BJU International, 1999, vol. 84, pp. 923-947.*
Abramovitz et al. "The utilization of recombinant prostanoid receptors to determine the affinities and selectivities of prostaglandins and related analogs", Biochimica et Biophysica Acta, vol. 1483, pp. 285-293 2000.
Benoit et al. "Latest discoveries in prostaglandin receptor modulators", Expert Opin. Ther. Patents, vol. 12, No. 8, pp. 1225-1235 2002.
Choung et al. "Role of EP2 Receptors and cAMP in Prostaglandin E2 Regulated Expression of Type I Collagen alpha1, Lysyl Oxidase, and Cyclooxygenase-1 Genes in Human Embryo Lung Fibroblasts", Journal of Cellular Biochemistry, vol. 71, pp. 254-263 1998.
Coleman et al. "Prostanoids and their Receptors", In Comprehensive Medicinal Chemistry, The rational Design, Mechanistic Study and Therapeutic Application of Chemical Compounds, vol. 3, pp. 643-714 1989.
Coleman et al. "VIII. International Union of Pharmacology Classification of Prostanoid Receptors: Properties, Distribution, and Structure of the Receptors and Their Subtypes", Pharmacological Reviews, vol. 46, No. 2, pp. 205-229 1994.
Fleisch et al. "LY171883, 1-<2-Hydroxy-3-Propyl-4-<4-(1H-Tetrazol-5-yl)Butoxy>Phenyl>Ethanone, an Orally Active Leukotriene D4 Antagonist", The Journal of Pharmacology and Experimental Therapeutics, vol. 233, No. 1, pp. 148-157 1985.
Guth et al. "Topical Aspirin Plus HCI Gastric Lesions in the Rat", Gastroenterology, vol. 76, No. 1, pp. 88-93 1979.

(Continued)

*Primary Examiner*—Rebecca Anderson
*Assistant Examiner*—Karen Cheng
(74) *Attorney, Agent, or Firm*—Oblon, Spivak, McClelland, Maier & Neustadt, P.C.

(57) ABSTRACT

A gamma-lactam diene of Formula I:

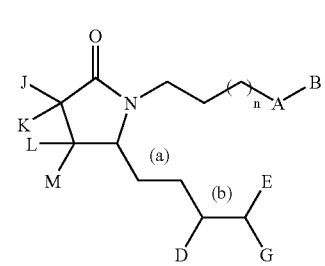

which is particularly useful as a medicament for the treatment of various disorders such as asthma, hypertension, osteoporosis, sexual dysfunction and fertility disorders.

31 Claims, No Drawings

OTHER PUBLICATIONS

Hundertmark et al. "Pd(PhCN)2Cl2/P(t-Bu)3: A Versatile Catalyst for Sonogashira Reactions of Aryl Bromides at Room Temperature", Organic Letters, vol. 2, No. 12, pp. 1729-1731 2000.

Langlois et al. "Intramolecular Mitsunobu reaction in the regio- and stereoselective synthesis of cis-4,5-disubstituted piperidin-2-ones", Tetrahedron Letters, vol. 41, pp. 8285-8288, 2000.

Levi et al. "Regulation of prostanoid synthesis in microglial cells and effects of prostaglandin E2 on microglial functions", Biochimie, vol. 80. pp. 899-904 1998.

Miyaura. "Nippon Yakurigaku Zasshi", Folia Pharmacol. Jpn., vol. 117, pp. 293-297, with English abstract 2001.

Nair et al. "Folate Analogues. 31. Synthesis of the Reduced Derivatives of 11-Deazahomofolic Acid, 10-Methyl-11-deazahomofolic Acid, and Their Evaluation as Inhibitors of Glycinamide Ribonucleotide Formyltransferase", J. Med Chem., vol. 32, pp. 1277-1283 1989.

Negishi et al. "A Selective Synthesis of (E)-2-Methyl-1-alkenyl Iodides via Zirconium-Catalyzed Carboalumination", Synthesis, pp. 501, 502, 1035, 1979.

Shen et al. "The Stille Reaction of 1,1-Dibromo-1-alkenes; Preparation of Trisubstituted Alkenes and Internal Alkynes", J. Org. Chem., vol. 64, pp. 8873-8879 1999.

Baldwin et al. "(L)-Pyroglutamic Acid as a Chiral Starting Material For Asymmetric Synthesis", Tetrahedron Letters, vol. 32, No. 10, pp. 1379-1380 1991.

Uenishi et al. "Stereoselective Hydrogenolysis of 1,1-Dibromo-1-alkenes and Stereospecific Synthesis of Conjugated (Z)-Alkenyl Compounds", J. Org. Chem., vol. 63, pp. 8965-8975 1998.

Ushikubi et al. "Roles of Prostanoids Revealed from Studies Using Mice Lacking Specific Prostanoid Receptors", Jpn. J. Pharmacol., vol. 83, pp. 279-285 2000.

Watanabe et al. "Total Synthesis of (±)-Dihydropinidine, (±)-Monomorine I, and (±)-Indolizidine 223AB (Gephyrotoxin 223AB) by Intramolecular Nitroso Diels-Alder Reaction", J. Org. Chem., vol. 54, pp. 4088-4097 1989.

* cited by examiner

G-LACTAM DERIVATIVES AS PROSTAGLANDIN AGONISTS

FIELD OF THE INVENTION

The present invention is directed to γ-lactam derivatives, in particular for use as medicaments, as well as pharmaceutical formulations containing such γ-lactam derivatives. Said γ-lactam derivatives are useful in the treatment and/or prevention of asthma, hypertension, osteoporosis, sexual dysfunction and fertility disorders. Preferably, the γ-lactam derivatives display a modulatory, notably an agonist activity on the prostaglandin receptors, particularly prostaglandin E receptors. More preferably, said compounds are useful in the treatment and/or prevention of disease states mediated by prostaglandin EP2 and/or EP4 receptors, including asthma, fertility, osteoporosis, inflammation, gastric ulcers and sexual disorders.

BACKGROUND OF THE INVENTION

Prostaglandins (PGs) which belong to the prostanoids family are known to have diverse biological activities such as contraction and relaxation of smooth muscle, inhibition and enhancement of neurotransmitter release, inflammation, including pain and bone metabolism (Coleman et al. 1989; EP1114816).

In particular, Prostaglandin E2 (PGE2) which is the naturally-occurring agonist of EP receptor, was found to have various roles in ovulation and fertilization, in the control of blood pressure, febrile responses, regulation of bicarbonate secretion induced by acid-stimulation in the duodenum, bone resorption, smooth muscle contraction regulation, TNF down-regulation and inhibition of microglial IL-12 secretion (Ushikibi et al., 2000; Miyaura. et al., 2001, *Nippon Yakurigaku Zasshi*, 117(4): 293-7; Benoit et al., 2002 and Levi et al., 1998 *Biochimie* 80(11):899-904)

The EP receptor has been further classified into four different receptor subtypes: EP1, EP2, EP3, and EP4 (Coleman et al. 1994).

Knock-out mice lacking each sub-type of the EP receptor gave evidence of the different roles played by these receptors (Ushikubi et al., 2000) in various mechanisms such as ovulation (EP2), blood pressure control (EP2), closure of ductus arteriosus (EP4) and bone resorption (EP4) (Miyaura et al., 2001).

As prostaglandin E2 (PGE2) is a natural ligand for all sub-types of the EP receptor, selective effects on one of the sub-types of the EP receptor is impossible to achieve with the endogenous prostaglandins.

Several prostanoid receptors and modulators of those receptors have been reported with different range of selectivity for the various receptor sub-types (Coleman et al. 1994, Abramowitz et al., 2000, and Benoit et al., 2002).

Recently, EP2 agonists have been developed (U.S. Pat. No. 6,235,780 and WO 9933794). The combination of an EP2 agonists in combination of an EP4 agonist has been developed for osteoporosis treatment (US 20010056060). EP4 selective agonists have been developed for the treatment of bone disorders (WO 0242268 and WO 0146140), erectile dysfunction (WO 9902164) and other prostaglandin related disorders (WO 0224647, US 20020004495, WO 0003980, WO 03007941 and WO 03008377). EP2 and EP4 antagonists have been also reported (Benoit et al., 2002).

SUMMARY OF THE INVENTION

It is an object of the present invention to provide substances which are suitable for the treatment and/or prevention of disorders related to prostaglandins.

It is also an object of the present invention to provide substances which are suitable for the treatment and/or prevention of infertility, including ovulatory disorders.

It is also an object of the present invention to provide substances which are suitable for the treatment and/or prevention asthma.

It is also an object of the present invention to provide substances which are suitable for the treatment and/or prevention of sexual dysfunction such as erectile dysfunction.

It is also an object of the present invention to provide substances which are suitable for the treatment and/or prevention of preterm labor and dysmenorrhea.

It is also an object of the present invention to provide substances which are suitable for the treatment and/or prevention of gastric ulceration.

It is also an object of the present invention to provide substances which are suitable for the treatment and/or prevention of inflammatory disorders.

It is also an object of the present invention to provide substances which are suitable for the treatment and/or prevention of respiratory disorders.

It is notably an object of the present invention to provide chemical compounds which are able to up-regulate, including to agonize, the function of EP receptors, especially EP2 and/or EP4 receptors in disease states in mammals, especially in humans.

It is also an object of the present invention to provide small molecule chemical compounds for the modulation, preferably the agonization of the prostaglandin EP receptors, especially EP2 and/or EP4 receptors.

Moreover, it is an object of the present invention to provide methods for preparing said small molecule chemical compounds. It is furthermore an object of the present invention to provide a new category of pharmaceutical formulations for the treatment of infertility, ovulatory disorders, respiratory disorders such as asthma, emphysema and COPD (Chronic Obstructive Pulmonary Disease), gastric ulceration, inflammation, including Inflammatory Bowel Syndrome (IBS), preterm labor and dysmenorrhea, and/or diseases mediated by the EP receptors, especially EP2 and/or EP4 receptors.

It is finally an object of the present invention to provide a method for the treatment and/or prevention of disorders mediated by the EP receptors, like pre-term labor with EP agonists.

In a first aspect, the invention provides gamma-lactam dienes derivatives of Formula I:

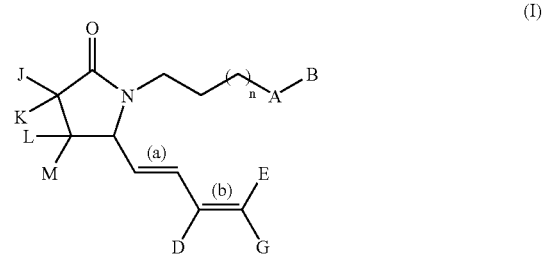

wherein A is selected from the group comprising or consisting of optionally substituted $C_1$-$C_4$ alkyl, optionally substituted aryl, optionally substituted heteroaryl, optionally substituted $C_3$-$C_6$ cycloalkyl and optionally substituted $C_3$-$C_6$ heterocycloalkyl;

B is C(O)Z wherein Z is selected from the group comprising or consisting of hydroxy, optionally substituted alkoxy, optionally substituted $C_1$-$C_6$ alkyl optionally substituted $C_1$-$C_6$ heteroalkyl and $NR^1R^2$ wherein $R^1$ and $R^2$ are independently selected from the group comprising or consisting of H, optionally substituted $C_3$-$C_6$ cycloalkyl, optionally substituted $C_3$-$C_6$ heterocycloalkyl, optionally substituted aryl $C_1$-$C_6$ alkyl and optionally substituted heteroaryl $C_1$-$C_6$ alkyl;

D is selected from the group comprising or consisting of H, halogen and optionally substituted $C_1$-$C_6$ alkyl;

E is selected from the group comprising or consisting of H and optionally substituted $C_1$-$C_6$ alkyl;

G is selected from the group comprising or consisting of H, optionally substituted $C_1$-$C_6$ alkyl, optionally substituted $C_2$-$C_6$ alkenyl, optionally substituted $C_2$-$C_6$ alkynyl, optionally substituted $C_3$-$C_6$ cycloalkyl $C_1$-$C_6$ alkyl, optionally substituted $C_3$-$C_6$ cycloalkyl, optionally substituted $C_3$-$C_6$ heterocycloalkyl, optionally substituted aryl $C_1$-$C_6$ alkyl, optionally substituted heteroaryl $C_1$-$C_6$ alkyl, optionally substituted aryl and optionally substituted heteroaryl; or E and G form, together with the carbon atom they are attached to, an optionally substituted $C_3$-$C_6$ cycloalkyl ring;

J, K and L are independently selected from the group consisting or comprising H, halogen, optionally substituted $C_1$-$C_6$ alkyl, optionally substituted aryl and optionally substituted heteroaryl;

M is selected from OH and H;

n is an integer selected from 0 and 1;

(a) and (b) double bonds can be independently Z (or "cis") or E (or "trans") bonds.

In a second aspect of the invention, the invention provides gamma-lactam dienes derivatives of Formula II:

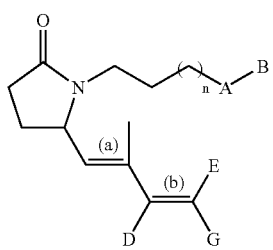

(II)

wherein A, B, D, E, G, (a), (b) and n are as defined above.

In a third aspect, the present invention provides gamma-lactam diene derivatives of Formulae I or II for use as a medicament.

In a fourth aspect, the invention provides a compound of Formula I, for the preparation of a pharmaceutical composition useful for a variety of therapies, including alleviating, preventing and/or treating pre-term labor, ovulation induction, cervical ripening, dysmenorrhea, respiratory disorders such as asthma, emphysema and COPD (Chronic Obstructive Pulmonary Disease), hypertension, infertility or fertility disorder, undesired blood clotting, preeclampsia or eclampsia, an eosinophil disorder, sexual dysfunction, osteoporosis and other destructive bone disease or disorder, renal dysfunction (acute and chronic), immune deficiency disorder or disease, dry eye, skin disorders such as ichthyosis, elevated intra-ocular pressure such as associated with glaucoma, sleep disorders, ulcers, including gastric ulcers, ulcerative colitis, inflammation, including Inflammatory Bowel Disease (IBD), Crohn's disease, joint inflammation and pulmonary inflammation and other diseases and disorders associated with the prostaglandin family of compounds and receptors thereof.

In a fifth aspect, the invention provides a compound according to Formulae I or II for the modulation of the functions of EP receptors, specifically EP2 and/or EP4.

In a sixth aspect, the invention provides a method for treating a patient suffering from pre-term labor, ovulation induction, cervical ripening, dysmenorrhea, respiratory disorders such as asthma, emphysema and COPD (Chronic Obstructive Pulmonary Disease), hypertension, infertility or fertility disorder, undesired blood clotting, preeclampsia or eclampsia, an eosinophil disorder, sexual dysfunction, osteoporosis and other destructive bone disease or disorder, renal dysfunction (acute and chronic), immune deficiency disorder or disease, inflammation, including Inflammatory Bowel Disease (IBD), Crohn's disease, joint inflammation and pulmonary inflammation, dry eye, skin disorders such as ichthyosis, elevated intra-ocular pressure such as associated with glaucoma, sleep disorders, ulcers, including gastric ulcers, ulcerative colitis. The method comprising administering a compound according to Formulae I or II.

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"$C_1$-$C_6$-heteroalkyl" refers to a $C_1$-$C_6$-alkyl group wherein at least one carbon atom is replaced by a heteroatom selected from from the group consisting of O, S, NR, R being defined as hydrogen or methyl.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"aryl $C_1$-$C_6$-alkyl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, thiophenyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro] benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"heteroaryl $C_1$-$C_6$-alkyl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH═$CH_2$), n-2-propenyl (allyl, —$CH_2$CH═$CH_2$) and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"cycloalkyl $C_1$-$C_6$-alkyl" refers to $C_1$-$C_6$-alkyl groups having a cycloalkyl substituent, including cyclohexylmethyl, cyclopentylpropyl, and the like.

"heterocycloalkyl $C_1$-$C_6$-alkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"Halogen" refers to fluoro, chloro, bromo and iodo atoms.

"Substituted" refers to groups substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "aminosulfonyl", "ammonium", "acyl amino", "amino carbonyl", "aryl", "heteroaryl", "sulfinyl", "sulfonyl", "alkoxy", "alkoxy carbonyl", "carbamate", "sulfanyl", "halogen", trihalomethyl, cyano, hydroxy, mercapto, nitro, and the like.

"Pharmaceutically acceptable salts or complexes" refers to salts or complexes of the below-specified compounds of Formula (I). Examples of such salts include, but are not restricted, to base addition salts formed by reaction of compounds of Formula (I) with is organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-etanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein.

The term "Enantiomeric excess" (ee) refers to the percent excess of the enantiomer over the racemate in a mixture of a pure enantiomer (R or S) and a racemate (RS) as defined below.

$$ee=100\%\times(|R-S|)/(R+S)=|\% R-\% S|$$

where R represents the number of moles of R enantiomer in the sample and S represents the number of moles of S enantiomer in the sample, and |R−S| represents the Absolute Value of the difference of R and S. Compounds of the invention can be obtained in an "Enantiomeric excess" by a synthesis comprising an enantioselective step or can be isolated by for example, crystallization or chiral HPLC.

A particularly preferred embodiment includes compounds of the invention in an enantiomeric excess of the R enantiomer, of at least at or about 50, 70, 80 or 90%, with degree of preference increasing with the increasing ee of the R enantiomer.

In the absence of an enantiomeric synthesis, racemic products are usually obtained that do however also have the inventive set out activity as EP2 and/or EP4 agonists.

A particularly preferred embodiment includes compounds of the invention wherein bond (a) is preferably in a "Z" conformation.

Another preferred embodiment includes compounds of the invention wherein bond (a) is preferably in an "E" conformation.

The term "preterm labor" or the term "premature labor" shall mean expulsion from the uterus of an infant before the normal end of gestation, or more particularly, onset of labor with effacement and dilation of the cervix before the $37^{th}$ week of gestation. It may or may not be associated with vaginal bleeding or rupture of the membranes.

The term "dysmenorrhea" shall mean painful menstruation.

The term "caesarean delivery" shall mean incision through the abdominal and uterine walls for delivery of a foetus.

The term "fertility condition(s)" also refers to a condition, particularly infertility, of a female mammal, especially a female patient. This condition includes conditions where ovulation triggering is needed. Examples of female patients in such a condition are female undergoing a treatment for ovulation induction or an Assisted Reproduction Therapy (ART).

The term "ovulation induction" (OI), refers to the stimulation of release of an oocyte (occasionally two or three oocytes) into the fallopian tubes of a female patient, for in vivo fertilisation. OI is used in anovulatory patients [for example, WHO group I patients (hypogonadotrophic hypogonadism) and WHO group II anovulation (hypothalamic-pituitary dysfunction resulting in arrested or attenuated gonadal function), including patients suffering from polycystic ovarian syndrome (PCOS)]. It is usually desired to stimulate the release of a single oocyte, in order to avoid the risks associated with multiple pregnancies. In a typical ovulation induction regimen, the patient is administered Follicular Stimulating Hormone (FSH), an analogue of FSH or a molecule stimulating endogenous FSH production to stimulate follicular growth for several days until at least one follicle is observed (by ultrasound) with a mean diameter of approximately 17 mm or greater. At this stage, an ovulation trigger (hCG) is given to stimulate rupture of the follicle and release of an oocyte into the fallopian tube ("ovulation triggering").

The term "Assisted Reproductive Technology" (ART) includes for example, in vitro fertilisation (IVF), and intra-cytoplasmic sperm injection (ICSI). Oocytes are harvested from mature follicles immediately before rupture, and graded before being fertilized in vitro by combination with sperm.

The resulting embryos are graded for quality, and usually 2 to 3 are selected for placement in the uterus (remaining embryos can be cryopreserved for future attempts). Because of the many factors involved in establishing an ongoing pregnancy, many patients must have oocytes placed in the uterus multiple times before success is achieved. Because of this, in contrast to OI regimens, for ART it is desired to harvest multiple oocytes, in order to maximise the chances of successful pregnancy. The controlled development of multiple pre-ovulatory follicles by administration of exogenous agents capable of inducing follicular growth (such as FSH) is called controlled ovarian hyperstimulation (COH). When there are at least 3 follicles with a mean diameter greater than 16 mm, ovulation is triggered (hCG bolus). Oocytes are usually recovered from pre-ovulatory follicles, by aspiration.

The present invention also includes the geometrical isomers, the optically active forms, enantiomers, diastereomers of compounds according to Formula I, mixtures of these, racemates and also pharmaceutically acceptable salts.

The compounds according to the present invention are those of Formula I.

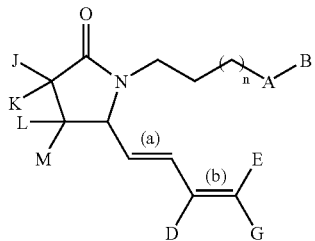

(I)

wherein A is selected from the group comprising or consisting of optionally substituted $C_1$-$C_4$ alkyl, optionally substituted aryl, optionally substituted hetoroaryl, optionally substituted $C_3$-$C_6$ cycloalkyl and optionally substituted $C_3$-$C_6$ heterocycloalkyl;

B is C(O)Z wherein Z is selected from the group comprising or consisting of hydroxy, optionally substituted alkoxy, optionally substituted $C_1$-$C_6$ alkyl, optionally substituted $C_1$-$C_6$ heteroalkyl and $NR^1R^2$ wherein $R^1$ and $R^2$ are independently selected from the group comprising or consisting of H, optionally substituted $C_3$-$C_6$ cycloalkyl, optionally substituted $C_3$-$C_6$ heterocycloalkyl, optionally substituted aryl $C_1$-$C_6$ alkyl and optionally substituted heteroaryl $C_1$-$C_6$ alkyl;

D is selected from the group comprising or consisting of H, halogen and optionally substituted $C_1$-$C_6$ alkyl;

E is selected from the group comprising or consisting of H and optionally substituted $C_1$-$C_6$ alkyl;

G is selected from the group comprising or consisting of H, optionally substituted $C_1$-$C_6$ alkyl, optionally substituted $C_2$-$C_6$ alkenyl, optionally substituted $C_2$-$C_6$ alkynyl, optionally substituted $C_3$-$C_6$ cycloalkyl $C_1$-$C_6$ alkyl, optionally substituted $C_3$-$C_6$ cycloalkyl, optionally substituted $C_3$-$C_6$ heterocycloalkyl, optionally substituted aryl $C_1$-$C_6$ alkyl, optionally substituted heteroaryl $C_1$-$C_6$ alkyl, optionally substituted aryl and optionally substituted heteroaryl; or E and G form, together with the carbon atom they are attached to, an optionally substituted $C_3$-$C_6$ cycloalkyl ring;

J, K and L are independently selected from the group consisting or comprising H, optionally substituted $C_1$-$C_6$ alkyl, optionally substituted aryl and optionally substituted heteroaryl;

J, K and L are independently selected from the group consisting or comprising H, halogen, optionally substituted $C_1$-$C_6$ alkyl, optionally substituted aryl and optionally substituted heteroaryl;

M is selected from OH and H;

n is an integer selected from 0 and 1;

(a) and (b) double bonds can be independently Z or E bonds.

Preferred compounds of the invention are those according to Formula II:

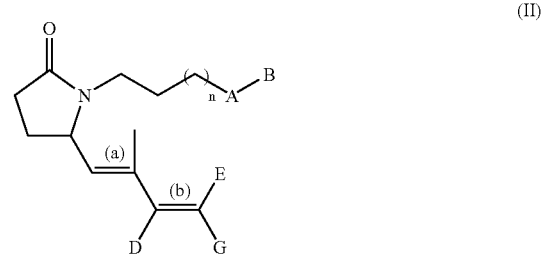

(II)

wherein A, B, D, E, G, (a), (b) and n are as defined above.

In one embodiment, the invention provides gamma-lactam derivatives of Formulae (I) or (II) wherein A is selected from the group comprising or consisting of optionally substituted aryl, including phenyl and optionally substituted heteroaryl, including thiophenyl, furanyl and pyridine.

In another specific embodiment, the invention provides gamma-lactam derivatives of Formulae (I) or (II) wherein Z is selected from the group comprising or consisting of hydroxy and optionally substituted $C_1$-$C_6$ alkyl, more preferably OH.

In another specific embodiment, the invention provides gamma-lactam derivatives of Formulae (I) or (II) wherein Z is selected from the group comprising or consisting of hydroxy and optionally substituted alkoxy, more preferably OH.

In one embodiment, the invention provides gamma-lactam derivatives of Formulae (I) or (II) wherein bond (a) is in the "Z" conformation.

In another embodiment, the invention provides gamma-lactam derivatives of Formulae (I) or (II) wherein bond (a) is in the "E" conformation.

In a further embodiment, the invention provides gamma-lactam derivatives of Formulae (I) or (II) wherein bond (a) is in the "E" conformation and D is selected from optionally substituted $C_1$-$C_6$ alkyl, including methyl and halogen, including Fluorine.

In another specific embodiment, the invention provides gamma-lactam derivatives of Formulae (I) or (II) wherein D is selected from H and optionally substituted $C_1$-$C_6$ alkyl, including methyl.

In a further specific embodiment, the invention provides gamma-lactam derivatives of Formulae (I) or (II) wherein D is H.

In another further specific embodiment, the invention provides gamma-lactam derivatives of Formulae (I) or (II) wherein D is methyl.

In another specific embodiment, the invention provides gamma-lactam derivatives of Formulae (I) or (II) wherein D is halogen, including Fluorine.

In another specific embodiment, the invention provides gamma-lactam derivatives of Formulae (I) or (II) wherein E is selected from the group comprising or consisting of H and optionally substituted $C_1$-$C_6$ alkyl, including methyl and trifluoro-ethyl.

In another specific embodiment, the invention provides gamma-lactam derivatives of Formulae (I) or (II) wherein G is selected from the group comprising or consisting of optionally substituted $C_1$-$C_6$ alkyl, including ethyl, butyl, propyl, isopropyl, dimethyl propyl, methyl propyl, optionally substituted $C_2$-$C_6$ alkenyl, including dimethyl propenyl, optionally substituted $C_2$-$C_6$ alkynyl and optionally substituted $C_3$-$C_6$ cycloalkyl $C_1$-$C_6$ alkyl, including cyclopropyl ethyl and cylcopropyl methyl.

In another specific embodiment, the invention provides gamma-lactam derivatives of Formulae (I) or (II) wherein G is selected from the group comprising or consisting of optionally substituted $C_3$-$C_6$ cycloalkyl, including cyclopropyl, optionally substituted $C_3$-$C_6$ heterocycloalkyl, optionally substituted aryl $C_1$-$C_6$ alkyl, optionally substituted heteroaryl $C_1$-$C_6$ alkyl, optionally substituted aryl, including phenyl and optionally substituted heteroaryl.

In another specific embodiment, the invention provides gamma-lactam derivatives of Formulae (I) or (II) wherein E and G form, together with the carbon atom they are attached to, an optionally substituted $C_3$-$C_6$ cycloalkyl ring, including cyclohexyl.

A particularly preferred embodiment of the present invention is a gamma lactam diene derivative according to Formula II wherein A is selected from optionally substituted aryl, including phenyl and optionally substituted heteroaryl, including thiophenyl, B is COOH and D is H.

Another preferred embodiment of the present invention is a gamma lactam diene derivative according to Formula II wherein A is optionally substituted aryl, including phenyl and optionally substituted heteroaryl, including thiophenyl, B is COOH, D is H, E is selected from the group comprising or consisting H or $C_1$-$C_6$ alkyl, preferably H or methyl.

Another preferred embodiment of the present invention is a gamma lactam diene derivative according to Formula II wherein A is optionally substituted aryl, including phenyl or optionally substituted heteroaryl, including thiophenyl, B is COOH, D is H, E is selected from the group comprising or consisting H or $C_1$-$C_6$ alkyl, preferably H or methyl, G is selected from the group comprising or consisting of H and optionally substituted $C_1$-$C_6$ alkyl, including methyl, propyl, butyl and 2-methyl pent-2-enyl.

A particularly preferred embodiment of the present invention is a gamma lactam diene derivative according to Formula II wherein A is selected from optionally substituted phenyl, optionally substituted thiophenyl and optionally substituted furanyl, B is COOH.

A particularly preferred embodiment of the present invention is a gamma lactam diene derivative according to Formula II wherein A is selected from optionally substituted phenyl, optionally substituted thiophenyl, B is COOH, G is selected from the group comprising or consisting of optionally substituted $C_1$-$C_6$ alkyl, optionally substituted $C_2$-$C_6$ alkenyl, optionally substituted $C_2$-$C_6$ alkynyl and optionally substituted $C_3$-$C_6$ cycloalkyl $C_1$-$C_6$ alkyl.

A particularly preferred embodiment of the present invention is a gamma lactam diene derivative according to Formula II wherein A is selected from optionally substituted phenyl, optionally substituted thiophenyl, B is COOH, G is selected from the group comprising or consisting of optionally substituted $C_3$-$C_6$ cycloalkyl, optionally substituted $C_3$-$C_6$ heterocycloalkyl, optionally substituted aryl $C_1$-$C_6$ alkyl, optionally substituted heteroaryl $C_1$-$C_6$ alkyl, optionally substituted aryl and optionally substituted heteroaryl.

A particularly preferred embodiment of the present invention is a gamma lactam diene derivative according to Formula II wherein A is selected from optionally substituted phenyl, optionally substituted thiophenyl, B is COOH, E and G form, together with the carbon atom they are attached to, an optionally substituted $C_3$-$C_6$ cycloalkyl ring, including cyclohexyl.

According to another preferred embodiment of the invention, a gamma lactam diene of the invention is selected from the group consisting of:

4-(2-{(2R)-2-[(1Z,3E)-octa-1,3-dienyl]-5-oxopyrrolidin-1-yl}ethyl)benzoic acid;

4-(2-{(2R)-2-[(1E,3E)-octa-1,3-dienyl]-5-oxopyrrolidin-1-yl}ethyl)benzoic acid;

4-(2-{(2R)-2-[(1Z,3E)-4-methylocta-1,3-dienyl]-5-oxopyrrolidin-1-yl}ethyl)benzoic acid;

4-(2-{(2R)-2-[(1E,3E)-4-methylocta-1,3-dienyl]-5-oxopyrrolidin-1-yl}ethyl)benzoic acid;

4-(2-{(2R)-2-[(1Z)-4-methylpenta-1,3-dienyl]-5-oxopyrrolidin-1-yl}ethyl)benzoic acid;

4-(2-{(2R)-2-[(1E)-4-methylpenta-1,3-dienyl]-5-oxopyrrolidin-1-yl}ethyl)benzoic acid;

4-(2-{(2R)-2-[(1Z,3E)-hexa-1,3-dienyl]-5-oxopyrrolidin-1-yl}ethyl)benzoic acid;

4-(2-{(2R)-2-[(1E,3E)-hexa-1,3-dienyl]-5-oxopyrrolidin-1-yl}ethyl)benzoic acid;

4-(2-{(2R)-2-[(1Z,3E)-hepta-1,3-dienyl]-5-oxopyrrolidin-1-yl}ethyl)benzoic acid;

4-(2-{(2R)-2-[(1E,3E)-hepta-1,3-dienyl]-5-oxopyrrolidin-1-yl}ethyl)benzoic acid;

4-(2-{(2R)-2-[(1Z,3E)-4,8-dimethylnona-1,3,7-trienyl]-5-oxopyrrolidin-1-yl}ethyl)benzoic acid;

4-(2-{(2R)-2-[(1E,3E)-4,8-dimethylnona-1,3,7-trienyl]-5-oxopyrrolidin-1-yl}ethyl)benzoic acid;

5-(3-{(2R)-2-[(1Z,3E)-4-methylocta-1,3-dienyl]-5-oxopyrrolidin-1-yl}propyl)thiophene-2-carboxylic acid;

5-(3-{(2R)-2-[(1E,3E)-4-methylocta-1,3-dienyl]-5-oxopyrrolidin-1-yl}propyl)thiophene-2-carboxylic acid;

4-(2-{(2R)-2-[(1Z,3Z)-hepta-1,3-dienyl]-5-oxopyrrolidin-1-yl}ethyl)benzoic acid;

4-(2-{(2R)-2-[(1Z and 1E,3Z)-hexa-1,3-dienyl]-5-oxopyrrolidin-1-yl}ethyl)benzoic acid;

5-(3-{(2R)-2-[(1Z,3E)-octa-1,3-dienyl]-5-oxopyrrolidin-1-yl}propyl)thiophene-2-carboxylic acid;

5-(3-{(2R)-2-[(1E,3E)-octa-1,3-dienyl]-5-oxopyrrolidin-1-yl}propyl)thiophene-2-carboxylic acid;

5-(3-{(2R)-2-[(1Z,3E)-octa-1,3-dienyl]-5-oxopyrrolidin-1-yl}propyl)thiophene-2-carboxylic acid;

5-(3-{(2R)-2-[(1E,3E)-3-methylocta-1,3-dienyl]-5-oxopyrrolidin-1-yl}propyl)thiophene-2-carboxylic acid;

4-(2-{(2R)-2-[(1Z,3E)-3-methylocta-1,3-dienyl]-5-oxopyrrolidin-1-yl}ethyl)benzoic acid;

4-(2-{(2R)-2-[(1E,3E)-3-methylocta-1,3-dienyl]-5-oxopyrrolidin-1-yl}ethyl)benzoic acid;
5-(3-{(2R)-2-[(1E,3E)-3-methylocta-1,3-dienyl]-5-oxopyrrolidin-1-yl}propyl)thiophene-2-carboxylic acid;
5-(3-{(2R)-2-[(1Z,3E)-3-methylocta-1,3-dienyl]-5-oxopyrrolidin-1-yl}propyl)-2-furoic acid;
5-(3-{(2R)-2-[(1E,3E)-3-methylocta-1,3-dienyl]-5-oxopyrrolidin-1-yl}propyl)-2-furoic acid;
4-(2-{(2R)-2-[(1Z,3E)-6-cyclopropyl-4-methylhexa-1,3-dienyl]-5-oxopyrrolidin-1-yl}ethyl)benzoic acid;
4-(2-{(2R)-2-[(1E,3E)-6-cyclopropyl-4-methylhexa-1,3-dienyl]-5-oxopyrrolidin-1-yl}ethyl)benzoic acid;
4-(2-{(2R)-2-[(1Z,3E-4,7-dimethylocta-1,3-dienyl]-5-oxopyrrolidin-1-yl}ethyl)benzoic acid;
4-(2-{(2R)-2-[(1E,3E)-4,7-dimethylocta-1,3-dienyl]-5-oxopyrrolidin-1-yl}ethyl)benzoic acid;
4-(2-{(2R)-2-[(1Z,3E)-5-cyclopentyl-4-methylpenta-1,3-dienyl]-5-oxopyrrolidin-1-yl}ethyl)benzoic acid;
4-(2-{(2R)-2-[(1E,3E)-5-cyclopentyl-4-methylpenta-1,3-dienyl]-5-oxopyrrolidin-1-yl}ethyl)benzoic acid;
4-(2-{(2R)-2-[(1Z,3E)-4-phenylpenta-1,3-dienyl]-5-oxopyrrolidin-1-yl}ethyl)benzoic acid;
4-(2-{(2R)-2-[(1E,3E)-4-phenylpenta-1,3-dienyl]-5-oxopyrrolidin-1-yl}ethyl)benzoic acid;
4-(2-{(2R)-2-[(1Z,3Z)-4-phenylpenta-1,3-dienyl]-5-oxopyrrolidin-1-yl}ethyl)benzoic acid;
4-(2-{(2R)-2-[(1E,3Z)-4-phenylpenta-1,3-dienyl]-5-oxopyrrolidin-1-yl}ethyl)benzoic acid;
5-(3-{(2R)-2-[(1Z,3E)-octa-1,3-dienyl]-5-oxopyrrolidin-1-yl}propyl)-2-furoic acid;
5-(3-{(2R)-2-[(1E,3E)-octa-1,3-dienyl]-5-oxopyrrolidin-1-yl}propyl)-2-furoic acid;
4-(3-{(2R)-2-[(1Z,3E)-octa-1,3-dienyl]-5-oxopyrrolidin-1-yl}propyl)benzoic acid;
4-(3-{(2R-2-[(1E,3E)-octa-1,3-dienyl]-5-oxopyrrolidin-1-yl}propyl)benzoic acid;
4-(2-{(2R)-2-[(1Z,3Z)-3-fluoro-4-methylocta-1,3-dienyl]-5-oxopyrrolidin-1-yl}ethyl)benzoic acid;
4-(2-{(2R)-2-[(1E,3Z)-3-fluoro-4-methylocta-1,3-dienyl]-5-oxopyrrolidin-1-yl}ethyl)benzoic acid;
4-(2-{(2R)-2-[(1Z,3E)-3-fluoro-4-methylocta-1,3-dienyl]-5-oxopyrrolidin-1-yl}ethyl)benzoic acid;
4-(2-{(2R)-2-[(1E,3E)-3-fluoro-4-methylocta-1,3-dienyl]-5-oxopyrrolidin-1-yl}ethyl)benzoic acid;
4-(2-{(2R)-2-[(1Z,3E)-4-methylhepta-1,3-dienyl]-5-oxopyrrolidin-1-yl}ethyl)benzoic acid;
4-(2-{(2R)-2-[(1E,3E)-4-methylhepta-1,3-dienyl]-5-oxopyrrolidin-1-yl}ethyl)benzoic acid;
4-(2-{(2R)-2-[(1Z,3E)-4-methylhexa-1,3-dienyl]-5-oxopyrrolidin-1-yl}ethyl)benzoic acid;
4-(2-{(2R)-2-[(1E,3E)-4-methylhexa-1,3-dienyl]-5-oxopyrrolidin-1-yl}ethyl)benzoic acid,
6-(3-{(2R)-2-[(1Z,3E)-4-methylocta-1,3-dienyl]-5-oxopyrrolidin-1-yl}propyl)pyridine-2-carboxylic acid;
6-(3-{(2R)-2-[(1Z,3E)-4-methylocta-1,3-dienyl]-5-oxopyrrolidin-1-yl}propyl)pyridine-2-carboxylic acid;
4-(2-{(2R)-2-[(1E,3E)-4,6-dimethylhepta-1,3-dienyl]-5-oxopyrrolidin-1-yl}ethyl)benzoic acid;
4-(2-{(2R)-2-[(1E,3E)-4,6-dimethylhepta-1,3-dienyl]-5-oxopyrrolidin-1-yl}ethyl)benzoic acid;
4-(2-{(2R)-2-[(1Z,3E)-4,7,7-trimethylocta-1,3-dienyl]-5-oxopyrrolidin-1-yl}ethyl)benzoic acid;
4-(2-{(2R)-2-[(1E,3E)-4,7,7-trimethylocta-1,3-dienyl]-5-oxopyrrolidin-1-yl}ethyl)benzoic acid;
4-(2-{(2R)-2-[(1Z,3E)-4,5-dimethylhexa-1,3-dienyl]-5-oxopyrrolidin-1-yl}ethyl)benzoic acid;
4-(2-{(2R)-2-[(1E,3E)-4,5-dimethylhexa-1,3-dienyl]-5-oxopyrrolidin-1-yl}ethyl)benzoic acid;
4-(2-{(2R)-2-[(1Z,3E)-4-cyclohexylbuta-1,3-dienyl]-5-oxopyrrolidin-1-yl}ethyl)benzoic acid;
4-(2-{(2R)-2-[(1E,3E)-4-cyclohexylbuta-1,3-dienyl]-5-oxopyrrolidin-1-yl}ethyl)benzoic acid;
4-(2-{(2R)-2-[(1Z,3E)-4-phenyl-4-triflurobuta-1,3-dienyl]-5-oxopyrrolidin-1-yl}ethyl)benzoic acid;
4-(2-{(2R)-2-[(1E,3E)-4-phenyl-4-triflurobuta-1,3-dienyl]-5-oxopyrrolidin-1-yl}ethyl)benzoic acid;
4-(2-{(2R)-2-[(1Z,3Z)-4-phenyl-4-triflurobuta-1,3-dienyl]-5-oxopyrrolidin-1-yl}ethyl)benzoic acid;
4-(2-{(2R)-2-[(1E,3Z)-4-phenyl-4-triflurobuta-1,3-dienyl]-5-oxopyrrolidin-1-yl}ethyl)benzoic acid;
4-(2-{(2R)-2-[(1Z,3E)-4-cyclopropylpenta-1,3-dienyl]-5-oxopyrrolidin-1-yl}ethyl)benzoic acid;
4-(2-{(2R)-2-[(1E,3E)-4-cyclopropylpenta-1,3-dienyl]-5-oxopyrrolidin-1-yl}ethyl)benzoic acid;
5-(3-{(2R)-2-[(1Z,3E)-4-methylocta-1,3-dienyl]-5-oxopyrrolidin-1-yl}propyl)nicotinic acid;
5-(3-{(2R)-2-[(1E,3E)-4-methylocta-1,3-dienyl]-5-oxopyrrolidin-1-yl}propyl)nicotinic acid.

Another preferred embodiment of the invention provides compounds according to Formula II for use as a medicament.

Another preferred embodiment of the invention provides a use of compounds according to Formula II for the preparation of a pharmaceutical composition for the treatment and/or the prevention of a disease selected from pre-term labor, ovulation induction, cervical ripening, dysmenorrhea, respiratory disorders such as asthma, emphysema and COPD (Chronic Obstructive Pulmonary Disease), hypertension, infertility or fertility disorder, undesired blood clotting, preeclampsia or eclampsia, an eosinophil disorder, sexual dysfunction, osteoporosis and other destructive bone disease or disorder, renal dysfunction (acute and chronic), immune deficiency disorder or disease, inflammation, including colon inflammation, inflammatory Bowel Disease (DD), Crohn's disease, joint inflammation and pulmonary inflammation, dry eye, skin disorders such as ichthyosis, elevated intra-ocular pressure such as associated with glaucoma, sleep disorders, ulcers, including gastric ulcers and ulcerative colitis.

Another preferred embodiment of the invention provides a method for treating a patient suffering from pre-term labor, ovulation induction, cervical ripening, dysmenorrhea, respiratory disorders such as asthma, emphysema and COPD (Chronic Obstructive Pulmonary Disease), hypertension, infertility or fertility disorder, undesired blood clotting, preeclampsia or eclampsia, an eosinophil disorder, sexual dysfunction, osteoporosis and other destructive bone disease or disorder, renal dysfunction (acute and chronic), immune deficiency disorder or disease, inflammation, including colon inflammation, Inflammatory Bowel Disease (IBD), Crohn's disease, joint inflammation and pulmonary inflammation, dry eye, skin disorders such as ichthyosis, elevated intra-ocular pressure such as associated with glaucoma, sleep disorders, ulcers, including gastric ulcers, ulcerative colitis. The method comprising administering a compound according to Formula II.

Compounds of Formulae I or II may be used for the treatment of a disease.

Specifically, the compounds of Formulae I or II are suitable for use in treating disorders such as infertility, premature birth, dysmenorrhea, and for stopping labor prior to cesarean delivery.

The compounds of the present invention are in particular useful for the treatment of ovulatory disorders, preterm labor, premature birth and dysmenorrhea.

The compounds of the present invention are further useful for the treatment of respiratory diseases such as asthma, emphysema and Chronic Obstructive Pulmonary Disorders (COPD).

The compounds of the present invention are further useful for the treatment of inflammatory disorders such as colon inflammation, Inflammatory Bowel Disease (IBD), pulmonary inflammation and joint inflammation.

The compounds of the present invention are further useful for the treatment of erectile dysfunction, glaucoma, hypertension, gastric ulcers, renal dysfunction, osteoporosis and other destructive bone disease or disorder and immune deficiency disorders.

Preferably, the compounds according to Formulae I or II alone or in a form of a pharmaceutical composition are suitable for the modulation of EP function(s), thus specifically allowing the treatment and/or prevention of disorders which are mediated by the EP receptors. Such modulation preferably involves the agonisation of EP function(s), notably by the agonisation of the EP2 and/or EP4 receptors in mammals, and in particular in humans.

The compounds of the invention may be employed alone or in combination with further pharmaceutical agents, e.g. with a further EP modulator or any other substance used such as FSH, Luteining Hormone (LH), mixtures of these and human Chorionic Gonadotrophin (hCG), during the ovulation induction or ART therapies.

When employed as pharmaceuticals, the gamma lactam derivatives of the present invention are typically administered in the form of a pharmaceutical composition. Hence, pharmaceutical compositions comprising a compound of Formula I and a pharmaceutically acceptable carrier, diluent or excipient are also within the scope of the present invention. A person skilled in the art is aware of a whole variety of such carriers, diluents or excipients suitable to formulate a pharmaceutical composition.

The compounds of the invention, together with a conventionally employed adjuvant, carrier, diluent or excipient may be formulated as pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the gamma lactam derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "bait dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the gamma lactam diene compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dio-xide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the gamma lactam derivatives of Formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences,* 20$^{th}$ Edition, 2000, Marck Publishing Company, Easton, Pa.

The compounds of this invention can also be administered in sustained release forms or from sustained release drug delivery systems. A description of representative sustained release materials can also be found in *Remington's Pharmaceutical Sciences,* 20$^{th}$ Edition, 2000, Marck Publishing Company, Easton, Pa.

Still a further object of the present invention is a process for preparing gamma lactam derivatives according to Formula I.

The gamma lactam derivatives exemplified in this invention may be prepared from readily available or previously described starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

Synthesis of Compounds of the Invention

The novel gamma lactam diene derivatives can be prepared from readily available starting materials Examples of synthetic pathways for compounds of Formula I will be described below.

The following abbreviations refer respectively to the definitions below:

eq (equivalent), hr (hour), i.p. (interperitoneal), i.v. (intravenous), mg (milligram), mmol (millimole), mm (millimeter), mM (millimolar), mL (milliliter), p.o. (per os), rt (room temperature), ACN (Acetonitrile), ART (Assisted Reproduction Therapy), BSA (Bovine Serum Albumin), CAN (Cerium Ammonium Nitrate), CMC (Carboxymethyl Cellulose), COH (Ovarian Hyperstimulation), COPD (Chronic Obstructive Pulmonary Disease), DCM (Dichloromethane), DIBALH (Diisobutylaluminum Hydride), DMSO (Dimethylsulfoxide), EtOAc (Ethyl acetate), FBS (Foetal Bovine Serum), FSH (Follicule Stimulating Hormone), hCG (human Chorionic Gonadotrophin), HR (Heart Rate), IBSD (Inflammatory Bowel Disease), ICSI (Intracytoplasmic Sperm Injection), IT (Intratracheal), IVF (In vitro Fertilization), LH (Luteining Hormone), NP3S (5% N-methyl-pyrrolidinone/30% PEG400/25% PEG200/20% Propylene glycol in saline), OI (Ovulation Induction), PBS (Phosphate Buffer Saline), PCOS (Polycystic Ovarian Syndrome), PGE2 (prostaglandin E2), PEG (Polyethylene glycol), PMSG (Pregnant mare's serum gonadotropin), TFA (Trifluoro-acetic acid), THF (Tetrahydrofuran), THP (Tetrahydropyranyl), TNF (Tumour Necrosis Factor).

In general, compounds of Formulae (I) or (II) are made by Wittig reaction between an aldehyde of formula xxvii and a phosphorane derivative of formula xxvi (Scheme 6 below).

Synthesis of the Intermediates a) Synthesis of Aldehyde Intermediates

Synthesis pathways for an aldehyde intermediate of formula xxvii is described in Schemes 1 to 4.

For example, synthesis of an aldehyde intermediate of formula xxvii wherein n is 0 and A is phenyl, i.e. of formula v, can be achieved according to Scheme 1 below.

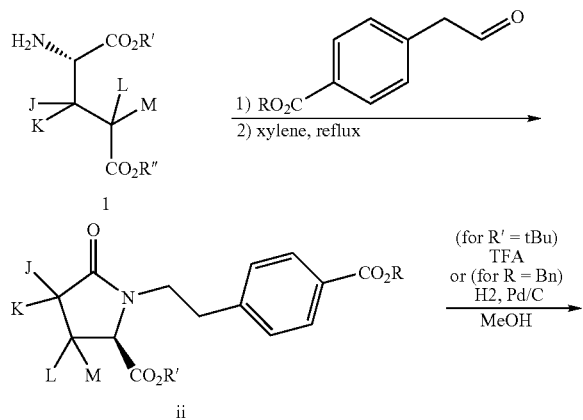

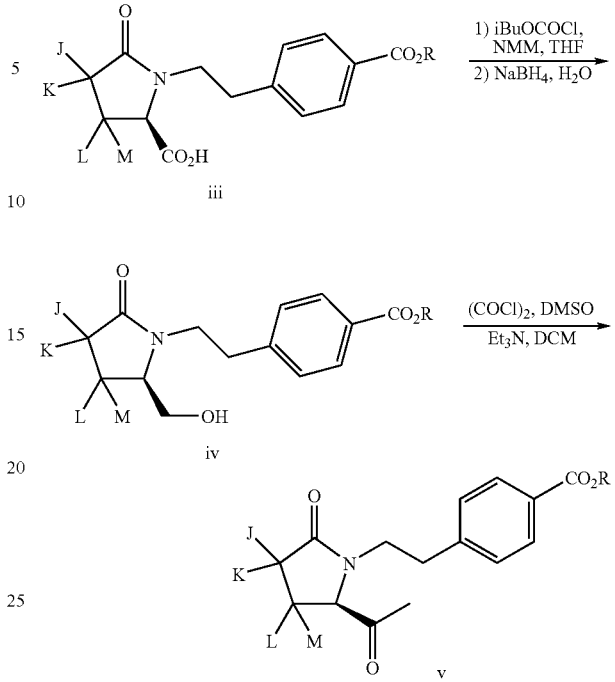

The aldehyde v can be synthesized starting from Glu derivative of formula i. The amino groups can be suitably alkylated e.g. by reductive alkylation reaction using the appropriate aldehyde (e.g. a carboxyphenylacetaldehyde, like 4-carbomethoxyphenyl acetaldehyde) and NaCNBH₃ or other suitable reducing agent. The crude residue is then suitably refluxed in a suitable solvent such as xylene to afford the desired γ-lactam derivative ii. Selective deprotection of the ester group directly attached to the γ-lactam ring can be obtained by acid treatment (when R=tBu is used) or catalytic hydrogenation (when R=Bn is used). Reduction of the acid iii to the corresponding alcohol iv can be accomplished by reduction e.g. with NaBH₄ of the correspondent acyl tert-butyl carbonate intermediate. Swern oxidation of the alcohol intermediate can be accomplished using the Swern protocol or other more suitable oxidation reagents.

Aldehyde intermediate of formula xxvii wherein n is 1, i.e. of formula xi, can be obtained according to Scheme 2 below.

The pyrrolidinone derivative of formula vi could be alkylated using propargyl bromide in the presence of a suitable base like K₂CO₃ and acetone as solvent or other suitable solvents to lead to intermediate viii.

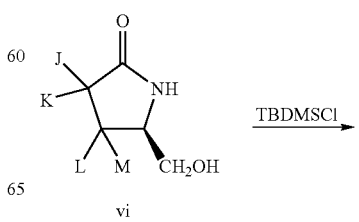

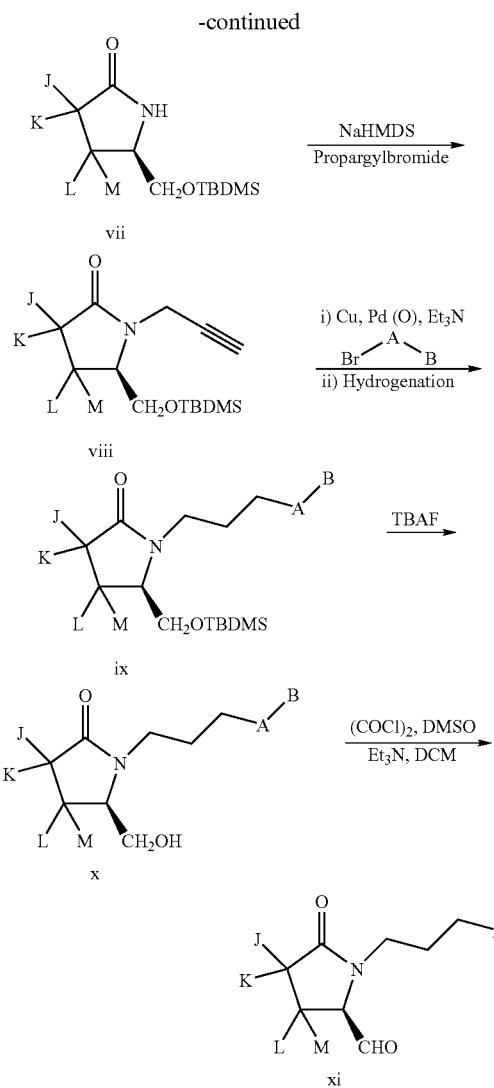

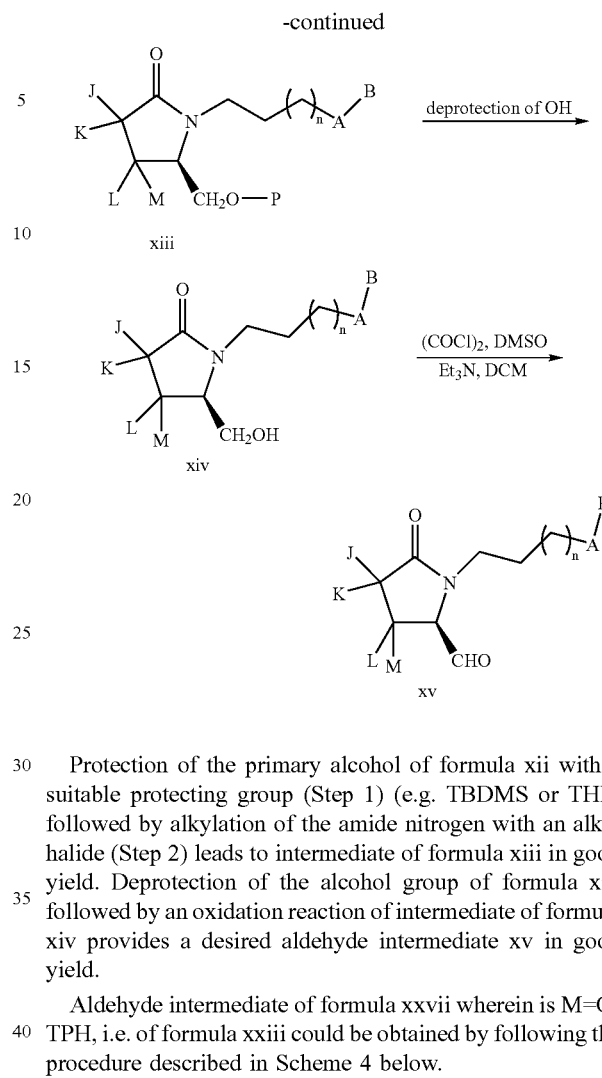

Catalytic addition of a suitable halo-aryl esters or halo-aryl-isoster of formula halogen-A-B to intermediate viii can be accomplished using CuI and Pd (0) (Hundertmark et al., 2000). Deprotection of the primary alcohol of formula ix in presence of tetrabutyl ammonium fluoride or other suitable acid or nucleophilic reagents affords intermediate x. Finally, swern oxidation of the alcohol intermediate of formula x will give the desired aldehyde xi. Alternatively, aldehyde intermediate of formula x can also be synthesized in a general way as described in Scheme 3 below.

Scheme 3

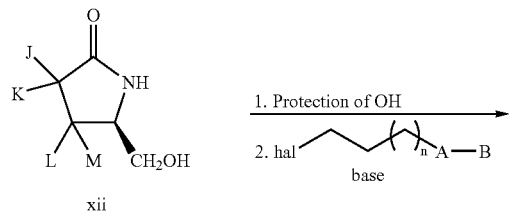

Protection of the primary alcohol of formula xii with a suitable protecting group (Step 1) (e.g. TBDMS or THP) followed by alkylation of the amide nitrogen with an alkyl halide (Step 2) leads to intermediate of formula xiii in good yield. Deprotection of the alcohol group of formula xiii followed by an oxidation reaction of intermediate of formula xiv provides a desired aldehyde intermediate xv in good yield.

Aldehyde intermediate of formula xxvii wherein is M=O-TPH, i.e. of formula xxiii could be obtained by following the procedure described in Scheme 4 below.

Scheme 4

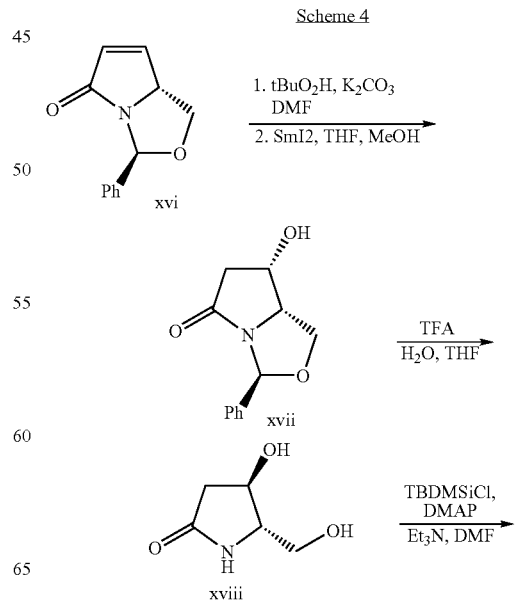

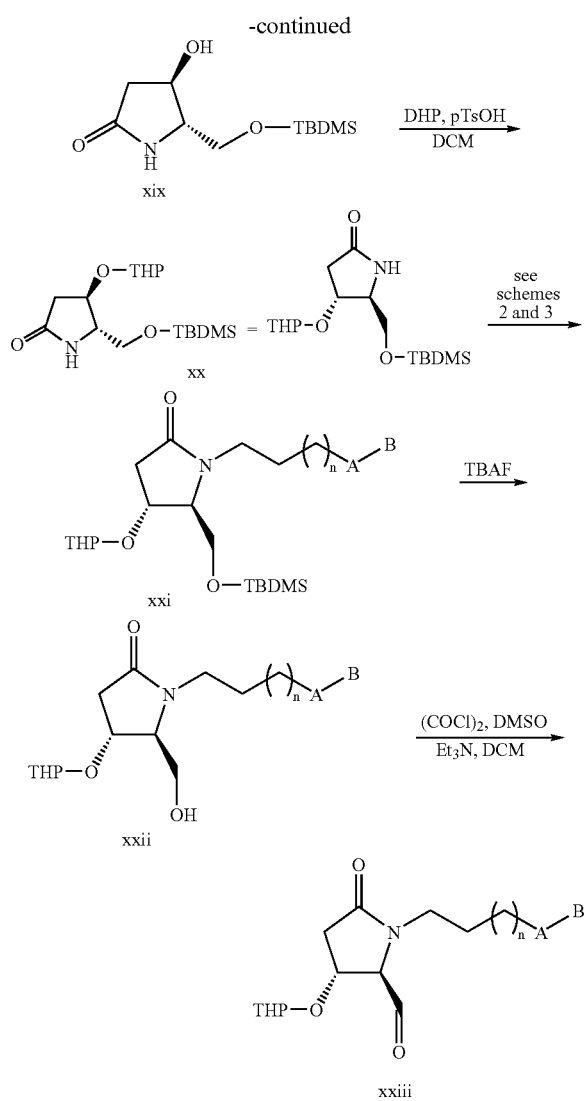

nucleophilic reagents. Finally, oxidation of the alcohol intermediate affords an aldehyde intermediate of formula xxiii.

b) Synthesis of Phosphorane Intermediates

Phosphorane intermediates of formula xxvi can be obtained in 2 steps from an Allyl alcohol of formula xxiv as described in the Scheme 5 below.

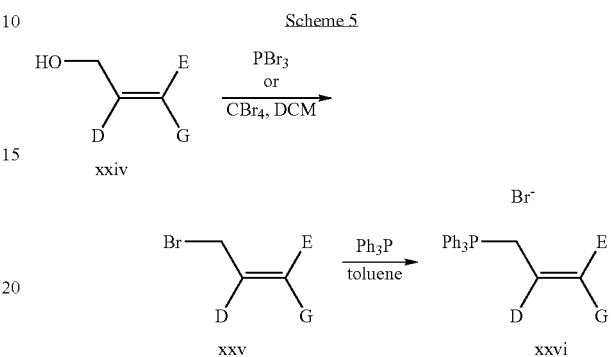

The Allyl alcohol is converted to the corresponding bromide derivatives of formula xxv using PBr₃ or CBr₄ in DCM. Treatment of the bromide intermediate of formula xxv with triphenylphosphine in toluene at reflux afford the desired phosphonate of formula xxvi in good yield.

Synthesis of Compounds of the Invention

A synthetic pathway for compounds of the invention according to Formulae (I) or (II) is described in Scheme 6 below. Wittig reaction between an aldehyde intermediate of formula xxvii and a phosphorane of formula xxvi is obtained using a suitable base (e.g. n-BuLi). Separation of the cis and trans isomers is obtained by flash column chromatography on silica gel. Final deprotection of the optional alcohol followed by saponification of the ester intermediate affords the desired compounds xxx and xxxi.

Diastereospecific epoxidation of a rigid bicyclic α,β-unsaturated lactam of formula xvi (Shimamoto et al., 1991) is carried out in DMF with tert-butylhydroperoxide in the presence of K₂CO₃ followed by regio-specific opening of the epoxide ring with SmI₂ at lower temperature provide the 7-hydroxy-3-phenyltetrahydro-5H-pyrrolo[1,2-c][1,3]oxazol-5-one of formula xvii. (Langlois et al., 2000). This alcohol derivative, xvii, is deprotected to lead the diol of formula xviii under suitable acidic conditions (e.g. TFA in THF). Suitable protection of the primary alcohol is obtained by using TBDMSiCl, DMAP or other suitable catalyst, Et₃N, in DMF or other suitable solvents to lead to intermediate xix.

Protection of the secondary alcohol can be obtained by reaction of the pyrrolidinone derivative xix with DHP, p-TsOH or other suitable acid catalysts to lead to intermediate xx. The pyrrolidinone derivative xx could then be alkylated using the same protocols described in Schemes 2 and 3 above to lead to intermediate xxi.

Selective deprotection of the primary alcohol to afford an alcohol intermediate of formula xxii can be accomplished by using tetrabutyl ammonium fluoride or other suitable acid or

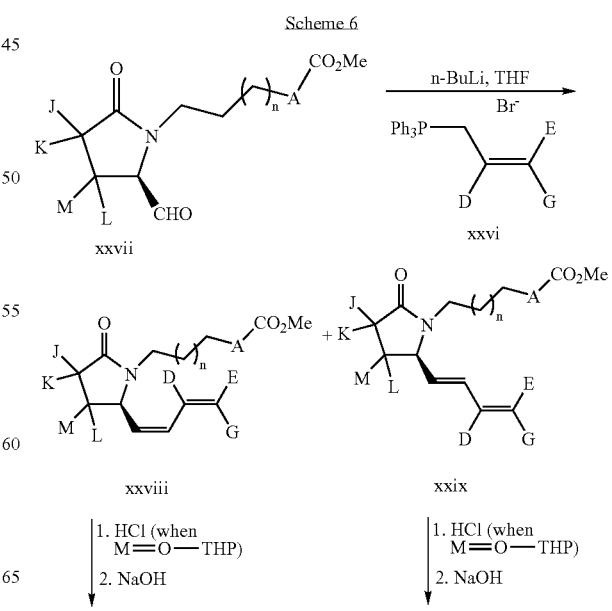

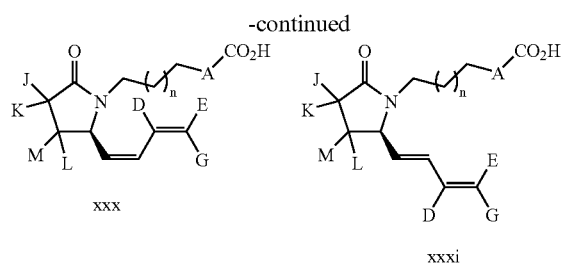

A synthetic pathway for obtaining compounds of the invention according to Formulae (I) or (II), selectively in (Z,E) configuration is shown in Scheme 7 below.

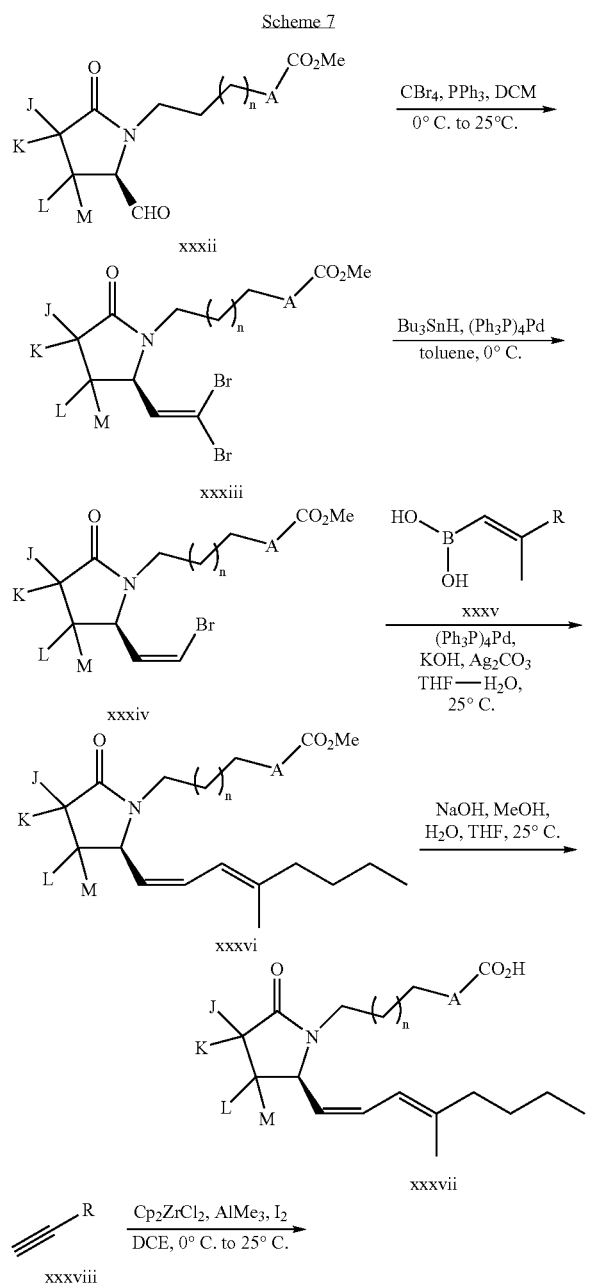

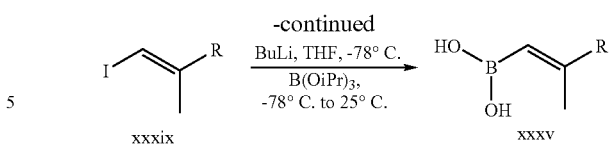

The aldehyde moiety of a compound xxxii can be transformed into dibromo alkene moiety in compound xxxiii using carbontetrabromide and triphenylphosphine (Shen et al., 1999). Selective reduction of trans bromo of compound xxxiii can be achieved with tributyltin hydride and Pd(PPh$_3$)$_4$ to provide (Z)-vinylbromide compound xxxiv (Uenishi et al., 1998). Compound alkyne xxxviii can be subjected to Negishi condition (Negishi et al., 1979) to afford vinyl iodide compound mix, which can be transformed into corresponding boronic acid compound xxxv. Suzuki coupling of compound xxxiv and compound xxxv can selectively afford compound xxxvi, which can undergo saponification to give rise to compound xxxvii.

EXAMPLES

The invention will be illustrated by means of the following examples which are not to be construed as limiting the scope of the invention.

The compounds of the present invention may be synthesized according to the different synthesis pathways provided above. The following examples illustrate preferred methods for synthesizing the compounds according to Formula I, and for determining their biological activities.

Example 1 and 2

Synthesis of 4-(2-{(2R)-2-[(1Z,3E)-octa-1,3-dienyl]-5-oxopyrrolidin-1-yl}ethyl)benzoic acid and 4-(2-{(2R)-2-[(1E,3E)-octa-1,3-dienyl]-5-oxopyrrolidin-1-yl}ethyl)benzoic acid

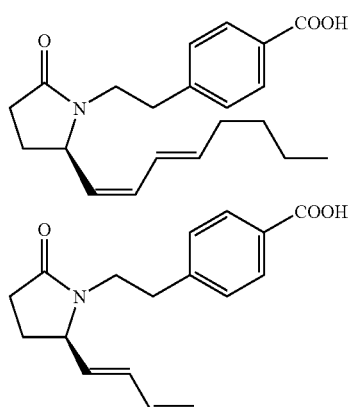

Intermediate 1.1 tert-butyl 1-{2-[4-(methoxycarbonyl)phenyl]ethyl}-5-oxo-D-prolinate (Scheme 1)

To a solution of H-D-Glu(O$^t$Bu)-O$^t$Bu, commercially available from Bache (0.5 g, 2.23 mmol) in MeOH (15 mL)

were added 4-carbomethoxyphenylacetaldehyde (obtained from methyl 4-formyl benzoate as described in Nair et al., 1989) (0.4 g, 2.23 mmol), acetic acid (0.15 mL, 2.67 mmol), and NaCNBH$_3$ (3.3 mL, 1.0 M THF solution, 3.3 mmol). The resulting solution was stirred at RT for 3 h then was diluted with EtOAc (100 mL) and washed with water (50 mL), and brine (50 mL). The organic solution was dried over sodium sulfate and concentrated in vacuo. The crude oil was diluted with xylene and the solution refluxed for 5 h. This solution was concentrated under reduced pressure and purified by silica gel column chromatography using EtOAc/hexane as eluent to afford the title compound (0.75 g, 75%) as a white solid. R$_f$ 0.45 (EtOAc/hexane 1/1); $^1$H NMR (CDCl$_3$) δ 1.47 (s, 9H), 1.95-2.05 (m, 1H), 2.10-2.20 (m, 1H), 2.25-2.35 (m, 1H), 2.40-2.50 (m, 1H), 2.80-3.00 (m, 2H), 3.10-3.20 (m, 1H), 3.82 (dd, 1H), 3.91 (s, 3H), 3.90-4.01 (m, 1H), 7.25 (d, 2H), 7.96 (d, 2H).

Intermediate 1.2

1-{2-[4-(methoxycarbonyl)phenyl]ethyl}-5-oxo-D-proline (Scheme 1)

Intermediate 1.1 (1.6 g, 4.61 mmol) was dissolved in TFA (20 mL) and water (0.1 mL). This solution was stirred at RT for 3 h then concentrated in vacuo to afford the title compound (1.3 g, 98%) as a pale yellow solid used in the next step without further purification. $^1$H NMR (CDCl$_3$) δ 2.10-2.20 (m, 1H), 2.23-2.35 (m, 1H), 2.45-2.65 (m, 2H), 2.85-3.02 (m, 2H), 3.20-3.30 (m, 1H), 3.91 (s, 3H), 3.95-4.05 (m, 2H), 7.25 (d, 2H), 7.97 (d, 2H).

Intermediate 1.3 methyl 4-{2-[(2R)-2-hydroxymethyl)-5-oxopyrrolidin-1-yl]ethyl}benzoate (Scheme 1)

Intermediate 1.2 (4.14 g, 14.2 mmol) was dissolved in THF (50 mL) and cooled to −10° C. The solution was treated with N-methylmorpholine (1.65 mL, 15.1 mmol) and stirred for 5 min. To the solution was added dropwise isobutyl chloroformate (2.00 mL, 15.1 mmol). After the addition was completed, the solution was stirred for 30 min and then filtered through a pad of celite. The collected solution was cooled to −10° C. To the solution was added sodium borohydride (0.81 g, 21.0 mmol) predissolved in water (30 mL). The solution was stirred at 0° C. for 1 h and then at rt for 1 h. The solution was poured into a separatory funnel and diluted with EtOAc (200 mL). The organic layer was washed with 1N HCl solution, saturated NaHCO$_3$ solution, and brine. The organic layer was dried over sodium sulfate, filtered, and concentrated. The residue was purified by column chromatography (EtOAc/hexane) and the alcohol (2.0 g, 50%) was isolated as a white solid. $^1$H NMR (CDCl$_3$) δ 1.80-1.90 (m, 2H), 1.95-2.06 (m, 1H), 2.23-2.35 (m, 1H), 2.40-2.51 (m, 1H), 2.83-3.02 (m, 2H), 3.21-3.35 (m, 1H), 3.45-3.53 (m, 1H), 3.56 (dd, 1H), 3.71 (dd, 1H), 3.82-3.95 (m, 1H), 3.89 (s, 3H), 7.27 (dd, 2H), 7.95 (dd, 2H).

Intermediate 1.4 methyl 4-{2-[(2R)-2-formyl-5-oxopyrrolidin-1-yl]ethyl}benzoate. (Scheme 1)

A DCM solution of oxalyl chloride (2.34 mL, 2.0 M, 4.69 mmol) was diluted with dry DCM (40 mL) and cooled to −70° C. then a solution of DMSO (0.41 mL, 5.78 mmol) in DCM (5 mL) was added dropwise. After 15 min. to this solution was added dropwise a solution of intermediate 1.3 (1.04 g, 3.61 mmol) in DCM (10 mL). The resulting solution was stirred at −78° C. for 45 min. then Et$_3$N (2.5 mL, 18 mmol) was added and the solution warmed to RT. After 15 min. the solution was diluted with DCM (100 mL) and washed with a saturated solution of NH4Cl (2×100 mL), brine (100 mL), dried over sodium sulfate and concentrated in vacuo to afford the aldehyde intermediate (0.99 g, 97%) used in the next step without further purification.

Intermediate 1.5 methyl 4-(2-{(2R)-2-[(1E and 1Z,3E)-octa-1,3-dienyl]-5-oxopyrrolidin-1-yl}ethyl)benzoate and methyl 4-(2-{(2R)-2-[(1E,3E)-octa-1,3-dienyl]-5-oxopyrrolidin-1-yl}ethyl)benzoate (Scheme 6)

To a suspension of (E)-2-heptenyltriphenylphosphonium bromide (obtained from trans-2-hepten-1-ol available from Fluka as described in Watanabe et al., 1989 (880 mg, 2.0 mmol) in dry THF (3 mL) at 0° C. under N$_2$ atmosphere was added potassium t-butoxide (2.0 mL, 1.0M in THF, 2.0 mmol). The resulting blood red colored reaction mixture was stirred for 20 min. and intermediate 1.4 in THF (3 mL) was added at 0° C. The reaction mixture was warmed to rt by removing the cold bath, and stirred for 15 min. and then was quenched with water (10 mL). Extracted with EtOAc (3×25 mL), washed with water (10 mL) and brine (10 mL). The organic phase was dried over sodium sulfate, filtered, and concentrated in vacuo. The residue was purified by silica gel column chromatography (50% EtOAc/hexane) and the product (243 mg, 68%) was isolated as a colorless oil. R$_f$ 0.3 (EtOAc/hexane 3/1).

Examples 1 and 2

To a solution of intermediate 1.5 (80 mg, 0.225 mmol) in MeOH (6 mL) and water (0.2 mL) was added NaOH (20 mg, 0.5 mmol). The resulting solution was heated under microwave oven for 15 min at 80° C. in a sealed tube. Then the reaction mixture was concentrated under reduced pressure. The crude mixture of diastereomers was purified by RP-HPLC using ACN/H$_2$O 0.1% TFA to afford the desired compounds.

Example 1

(First isomer in HPLC: ACN/H$_2$O/TFA, 44 mg): $^1$H NMR (CDCl$_3$): δ 0.90 (two t), 1.2-1.5 (m), 1.58-1.80 (m), 2.0-2.5 (m), 2.70-3.0 (m), 3.04-3.26 (m), 3.58-3.80 (m), 3.94-4.08 (m, 1H), 4.4-4.64 (m) 5.20 (t, J=10.25 Hz) 5.35 (dd, J$_1$=15.01 Hz, J$_2$=9.15 Hz, 1H), 5.51 (dd, J$_1$=15.0 Hz, J$_2$=7.69 Hz, 1H), 5.8 (m), 5.97 (t, J=10.98, 1H), 6.13-6.25 (m), 6.4-6.59 (m) 7.28(two d, 4H), 7.92 (two d, 4H); $^{13}$C NMR (CDCl$_3$): 14.6, 23.5, 26.9, 27.0, 28.2, 28.6, 31.2, 31.3, 32.7, 32.9, 33.0, 33.7, 34.7, 43.2, 56.8, 57.3, 63.1, 122.7, 124.9, 127.5, 127.7, 129.4, 129.9, 130.4, 132.0, 133.6, 134.3, 136.0, 139.1, 145.2, 168.6, 176.5; MS calculated. for C$_{21}$H27NO3: 341; Found (m/z): 342 (m+1).

Example 2

(Second isomer in HPLC:ACN/H$_2$O/TFA, 8 mg): $^1$H NMR (CDCl$_3$): δ 0.91 (t, J=7.32 Hz, 3H), 1.2-1.5 (m, 6H), 1.60-1.78 (m, 1H), 2.0-2.46 (m, 3H), 2.74-3.0 (m, 2H), 3.12-3.38 (m, 1H), 3.56-3.72 (m, 1H), 3.90-4.04 (m, 1H), 5.23 (dd, $J_1$=14.6 Hz, $J_2$=9.1 Hz, 1H), 5.68-5.86 (m, 1H), 6.01 (dd, $J_1$=14.8 Hz, $J_2$=10.2 Hz, 1H), 6.12 (dd, $J_1$=14.8 Hz, $J_2$=10.2 Hz, 1H), 7.28 (d, J=8.0 Hz, 2H), 7.93 (d, J=8.0 Hz, 2H) MS calcd. for $C_{21}H_{27}NO_3$: 341; Found (m/z): 342 (m+1).

Example 3 and 4

Synthesis of 4-(2-{(2R)-2-[(1E,3E)-4-methylocta-1,3-dienyl]-5-oxopyrrolidin-1-yl}ethyl)benzoic acid and 4-(2{(2R)-2-[(1Z,3E)-4-methylocta-1,3-dienyl]-5-oxopyrrolidin-1-yl}ethyl)benzoic acid

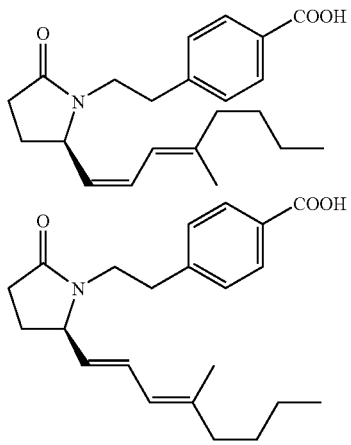

Intermediate 3.1

(E)-3-Methyl-2-heptenyltriphenylphosphonium bromide

To a solution of 3(R,S)-hydroxy-3-methyl-1-heptyl bromide (1.0 g, 6.83 mmol, prepared from commercially available ethyl bromoacetate and 2-hexanone, according to the procedure reported in WO 88/07537, in toluene was added triphenylphosphine (2.35 g, 8.95 mmol). The mixture was refluxed overnight, and the precipitated phosphonium salt was filtered. Washed thoroughly with warm toluene, and dried under vacuum to get the 1.5 g of 3(R,S)-Hydroxy-3-methyl-1-heptyl-triphenylphos-phonium bromide (1.5 g, 55%). $^1$H NMR (Acetone-$D_6$): δ 0.80 (t, J=7.3 Hz, 3H), 1.09-1.33 (m, 6H), 1.40 (d, J=2.9 Hz, 3H), 1.9-2.0 (m, 2H), 4.71 (dd, $J_1$=15.7 Hz, $J_2$=7.69 Hz, 2H), 5.21-5.3 (m, 1H) 7.75-8.10 (m, 15H)

Intermediates 3.2

Methyl 4-(2-{(2R)-2-[(1Z,3E)-4-methylocta1,3-dienyl]-5-oxopyrrolidin-1-yl}ethyl)benzoate and methyl 4-(2-{(2R)-2-[(1E,3E)-4-methylocta1,3-dienyl]-5-oxopyrrolidin-1-yl}ethyl)benzoate (Scheme 6)

To a suspension of intermediate 3.1 (1.2 g, 2.72 mmol) in dry THF (15 mL) at −78° C. under $N_2$ atmosphere was added n-BuLi (3.64 mL, 1.6M in hexane, 5.82 mmol). The resulting red colored reaction mixture was stirred for 20 min. and the aldehyde (500 mg, 1.82 mmol) in THF (3 mL) was added at 0° C. The reaction mixture was warmed to room temperature by removing the cold bath, and stirred for 30 min. The reaction was quenched with water (10 mL). Extracted with EtOAc (3×50 mL), washed with water (10 mL) and brine (10 mL). The organic phase was dried over sodium sulfate, filtered, and concentrated in vacuo. The residue was purified by column chromatography (1:9 EtOAc/hexane) to obtain the E:Z mixture of dienes (510 mg, 76%).

Methyl 4-(2-{(2R)-2-[(1Z,3E)-4-methylocta-1,3-dienyl]-5-oxopyrrolidin-1-yl}ethyl)benzoate $^1$H NMR (CDCl$_3$): δ 0.89 (t, J=7.32 Hz, 3H), 1.2-1.5 (m, 6H), 1.60-1.8 (m, 1H), 1.76 (s, 3H), 2.0-2.25 (m, 3H), 2.3-2.5 (m, 2H), 2.7-2.95 (m, 2H), 3.02-3.2 (m, 1H), 3.65-3.80 (m, 1H), 3.88 (s, 3H), 4.3-4.5 (m, 1H), 5.02 (t, J=10.6 Hz, 1H), 5.91 (d, J=11.3 Hz, 1H), 6.39 (t, J=11.3 Hz, 1H), 7.22 (d, J=8.0 Hz, 2H), 7.93 (d, J=8.0 Hz, 2H); $^{13}$C NMR (CDCl$_3$): 14.7, 17.2, 23.1, 26.7, 30.7, 30.9, 34.5, 40.7, 42.4, 52.5, 55.9, 118.0, 126.9, 128.2, 128.5, 128.7, 129.6, 143.3, 144.2, 166.5, 174.6 MS calculated for $C_{23}H_{31}NO_3$: 369; Found (m/z): 370 (m+1).

Methyl 4-(2-{(2R)-2-[(1E,3E)-4-methylocta-1,3-dienyl]-5-oxopyrrolidin-1-yl}ethyl)benzoate $^1$H NMR (CDCl$_3$): δ 0.90 (t, J=7.32 Hz, 3H), 1.18-1.5 (m, 6H), 1.62-1.84 (m, 1H), 1.74 (s, 3H), 1.96-2.18 (m, 3H), 2.26-2.48 (m, 2H), 2.76-2.88 (m, 2H), 3.1-3.26 (m, 1H), 3.7-3.86 (m, 2H), 3.89 (s, 3H), 4.3-4.5 (m, 1H), 5.17 (dd, $J_1$=14.8 Hz, $J_2$=9.1 Hz, 1H), 5.76 (d, J=11.0 Hz, 1H), 6.26 (dd, $J_1$=14.8 Hz, $J_2$=11.0 Hz, 1H), 7.24 (d, J=8.8 Hz, 2H), 7.96 (d, J=8.4 Hz, 2H); $^{13}$C NMR (CDCl$_3$): 14.7, 17.4, 23.1, 26.9, 30.5, 30.8, 34.5, 40.1, 42.5, 52.5, 62.4, 122.8, 128.1, 128.8, 129.6, 1301, 141.4, 144.2, 166.5, 174.9; MS calculated for $C_{23}H_{31}NO_3$: 369; Found (m/z): 370 (m+1).

Examples 3 and 4

To a solution of the alcohol mixture (510 mg, 1.37 mmol) in MeOH/THF/$H_2O$ (6/6/2 mL) was added NaOH (1.0 M, 3.4 mL, 3.4 mmol). The mixture was stirred overnight. Then the reaction mixture was concentrated under reduced pressure. The crude mixture of diastereoisomers was purified by RP-HPLC using ACN/$H_2O$/TFA to afford the desired compounds.

Example 3

4-(2-{(2R)-2-[(1Z,3E)-4-methylocta-1,3-dienyl]-5-oxopyrrolidin-1-yl}ethyl)benzoic acid (First isomer in HPLC: ACN/$H_2O$ 0.1% TFA, 197 mg): $^1$H NMR (CDCl$_3$): δ 0.90 (t, J=7.32 Hz, 3H), 1.2-1.54 (m, 6H), 1.60-1.9 (m, 1H), 1.78 (s, 3H), 2.06-2.5 (m, 3H), 2.66-2.98 (m, 2H), 3.02-3.18 (m, 1H), 3.6-3.78 (m, 1H), 4.57 (m, 1H), 5.09 (t, J=10.6 Hz, 1H), 6.11 (d, J=11.7 Hz, 1H), 6.47 (t, J=11.3 Hz, 1H), 7.15 (d, J=8.0 Hz, 2H), 7.87 (d, J=8.0 Hz, 2H); $^{13}$C NMR (CDCl$_3$): 13.7, 15.8, 22.7, 26.0, 30.5, 33.6, 40.1, 42.4, 56.0, 118.3, 126.5, 127.6, 128.4, 129.0, 135.7, 140.8, 142.5, 173.5, 175 MS calcd. for $C_{23}H_{29}NO_3$: 355; Found (m/z): 356 (m+1).

Example 4

4-(2-{(2R)-2-[(1E,3E)-4-methylocta-1,3-dienyl]-5-oxopyrrolidin-1-yl}ethyl)benzoic acid (Second isomer in HPLC: ACN/H$_2$O/TFA, 200 mg): $^1$H NMR (CDCl$_3$): δ 0.91 (t, J=7.32 Hz, 3H), 1.2-1.48(m, 6H), 1.60-1.84 (m, 1H), 1.77 (s, 3H), 2.02-2.2 (m, 2H), 2.24-2.42 (m, 1H), 2.72-2.94 (m, 1H), 3.1-3.22 (m, 1H), 3.58-3.72 (m, 1H), 3.88-4.0 (m, 1H), 3.6-3.7 (m, 1H), 3.9-4.0 (m, 1H), 5.17 (dd, J$_1$=14.8 Hz, J$_2$=9.1 Hz, 1H), 5.82 (d, J=10.6 Hz, 1H), 6.39 (dd, J$_1$=14.8 Hz, J$_2$=11.0 Hz, 1H), 7.16 (d, J=8.4 Hz, 2H), 7.87 (d, J=8.0 Hz, 2H); MS calculated. for CH$_{23}$H$_{29}$NO$_3$: 355; Found (m/z): 356 (m+1).

Compounds of Examples 3 and 4 were also synthesized according to the following protocol below.

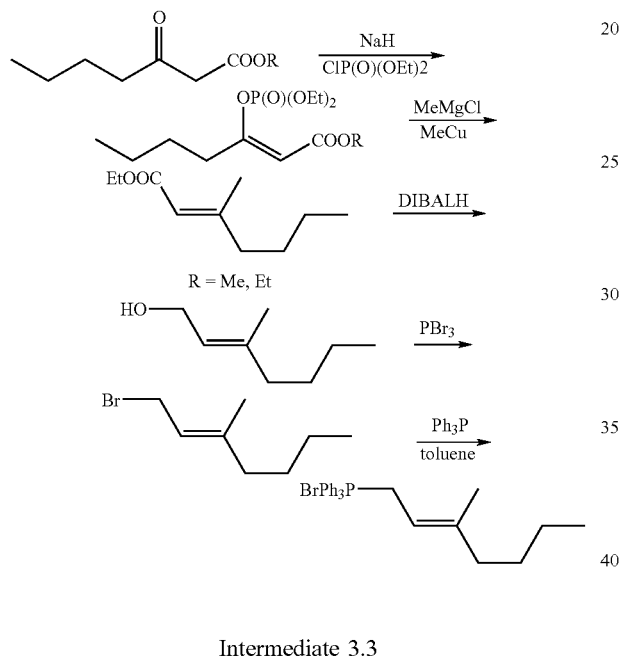

Intermediate 3.3 methyl (2Z)-3-[(diethoxyphosphoryl)oxy]hept-2-enoate

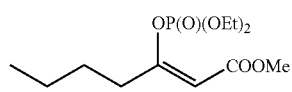

To NaH (60% in mineral oil, 2.8 g, 70 mmol) suspension in ether at 0° C. was added methyl 3-oxoheptanoate (10 g, 63 mmol) in anhydrous ether (50 mL) dropwise under Ar. The reaction mixture was stirred for 30 minutes. Diethyl chlorophosphate (9.6 mL, 67 mmol) was added dropwise under Ar at 0° C. The reaction mixture was stirred overnight allowing warm to room temperature. Saturated aqueous NH$_4$Cl (22 mL) was added to quench the reaction. The mixture was then acidified with 1.0 N HCl. After separation, organic phase was washed with saturated aqueous NaHCO$_3$, brine, dried (Na$_2$SO$_4$), filtered, concentrated. After column purification (silica gel, 1:1 EtOAc/Hexanes), the product was obtained as a colorless oil (17 g, 91%). $^1$HNMR (CDCl$_3$) δ 0.89~0.93 (m, 3H), 1.30~1.45 (m, 3M), 1.50~1.60 (m, 2H), 2.42 (m, 2H), 3.68 (s, 3H), 4.20~4.35 (m, 4H), 5.35 (s, 1H).

Intermediate 3.4 methyl (2E)-3-methylhept-2-enoate (This intermediate was synthesized according to the procedure reported in *Can J. Chem.* 1993, 71, 1955).

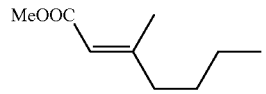

To CuI (super pure, 3.57 g, 18.7 mmol) was added anhydrous THF (100 mL), the suspension was stirred at 0° C. for 30 min. MeLi (1.4 M in ether, 13.3 mL, 18.6 mmol) were added dropwise under Ar. The mixture was stirred for 2 hr, and cooled down to −30° C. MeMgCl was added dropwise under Ar, and the mixture was stirred for 15 min., intermediate 3.3 (1.82 g, 6.2 mmol) in THF (25 mL) was added dropwise, and the reaction mixture was stirred at −30° C. for 3 hr. The reaction mixture was poured into ice-cold saturated aqueous NH$_4$Cl and 30% NH$_3$ in water (100 mL of 1:1). After separation, the organic phase was diluted by adding ether (150 mL), which was washed with 1:1 saturated aqueous NH$_4$Cl:30% NH$_3$ in water (4×50 mL) until no blue color in aqueous phase. The organic phase was washed with brine, dried (Na$_2$SO$_4$), concentrated. The obtained crude product was used for next step without further purification.

Intermediate 3.5 methyl (2E)-3-methylhept-2-enoate

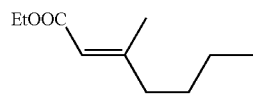

This intermediate was obtained from ethyl 3-oxobutanoate according literature (*Chem. Lett.* 1973, 1097-1100).

Intermediate 3.6

(2E)-3-methylhept-2-en-1-ol

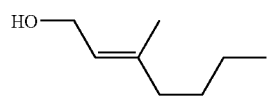

To a solution of intermediate 3.5 (0.95 g, 6.1 mml) or intermediate 3.5 (1.0 g, 6.1 mmol) in ether (25 mL) at 0° C. was added DIBAL-H (1.0 M in toluene) dropwise under Ar. The mixture was stirred at 0° C. for 2 hr and was quenched with saturated aqueous NH$_4$Cl. After dilution with ether (60 mL) the mixture was acidified with 1 N HCl and separated. The aqueous phase was extracted with ether (2×20 mL). The combined organic phase was washed with brine, dried (Na$_2$SO$_4$), concentrated. Flash column purification (silica gel, 4:1 Hex/EtOAc) afforded the product as a colorless oil (0.52 g, 67%). $^1$HNMR (CDCl$_3$) δ 0.85~0.95 (m, 3H), 1.25~1.45 (m, 4H), 1.65 (s, 3H), 1.95~2.10 (m, 2H), 4.18~4.25 (m, 2H), 5.49 (m, 1H).

Intermediate 3.7

(2E)-1-bromo-3-methylhept-2-ene. (Scheme 5)

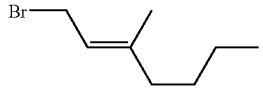

To intermediate 3.6 (0.52 g, 4.1 mmol) in petroleum ether (9 mL) at −5° C. under Ar was added PBr$_3$ (1.87 g, 6.9 mmol) in petroleum ether (3 mL). The mixture was stirred at −5° C. for 2 hr and then poured into ice water/ether (20 mL). After separation, the aqueous phase was extracted ether (2×25 mL). The combined organic phase was washed with 5% NaHCO$_3$, brine, dried (Na$_2$SO$_4$), concentrated, thus obtained crude bromide (0.76 g, 98%) was used directly for next step.

Intermediate 3.1

(2E)-3-methylhept-2-heptenyltriphenylphosphonium bromide. (Scheme 5)

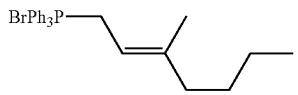

To intermediate 3.5 (0.76 g, 4.1 mmol) in toluene (10 mL) was added a solution of Ph$_3$P (1.1 g, 4.1 mmol) in toluene (10 mL). The solution mixture was heated at 110° C. for 2 hr, then allowed to cool down to room temperature. After filtratation, the product was collected as a white solid (1.0 g, 55%), and was recrystalized in acetone/hex.

Intermediate 3.2 methyl 4-(2-{(2R)-2-[(1Z,3E)-4-methylocta-1,3-dienyl]-5-oxopyrrolidin-1-yl}ethyl)benzoate and methyl 4-(2-{(2R)-2-[(1E,3E)-4-methylocta-1,3-dienyl]-5-oxopyrrolidin-1-yl}ethyl)benzoate. (Scheme 6)

To a suspension of intermediate 3.6 (150 mg, 0.332 mmol) in anhydrous THF (5 mL) at −5° C. was added n-BuLi (0.14 mL, 1.6 M, 0.365 mmol) in hexane dropwise under Ar. The mixture was stirred for 20 min after addition was complete. To the reaction mixture was then added a solution of intermediate 1.4 (91 mg, 0.332 mmol) in anhydrous THF (1 mL) dropwise. The stirring was continued for 1 hr. Water was added to quench the reaction and the mixture was concentrated in vacuo to remove most of the THF. Extraction with ethyl acetate, washing organic phase with brine, drying and concentration afforded the crude product mixture (Intermediates 3.7.1 and 3.7.2) containing cis and trans compounds as a pale oil, which was used directly for step without further purification.

Examples 3 and 4

To a solution of the Intermediates 3.2 mixture (510 mg, 1.37 mmol) in MeOH/THF/H$_2$O (6/6/2 mL) was added NaOH (1.0 M, 3.4 mL, 3.4 mmol). The mixture was stirred overnight. Then the reaction mixture was concentrated under reduced pressure. The crude mixture of diastereoisomers was purified by RP-HPLC using ACN/H$_2$O/TFA to afford the desired compounds.

Example 3

4-(2-{(2R)-2-[(1Z,3E)-4-methylocta-1,3-dienyl]-5-oxopyrrolidin-1-yl}ethyl)benzoic acid (First isomer in HPLC: ACN/H$_2$O 0.1% TFA, 197 mg): $^1$H NMR (CDCl$_3$): δ 0.90 (t, J=7.32 Hz, 3H), 1.2-1.54 (m, 6H), 1.60-1.9 (m, 1H), 1.78 (s, 3H), 2.06-2.5 (m, 3H), 2.66-2.98 (m, 2H), 3.02-3.18 (m, 1H), 3.6-3.78 (m, 1H), 4.57 (m, 1H), 5.09 (t, J=10.6 Hz 1H), 6.11 (d, J=11.7 Hz, 1H), 6.47 (t, J=11.3 Hz, 1H), 7.15 (d, J=8.0 Hz, 2H), 7.87 (d, J=8.0 Hz, 2H); $^{13}$C NMR (CDCl$_3$): 13.7, 15.8, 22.7, 26.0, 30.5, 33.6, 40.1, 42.4, 56.0, 118.3, 126.5, 127.6, 128.4, 129.0, 135.7, 140.8, 142.5, 173.5, 175 MS (m/z): 356 (m+H).

Example 4

4-(2-{(2R)-2-[(1E,3E)-4-methylocta-1,3-dienyl]-5-oxopyrrolidin-1-yl}ethyl)benzoic acid (Second isomer in HPLC: ACN/H$_2$O/TFA, 200 mg): $^1$H NMR (CDCl$_3$): δ 0.91 (t, J=7.32 Hz, 3H), 1.2-1.48(m, 6H), 1.60-1.84 (m, 1H), 1.77 (s, 3H), 2.02-2.2 (m, 2H), 2.24-2.42 (m, 1H), 2.72-2.94 (m, 1H), 3.1-3.22 (m, 1H), 3.58-3.72 (m, 1H), 3.88-4.0 (m, 1H), 3.6-3.7 (m, 1H), 3.9-4.0 (m, 1H), 5.17 (dd, J$_1$=14.8 Hz, J$_2$=9.1 Hz, 1H), 5.82 (d, J=10.6 Hz, 1H), 6.39 (dd, J$_1$=14.8 Hz, J$_2$=11.0 Hz, 1H), 7.16 (d, J=8.4 Hz, 2H), 7.87 (d, J=8.0H, 2H); MS (m/z): 356 (m+H).

Example 3

Synthesis of 4-(2-{(2R)-2-[(1Z,3E)-4-methylocta-1,3-dienyl]-5-oxopyrrolidin-1-yl}ethyl)benzoic acid

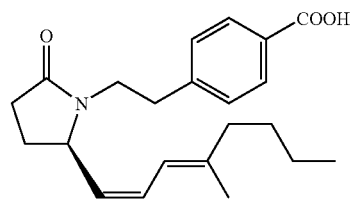

Intermediate 3.7

Methyl 4-{2-[(2R)-2-(2,2-dibromovinyl)-5-oxopyrrolidinyl]ethyl}benzoate (Scheme 7)

To a solution of Intermediate 1.4 (2.97 g, 10.8 mmol) and carbon tetrabromide (3.95 g, 11.9 mmol) in CH$_2$Cl$_2$ was added triphenylphosphine (6.24 g, 23.8 mmol) in 4 portions over 15 min at 0° C. The yellow solution was allowed to warm to 25° C., stirred for 1 h, poured on hexanes (250 mL) and filtered on celite. The filtrate was concentrated in vacuo and the residue was purified by chromatography (hexanes/AcOEt 1:4) to afford methyl 4-{2-[(2R)-2-2,2-dibromovinyl)-5-oxopyrrolidinyl]ethyl}benzoate (3.92 g, 83%) as a colorless oil: $^1$H NMR (CDCl$_3$) δ 1.68-1.78 (m, 1H), 1.98-2.46 (m, 3H), 2.83-3.00 (m, 2H), 3.12-3.20 (m, 1H), 3.73-3.81 (m, 1H), 3.90 (s, 3H), 4.18-4.24 (m, 1H), 6.14 (d, J=8.8 Hz, 1H), 7.29 (d, J=8.1 Hz, 2H), 7.98 (d, J=8.1 Hz, 2H).

Intermediate 3.8

Methyl 4-(2-{(2R)-2-[(Z)-2-bromoethenyl]-5-oxopyrrolidinyl}ethyl)benzoate

To a degassed solution of Intermediate 3.7 (3.90 g, 9.05 mmol) in toluene (60 mL), was added tetrakis(triphenylphosphine)palladium(0) (523 mg, 0.453 mmol). The yellow solution was cooled at 0° C. before tributyltin hydride (2.68 mL, 2.90 g, 9.96 mmol) was added dropwise. The reaction mixture was stirred at 0° C. during 1 h, diluted with hexanes (300 mL) and washed with water (150 mL) and brine (150 mL), dried over sodium sulfate and concentrated in vacuo. The residue was purified by chromatography (hexanes/AcOEt 1:4) to afford methyl 4-(2-{(2R)-2-[(Z)-2-bromoethenyl]-5-oxopyrmolidinyl}ethyl)benzoate (2.84 g, 89%) as a colorless oil: $^1$H NMR (CDCl$_3$) δ 1.67-1.75 (m, 1H), 2.20-2.47 (m, 3H), 2.81-3.00 (m, 2H), 3.04-3.12 (m, 1H), 3.78-3.86 (m, 1H), 3.89 (s, 3H), 4.49-4.55 (m, 1H), 5.92 (dd, J=9.2, 7.0 Hz 1H), 6.40 (d, J=6.9 Hz, 1H), 7.28 (d, J=8.1 Hz, 2H), 7.96 (d, J=8.4 Hz, 2H).

Intermediate 3.9

(1E)-1-Iodo-2-methyl-1-hexene

To a slurry of dichlorobis[η5-cyclopentadienyl]zirconium (8.77 g, 30.0 mmol) in 1,2-dichloroethane (75 mL) was added trimethylalane (60 mL, 30 mmol, 2 M solution in hexanes) under nitrogen at 25° C. The reaction mixture was stirred for 15 min until the dichlorobis[η5-cyclopentadienyl] zirconium was dissolved. To the resulting lemon-yellow solution was added 1-hexyne (3.47 mL, 2.47 g, 30.0 mmol). After the reaction mixture was stirred for 3 h, a solution of iodine (9.14 g, 36.0 mmol) in tetrahydrofuran (50 mL) was added dropwise at 0° C. The reaction mixture was allowed to warm to 25° C., stirred for 1 h, poured cautiously on ice (200 mL), acidified with 1 N HCl and extracted with ether (200 mL). The organic phase was washed with 1 N HCl (100 mL), a saturated solution of sodium bisulfite (100 mL) and brine (100 mL), dried over sodium sulfate and concentrated in vacuo. Distallation of the residue afforded (1E)-1-iodo-2-methyl-1-hexene (4.81 g, 72%) as a colorless liquid: b.p. 58-60° C./10 mmHg; $^1$H NMR (CDCl$_3$) δ 0.89 (t, J=7.0 Hz, 3H), 1.22-1.32 (m, 2H), 1.36-1.44 (m, 2H), 1.82 (s, 3H), 2.19 (t, J=7.0 Hz, 2H), 5.85 (s, 1H).

Intermediate 3.10

(1E)-2-Methyl-1-hexenylboronic acid

To a solution of Intermediate 3.9 (2.00 g, 8.93 mmol) in THF (40 mL) was added butyllithium (12.3 mL, 1.6 M in hexanes, 19.6 mmol) at −78° C. and the mixture was stirred for 10 min. Triisopropyl borate (10.4 mL, 8.39 g, 44.6 mmol) was then added to the reaction mixture, which was allowed to warm to 25° C. and stirred or an additional 30 min. The suspension was filtered on celite, concentrated in vacuo and purified by chromatography (hexanes/AcOEt 3:1) to afford (1E)-2-methyl-1-hexenylboronic acid (0.96 g, 76%) as a colorless liquid: $^1$H NMR (CDCl$_3$) δ 0.90 (t, J=7.3 Hz, 3H), 1.26-1.36 (m, 2H), 1.39-1.49 (m, 2H), 2.09 (s, 3H), 2.14 (t, J=7.7 Hz, 2H), 5.22 (s, 1H).

Intermediate 3.11

Methyl 4-(2-{(2R)-2-[(1Z,3E)-4-methyl-1,3-octadienyl]-5-oxopyrrolidinyl}ethyl)-benzoate Tetrakis(triphenylphosphine)palladium(0) (164 mg, 0.14 mmol), an aqueous solution of potassium hydroxide (28.4 mL, 2 N), and silver carbonate (1.57 g, 5.68 mmol) were successively added at 25° C. to a mixture of Intermediate 3.8 (500 mg, 1.42 mmol) and Intermediate 3.10 (484 mg, 3.41 mmol) in degassed THF (10 mL). The reaction mixture was stirred 30 min at the same temperature, diluted with 10% ether in hexanes (100 mL), filtered on celite and washed with water (2×50 mL) and brine (50 mL). The organic extract was dried over sodium sulfate, concentrated in vacuo and the residue was purified by chromatography (hexanes/AcOEt 1:4) to afford methyl 4-(2-{(2R)-2-[(1Z,3E)-4-methyl-1,3-octadienyl]-5-oxopyrrolidinyl}ethyl)-benzoate (356 mg, 68%) as a colorless oil: $^1$H NMR (CDCl$_3$) δ 0.91 (t, J=7.3 Hz, 3H), 1.24-1.46 (m, 4H), 1.60-1.70 (m, 1H), 2.07 (t, J=7.3 Hz, 1H), 2.12-2.21 (m, 1H), 228-2.46 (m, 2H), 2.77-2.96 (m, 2H), 3.04-3.13 (m, 1H), 3.71-3.79 (m, 1H), 3.89 (s, 3H), 4.32-4.40 (m, 1H), 5.03 (t, J=10.6 Hz, 1H), 5.93 (d, J=10.6 Hz, 1H), 6.38 (t, J=11.0 Hz, 1H), 7.24 (d, J=8.5 Hz, 2H), 7.95 (d, J=8.4 Hz, 2H).

Example 3

To a solution of Intermediate 3.11 (350 mg, 0.947 mmol) in THF (12 mL), methanol (12 mL) and water (3 mL) was added an aqueous solution of sodium hydroxide (1.1 mL, 10 N). The reaction mixture was stirred overnight at 25° C. and concentrated in vacuo. The crude mixture was purified by RP-HPLC, using ACN/H$_2$O 0.1% NaOAc, to afford 11 (286 mg, 80%, sodium salt) as a white solid.

Example 3

4-(2-{(2R)-2-[(1Z,3E)-4-methylocta-1,3-dienyl]-5-oxopyrrolidin-1-yl}ethyl)benzoic acid $^1$H NMR (CD$_3$OD) δ 0.91 (t, J=7.3 Hz, 3H), 1.28-1.49 (m, 4H), 1.62-1.71 (m, 1H), 2.11-2.26 (m, 3H), 2.29-2.44 (m, 2H), 2.73-2.93 (m, 2H), 3.05-3.14 (m, 1H), 3.64-3.72 (m, 1H), 4.52-4.59 (m, 1H), 5.11 (t, J=10.7 Hz, 1H), 6.11 (d, J=11.3 Hz, 1H), 6.48 (t, J=11.3 Hz, 1H), 7.17 (d, J=8.4 Hz, 2H), 7.88 (d, J=8.5 Hz, 2H).

Examples 5 and 6

Synthesis of 4-(2-{(2R)-2-[(1Z)-4-methylpenta-1,3-dienyl]-5-oxopyrrolidin-1-yl}ethyl)benzoic acid and 4-(2-{(2R)-2-[(1E)-4-methylpenta-1,3-dienyl]-5-oxopyrrolidin-1-yl}ethyl)benzoic acid

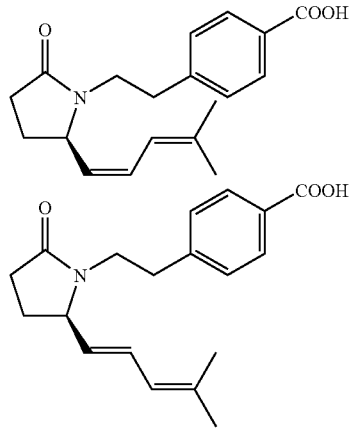

Intermediate 5.1

3-methylbut-2-enyl)(triphenyl)phosphonium bromide (Scheme 5)

To a solution of 1-bromo-2-methyl-2-butene (5.0 g, 34 mmol) in anhydrous toluene (70 mL) was added a solution of triphenylphosphine (8.8 g, 34 mmol) in anhydrous toluene (70 mL). The resulting mixture was heated at 110° C. under Ar for 2 hr. The reaction mixture was then cooled to room temperature overnight. The white precipitate was collected by filtration. After dried, the solid was subject to recrystalization using acetone/hexanes. The product was thus obtained as a white crystal. $^1$H NMR (CD$_3$OD), δ 1.33 (s, 3H), 1.71 (s, 3H), 4.18~4.30 (m, 2M), 5.15~5.20 (m, 1H), 7.70~8.05 (m, 15H).

Intermediate 5.2 methyl 4-(2-{(2R)-2-(4-methylpenta-1,3-dienyl)-5-oxopyrrolidin-1-yl}ethyl)benzoate To a suspension of intermediate 5.1 (580 mg, 1.41 mmol) in anhydrous THF (20 mL) at −5° C. was added n-BuLi (0.97 mL, 1.6 M, 1.55 mmol) in hexane dropwise under Ar. The mixture was stirred for 20 min after addition was complete. To the reaction mixture was then added a solution of methyl 4-{2-[(2R)-2-formyl-5-oxopyrrolidin-1-yl]ethyl}benzoate (intermediate 1.4) (388 mg, 1.41 mmol) in anhydrous THF (4 mL) dropwise. The stirring was continued for 1 hr. Water was added to quench the reaction and the mixture was concentrated in vacuo to remove most of the THF. Extraction with ethyl acetate, washing organic phase with brined, drying and concentration afforded the crude product mixture containing cis and trans compounds as a pale oil, which was used directly for step without further purification.

Example 5 and 6

A crude mixture of intermediate 5.2 obtained above in MeOH (8 mL) and 10 N NaOH (1.9 mL) was stirred at rt overnight. The reaction mixture was then concentrated and subject to RP HPLC. Using gradient of 100% water (0.1% TFA) to 60% water (0.1% TFA)/40% CH$_3$CN through 70 min. flow rate 100 mL/min, C18 column. Thus obtained free acid was neutralized with 1.0 N NaOH to get the sodium salt.

Example 5

4-(2-{(2R)-2-[(1Z)-4-methylpenta-1,3-dienyl]-5-oxopyrrolidin-1-yl}ethyl)benzoic acid $^1$H NMR (CD$_3$OD) δ 1.59~1.70 (m, 1H), 1.79 (s, 3H), 1.85 (s, 3H), 2.12~2.23 (m, 1H), 2.25~2.42 (m 2H), 2.72~2.82 (m, 1H), 2.86~2.95 (m, 1H), 3.05~3.16 (m, 1H), 3.65~3.75 (m, 1H), 4.46~4.52 (m, 1H), 5.06 (t, J=10.2 Hz, 1H), 6.02 (d, J=10.6 Hz, 1H), 6.44 (t, J=11.3 Hz, 1H), 7.15 (d, J=8.4 Hz, 2H), 7.87 (d, J=8.4 Hz, 2H). MS (m/z) 314.3 (M+H).

Example 6

4-(2-{(2R)-2-[(1E)-4-methylpenta-1,3-dienyl]-5-oxopyrrolidin-1-yl}ethyl)benzoic acid $^1$H NMR (CD$_3$OD) δ 1.62~1.75 (m, 1H), 1.79 (s, 6H), 2.10~2.23 (m, 1H), 2.25~2.42 (m 2H), 2.75~2.95 (m, 2H), 3.15~3.22 (m, 1H), 3.62~3.70 (m, 1H), 3.90~4.00 (m, 1H), 5.21 (dd, J=9.2, 15.1 Hz, 1H), 5.81 (d, J=11 Hz, 1H), 6.36 (dd, J=11.0, 15 Hz, 1H), 7.22 (d, J=8.1 Hz, 2H), 7.90 (d, J=8.1 Hz, 2H). MS (m/z) 314.3 (M+H).

Examples 7 and 8

Synthesis of 4-(2-{(2R)-2-[(1Z,3E)-hexa-1,3-dienyl]-5-oxopyrrolidin-1-yl}ethyl)benzoic acid and 4-(2-{(2R)-2-[(1E,3E)-hexa-1,3-dienyl]-5-oxopyrrolidin-1-yl}ethyl)benzoic acid

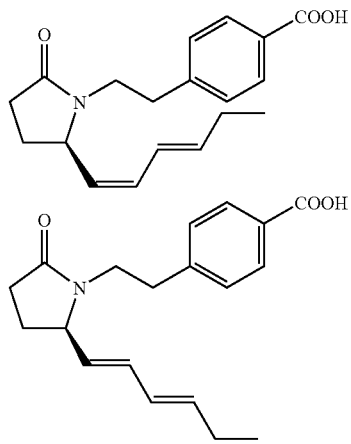

The title compound was prepared from H-Glu(O$^t$Bu)-O$^t$Bu and (2E)-1-bromopent-2-ene (from Aldrich) using the procedure of Examples 5 and 6.

Example 7

4-(2-{(2R)-2-[(1Z,3E)-hexa-1,3-dienyl]-5-oxopyrrolidin-1-yl}ethyl)benzoic acid $^1$H NMR (CD$_3$OD) δ 1.03 (t, J=7.4 Hz, 3H), 1.60~1.72 (m, 1H), 2.10~2.42 (m, 5H), 2.76~2.86 (m, 1H), 2.86~2.95 (m, 1H), 3.05~3.16 (m, 1H), 3.65~3.75 (m, 1H), 4.45~4.65 (m, 1H), 5.06 (t, J=9.5 Hz, 1H), 5.82~6.00 (m, 1H), 6.15~6.30 (m, 2H), 7.28 (d, J=8.1 Hz, 2H), 7.93 (d, J=8.1 Hz, 2H). MS (m/z) 314.2 (M+H).

Example 8

4-(2-{(2R)-2-[(1E,3E)-hexa-1,3-dienyl]-5-oxopyrrolidin-1-yl}ethyl)benzoic acid $^1$H NMR (CD$_3$OD) δ 1.02 (t, J=7.7 Hz, 3H), 1.65~1.72 (m, 1H), 2.08~2.40 (m, 5H), 3.15~3.25 (m, 1H), 3.65~3.75 (m, 1H), 3.95~4.05 (m, 1H), 5.26 (dd, J=9.1, 15 Hz, 1H), 5.75~5.85 (m, 1H), 5.98~6.20 (m, 1H), 7.29 (d, J=8.4 Hz, 2H), 7.93 (d, J=8.4 Hz, 2H). MS (m/z) 314.2 (M+H).

Examples 9 and 10

Synthesis of 4-(2-{(2R)-2-[(1Z,3E)-hepta-1,3-dienyl]-5-oxopyrrolidin-1-yl}ethyl)benzoic acid and 4-(2-{(2R)-2-[(1E,3E)-hepta-1,3-dienyl]-5-oxopyrrolidin-1-yl}ethyl)benzoic acid

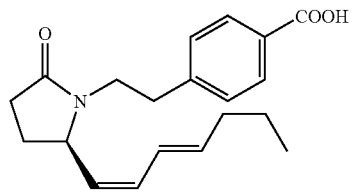

and

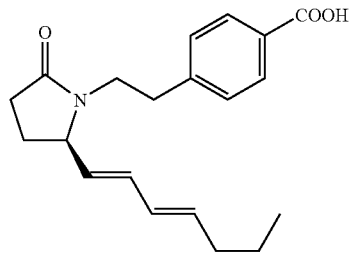

The title compound was prepared from H-Glu(O$^t$Bu)-O$^t$Bu and (2E)-1-bromohex-2-ene (obtained from (2E)-hex-2-en-1-ol as described in Watanabe et al., 1989) using the procedure of Examples 5 and 6.

Example 9

4-(2-{(2R)-2-[(1Z,3E)-hepta-1,3-dienyl]-5-oxopyrrolidin-1-yl}ethyl)benzoic acid $^1$H NMR (CD$_3$OD) δ 7.90 (d, J=8.1 Hz, 2H), 7.22 (d, J=8.1 Hz, 2H), 6.15~6.30 (m, 2H), 5.78~5.85 (m, 1H), 5.06 (t, J=9.9 Hz, 1H), 4.50~4.65 (m, 1H), 3.65~3.75 (m, 1H), 3.05~3.16 (m, 1H), 2.86~2.95 (m, 1H), 2.76~2.86 (m, 1H), 2.25~2.42 (m 2H), 2.07~2.23 (m, 3H), 1.60~1.73 (m, 1H), 1.40~1.50 (m, 2H), 0.94 (t, J=7.3 Hz, 3H). MS (m/z) 328.1 (M+H).

Example 10

4-(2-{(2R)-2-[(1E,3E)-hepta-1,3-dienyl]-5-oxopyrrolidin-1-yl}ethyl)benzoic acid (Sodium salt)

$^1$H NMR (CD$_3$OD) δ 7.87 (d, J=8.4 Hz, 2H), 7.17 (d, J=8.4 Hz, 2H), 6.00~6.15 (m, 2H), 5.75~5.82 (m, 1H), 5.27 (dd, J=9.9, 14.3 Hz, 1H), 3.85~3.95 (m, 1H), 3.60~3.70 (m, 1H), 3.10~3.20 (m, 1H), 2.75~2.95 (m, 2H), 2.20~2.42 (m 2H), 2.07~2.19 (m, 3H), 1.65~1.75 (m, 1H), 1.40~1.50 (m, 2H), 0.93 (t, J=7.3 Hz, 3H). MS (m/z) 328.1 (M+H).

Examples 11 and 12

Synthesis of 4-(2-{(2R)-2-[(1Z,3E)-4,8-dimethyl-nona-1,3,7-trienyl]-5-oxopyrrolidin-1-yl}ethyl)benzoic acid and 4-(2-{(2R)-2-[(1E,3E)-4,8-dimethyl-nona-1,3,7-trienyl]-5-oxopyrrolidin-1-yl}ethyl)benzoic acid

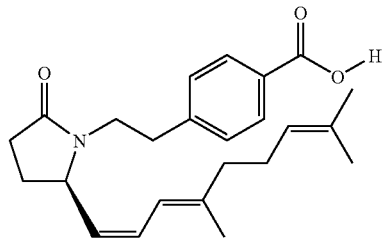

The title compound was prepared from H-Glu(O$^t$Bu)-O$^t$Bu and (2E)-1-bromo-3,7-dimethylocta-2,6-diene (from Aldrich) using the procedure of Examples 5 and 6.

Example 11

4-(2-{(2R)-2-[(1Z,3E)-4,8-dimethylnona-1,3,7-trienyl]-5-oxopyrrolidin-1-yl}ethyl)benzoic acid $^1$H NMR (CD$_3$OD) δ 1.59 (s, 3H), 1.63 (s, 3H), 1.81 (s, 3H), 1.70~2.50 (m 8H), 2.70~2.80 (m, 1H), 2.85~2.95 (m, 1H), 3.05~3.15 (m, 1H), 3.65~3.75 (m, 1H), 4.50~4.50 (m, 1H), 5.12 (t, J=10.5 Hz, 1H), 6.13 (d, J=11.8 Hz, 1H), 6.48 (t, J=11.1 Hz, 1H), 7.16 (d, J=8.1 Hz, 2H), 7.87 (d, J=8.1 Hz, 2H). MS (m/z) 382.4 (M+H).

Example 12

4-(2-{(2R)-2-[(1E,3E)-4,8-dimethylnona-1,3,7-trienyl]-5-oxopyrrolidin-1-yl}ethyl)benzoic acid $^1$H NMR (CD$_3$OD) δ 1.60 (s, 3H), 1.79 (s, 3H), 1.70~2.50 (m 8H), 2.70~2.95 (m, 2H), 3.10~3.20 (m, 1H), 3.60~3.70 (m, 1H), 3.90~4.00 (m, 1H), 5.05~5.15 (m, 1H), 5.26 (dd, J=9, 15 Hz, 1H), 6.37 (dd, J=11, 15 Hz, 1H), 5.83 (d, J=10.6 Hz, 1H), 7.17 (d, J=8.1 Hz, 2H), 7.87 (d, J=8.1 Hz, 2H). MS (m/z) 382.4 (M+H).

Examples 13 and 14

Synthesis of 5-(3-{(2R)-2-[(1Z,3E)-4-methylocta-1,3-dienyl]-5-oxopyrrolidin-1-yl}propyl)thiophene-2-carboxylic acid and 5-(3-{(2R)-2-[(1E,3E)-4-methylocta-1,3-dienyl]-5-oxopyrrolidin-1-yl}propyl)thiophene-2-carboxylic acid

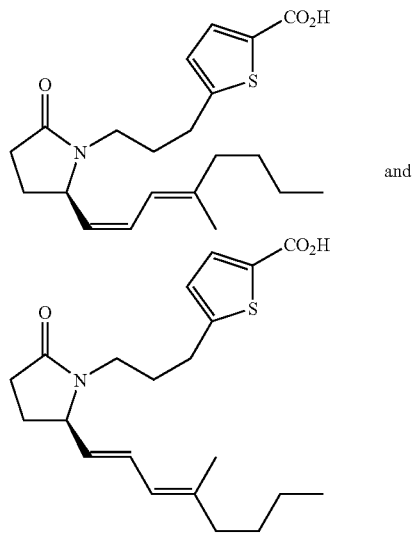

Intermediate 13.1

Methyl 5-[3-(2-formyl-5-oxopyrrolidin-1-yl)propyl]thiophene-2-carboxylate. (Scheme 3)

A DCM solution of oxalyl chloride (4.38 mL, 2.0 M 8.76 mmol) was diluted with dry DCM (50 mL) and cooled to −78° C. then a solution of DMSO (0.76 mL, 10.77 mmol) in DCM (5 mL) was added dropwise. After 15 min., a solution of methyl 5-[3-(2-(hydroxymethyl)-5-oxopyrrolidin-1-yl)propyl]thiophene-2-carboxylate (2.0 g, 6.73 mmol) in DCM (10 mL) was added dropwise to this solution. The resulting solution was stirred at −78° C. for 2 hours. Et$_3$N (4.7 mL, 33.65 mmol) was added and the solution warmed to RT. After 15 min. the solution was diluted with DCM (100 mL) and washed with a saturated solution of NH$_4$Cl (2×100 mL), brine (100 mL), dried over sodium sulfate and concentrated in vacuo to afford the aldehyde intermediate (1.95 g, 98%) used in the next step without further purification.

Intermediate 13.2

Methyl 5-(3-{(2R)-2-[(1E/Z,3E)-4-methylocta-1,3-dienyl]-5-oxopyrrolidin-1-yl}propyl)thiophene-2-carboxylate. (Scheme 6)

(3-Hydroxy-3-methylheptyl)triphenyl)phosphonium bromide (1.20 g, 2.54 mmol) in anhydrous THF (35 mL) cooled at −78° C. was added dropwise n-butyl lithium (1.6 M in hexane, 3.39 mL, 5.42 mmol) for 10 minutes, After 20 minutes, Intermediate 1.1 (500 mg, 1.82 mmol) in THF (3 mL) was added to the above mixture. After 30 minutes, the mixture was warm to room temperature. The mixture was stirred for 30 minutes at room temperature. The reaction was quenched with addition of 1 mL of water. The organic layer was washed with brine (3×10 mL), dried over with MgSO$_4$. After evaporation of the solvent, the crude product was used for the next reaction without purification.

Examples 13 and 14

To a solution of the above lactam diene in MeOH/THF/H$_2$O (6/6/2 mL) was added NaOH (1.0 M, 3.4 mL, 3.4 mmol). The mixture was stirred for overnight. After concentration under reduced pressure, the residue was purified through RP-HPLC using ACN and H$_2$O/0.1% TFA to afford Sample 1 (117 mg) and Sample 2 (120 mg) as a white solid.

Example 13

5-(3-{(2R)-2-[(1Z,3E)-4-methylocta-1,3-dienyl]-5-oxopyrrolidin-1-yl}propyl)thiophene-2-carboxylic acid (the first isomer from RP-HPLC (ACN/H$_2$O 0.1% TFA)

$^1$H NMR (CD$_3$OD): δ 0.956 (t, J=7.3 Hz, 3H), 1.32-1.44 (m, 6H), 1.81 (s, 3H), 1.90 (m, 2H), 2.14 (m, 1H), 2.42 (m, 2H), 2.79 (m, 2H), 3.02 (m, 1H), 3.35 (m, 1H), 4.76 (m, 1H), 5.18 (m, 1H), 6.24 (d, J=11.3 Hz, 1H), 6.51 (m, 1H), 6.76 (d, J=3.6 Hz, 1H), 7.38 (d, J=3.6 Hz, 1H), MS (m/z): 375.5 (M$^+$).

Example 14

5-(3-{(2R)-2-[(1E,3E)-4-methylocta-1,3-dienyl]-5-oxopyrrolidin-1-yl}propyl)thiophene-2-carboxylic acid (the second isomer from RP-HPLC (CAN/H$_2$O/TFA)

$^1$HNMR (CD$_3$OD): δ 0.912 (t, J=7.3 Hz, 3H), 1.26-1.38 (m, 6H), 1.73 (s, 3H), 1.90 (m, 2H), 2.04 (m, 1H), 2.42 (m, 2H), 2.82 (m, 2H), 3.03 (m, 1H), 3.45 (m, 1H), 4.17 (m, 1H), 5.33 (dd, J=13 and 15 Hz, 1H), 5.81 (d, J=10.6 Hz, 1H), 6.46 (d, J=13 and 15 Hz, 1H), 6.86 (d, J=3.6 Hz, 1H), 7.58 (d, J=3.6 Hz, 1H), MS (m/z): 376.2 (M+H$^+$).

Example 15

Synthesis of 4-(2-{(2R)-2-[(1Z and 1E,3Z)-hepta-1,3-dienyl]-5-oxopyrrolidin-1-yl}ethyl)benzoic acid

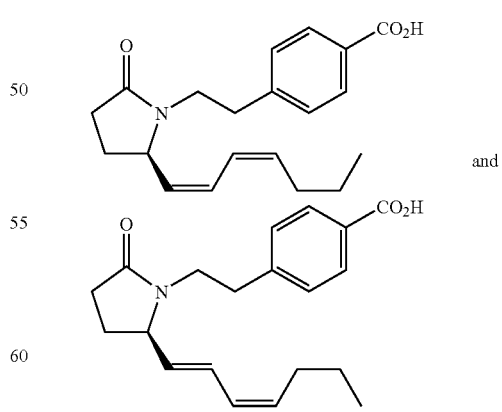

The title compound was prepared as a mixture of diastereoisomers (1Z and 1E) from H-Glu(O$^t$Bu)-O$^t$Bu and (2Z)-1-bromohex-2-ene using the procedure of Example 11. MS (m/z) 314.3 (M+H).

Example 16

Synthesis of 4-(2-{(2R)-2-[(1E and 1E,3Z)-hexa-1,3-dienyl]-5-oxopyrrolidin-1-yl}ethyl)benzoic acid

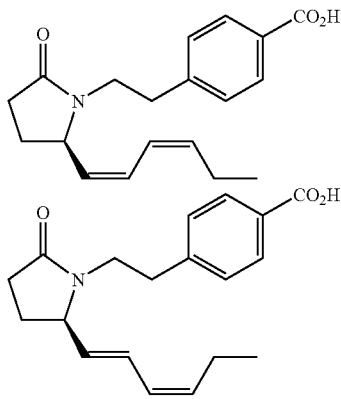

The title compound was prepared as a mixture of diastereoisomers (1Z and 1E) from H-Glu(OtBu)-OtBu and (2E)-1-bromopent-2-ene (Aldrich) using the procedure of Examples 5 and 6. MS (m/z) 314.3 (M+H).

Example 17 and 18

Synthesis of 5-(3-{(2R)-2-[(3E)-octa-1,3-dienyl]-5-oxopyrrolidin-1-yl}propyl)thiophene-2-carboxylic add

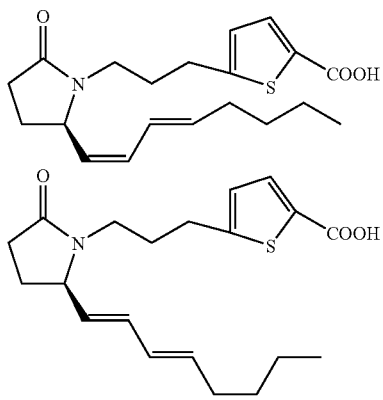

The title compound was prepared as a mixture of diastereoisomers (1Z and 1E) from methyl 5-{3-[(2R)-2-formyl-5-oxopyrrolidin-1-yl]propyl}thiophene-2-carboxylate (prepared from (5R)-5-(hydroxymethyl)pyrrolidin-2-one according to WO 0242268) and (2E)-1-bromohept-2-ene using the procedure of Examples 11 and 12.

Example 17

5-(3-{(2R)-2-[(1Z,3E)-octa-1,3-dienyl]-5-oxopyrrolidin-1-yl}propyl)thiophene-2-carboxylic acid sodium salt $^1$H-NMR (CD$_3$OD) δ 7.42 (d, J=3.7 Hz, 1H), 6.78 (d, J=3.7 Hz, 1H), 6.36~6.48 (m, 1H), 6.14~6.24 (m, 1H), 5.76~5.88 (m, 1H), 5.08~5.16 (m, 1H), 4.65~4.78 (m, 1H), 3.40~3.55 (m, 1H), 2.90~3.05 (m, 1H), 2.70~2.85 (m, 2H), 2.10~2.45 (m, 5H), 1.60~2.00 (m, 3H), 1.20~1.45 (m 4H), 0.85~0.95 (m, 3H). MS (m/z) 362.0 (M+H).

Example 18

5-(3-{(2R)-2-[(1E,3E)-octa-1,3-dienyl]-5-oxopyrrolidin-1-yl}propyl)thiophene-2-carboxylic acid Sodium salt $^1$H-NMR (CD$_3$OD) δ 7.35 (d, J=3.5 Hz, 1H), 6.74 (d, J=3.5 Hz, 1H), 6.16~6.26 (m, 1H), 6.00~6.10 (m, 1H), 5.70~5.81 (m, 1H), 5.34~5.44 (m, 1H), 4.10~4.20 (m, 1H), 3.45~3.55 (m, 1H), 2.95~3.05 (m, 1H), 2.70~2.85 (m, 2H), 2.05~2.45 (m, 5H), 1.65~1.95 (m, 3H), 1.25~1.45 (m 4H), 0.85~0.95 (m, 3H). MS (m/z) 362.0 (M+H).

Examples 19 and 20

5-(3-{(2R)-2-[(1Z and EZ,3E)-4-methylocta-1,3-dienyl]-5-oxopyrrolidin-1-yl}propyl)thiophene-2-carboxylic acid

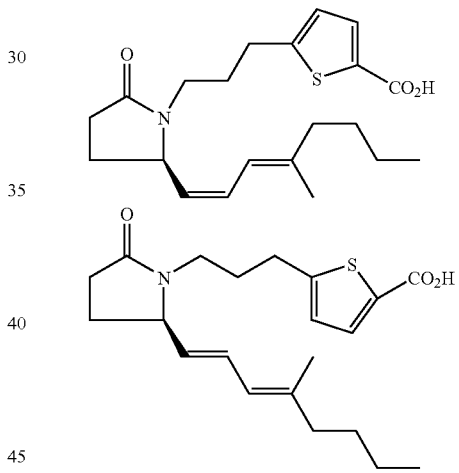

The title compound was prepared from methyl 5-{3-[(2R)-2-formyl-5-oxopyrrolidin-1-yl]propyl}thiophene-2-carboxylate (prepared from (5R)-5-(hydroxymethyl)pyrrolidin-2-one according to WO 0242268) and 3-(R,S)-hydroxy-3-methyl-1-heptyl bromide using the procedure of Examples 3 and 4.

Example 19

5-(3-{(2R)-2-[(1Z,3E)-4-methylocta1,3-dienyl]-5-oxopyrrolidin-1-yl}propyl)thiophene-2-carboxylic acid (the first isomer from RP-HPLC (ACN/H$_2$O/TFA)

$^1$HNMR (CD$_3$OD): δ 0.956 (t, J=7.3 Hz, 3H), 1.32-1.44 (m, 6H), 1.81 (s, 3H), 1.90 (m, 2H), 2.14 (m, 1H), 2.42 (m, 2H), 2.79 (m, 2H), 3.02 (m, 1H), 3.35 (m, 1H), 4.76 (m, 1H), 5.18 (m, 1H), 6.24 (d, J=11.3 Hz, 1H), 6.51 (m, 1H), 6.76 (d, J=3.6 Hz, 1H), 7.38 (d, J=3.6 Hz, 1H), MS (m/z): 375.5 (M$^+$)

Example 20

5-(3-{(2R)-2-[(1E,3E)-4-methylocta-1,3-dienyl]-5-oxopyrrolidin-1-yl}propyl)thiophene-2-carboxylic acid (the second isomer from RP-HPLC (ACN/H₂O/TFA)

¹HNMR (CD₃OD): δ 0.912 (t, J=7.3 Hz, 3H), 1.26-1.38 (m, 6H), 1.73 (s, 3H), 1.90 (m, 2H), 2.04 (m, 1H), 2.42 (m, 2H), 2.82 (m, 2H), 3.03 (m, 1H), 3.45 (m, 1H), 4.17 (m, 1H), 5.33 (dd, J=13 and 15 Hz, 1H), 5.81 (d, J=10.6 Hz, 1H), 6.46 (d, J=13 and 15 Hz, 1H), 6.86 (d, J=3.6 Hz, 1H), 758 (d, J=3.6 Hz, 1H), MS (m/z): 376.2 (M+H⁺)

Examples 21 and 22

Synthesis of 4-(2-{(2R)-2-[(1Z,3E)-3-methylocta-1,3-dienyl]-5-oxopyrrolidin-1-yl}ethyl)benzoic acid and 4-(2-{(2R)-2-[(1Z,3E)-3-methylocta-1,3-dienyl]-5-oxopyrrolidin-1-yl}ethyl)benzoic acid

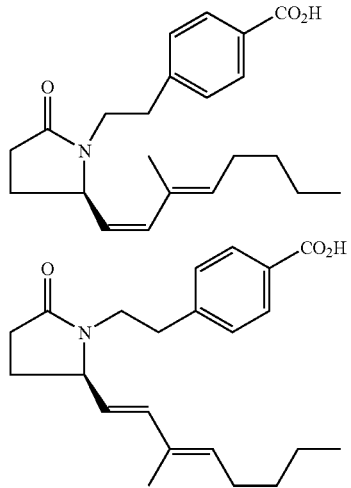

Intermediate 21.1

Ethyl (2E)-2-methylhex-2-enoate

Valeraldehyde (2.5 g, 29.02 mmol) and (carbethoxyethylidene)triphenyl phosphorane (12.54 g, 34.83 mmol) in methylene chloride was refluxed for 7 hours. After cooling to room temperature, the solvent was evaporated. The residue was purified through flash chromatography on silica gel (EtOAc:Hexanes=2:98) to give 4.2 g as colorless oil in 85% yield. ¹HNMR (CD₃Cl): δ 0.920 (t, J=7.4 Hz, 3H), 1.30 (m, 7H), 1.81 (s, 3H), 2.19 (t, J=7.4 Hz, 2H), 4.18 (q, J=7.4 Hz, 2H), 6.75 (t, J=7.4 Hz, 1H).

Intermediate 21.2

(2E)-2-methylhex-2-en-1-ol

Intermediate 21.1 (4.2 g, 24.67 mmol) in methylene chloride (100 mL) at -78° C. was added DIBALH (61.67 mL, 67.67 mmol, 1.0 M in hexanes). The mixture was stirred for 2 hours and quenched with an addition of 1 mL of methanol. The mixture was washed with brine and dried over MgSO₄. The residue was purified through flash chromatography on silica gel (EtOAc:Hexanes=1:4) to give 2.8 g as colorless oil in 88% yield. ¹HNMR (CD₃Cl): δ 0.908 (t, J=7.4 Hz, 3H), 1.31 (m, 4H), 1.66 (s, 3H), 2.01 (t, J=7.4 Hz, 2H), 3.99 (s, 2H), 5.40 (t, J=7.4 Hz, 1H).

Intermediate 21.3

(2E)-1-bromo-2-methylhex-2-ene

Intermediate 21.2 (1.4 g, 10.92 mmol) in ether (10 mL) at 0° C. was added phosphorus bromide (1.21 mL, 13.10 mmol). The mixture was stirred for 2 hours and quenched with addition of saturated sodium bicarbonate. The ether layer was separated and washed with brine. After evaporation of solvent, the residue (1.4 g) was used for the next reaction without purification.

Intermediate 21.4

[(2E)-2-methylhex-2-enyl]triphenylphosphonium bromide (Scheme 5)

Intermediate 21.3 (1.4 g, 7.33 mmol) and triphenylphosphine (2.30 g, 8.80 mmol) in toluene (15 mL) was refluxed for 2 hours. After cooling to room temperature, the solid was filtered and dried under vacuum. ¹HNMR (CD₃Cl): δ 0.79 (t, J=7.4 Hz, 3H), 1.09 (m, 4H), 1.66 (s, 3H), 1.88 (t, J=7.4 Hz, 2H), 4.72 (d, J=14 Hz, 2H), 5.30 (m, 1H), 7.67 (m, 15H).

Intermediate 21.5

Methyl 4-(2-{(2R)-2-[(1E/Z,3E)-3-methylocta-1,3-dienyl]-5-oxopyrrolidin-1-yl}ethyl)benzoate (Scheme 6)

To a suspension of Intermediate 21.3 (906.8 mg, 2 mmol) in dry THF (20 mL) at -78° C. was added n-BuLi (1.5 mL, 1.6 M in hexanes, 2.4 mmol). The resulting red colored mixture was stirred for 30 minutes and the Intermediate 1.4 (500 mg, 1.8 mmol) in THF 93 mL) was added. The mixture was stirred at -78° C. for 30 mixture and was warm to room temperature. The reaction was quenched with water (10 mL) and extracted with EtOAc (3×25 mL), washed with brine (3×10 mL). The organic layer was dried over MgSO₄, filtered and concentrated. The residue was used for the next reaction without purification (400 mg, 60%).

Examples 21 and 22

To a solution of Intermediate 21.4 (400 mg) in MeOH/THF (3/3 mL) was added NaOH (2.7 mL, 1.0 M, 2.7 mmol). The mixture was stirred for overnight. The product was purified through RP-HPLC using CAN/H₂O/TFA to afford the desired single compounds.

Example 21

4-(2-{(2R)-2-[(1Z,3E)-3-methylocta-1,3-dienyl]-5-oxopyrrolidin-1-yl}ethyl)benzoic acid The first isomer from RP-HPLC, ¹HNMR (CD₃OD): δ 0.920 (t, J=7.0 Hz, 3H), 1.37 (m, 4H), 1.72 (s, 3H), 2.15 (m, 2H), 2.60 (m, 3H), 2.73 (m, 1H), 2.86 (m, 1H), 3.19 (m, 1H), 3.65 (m, 1H), 3.91 (m, 1H), 5.12 (t, J=11.4 Hz, 1H), 5.29 (t, J=15.0, 1H), 6.13 (d, J=11.4 Hz, 1H), 7.14 (d, J=8.4 Hz, 2H), 7.87 (d, J=8.4 Hz, 2H), MS (m/z): 356.3 (M+H⁺).

Example 22

4-(2-{(2R)-2-[(1E,3E)-3-methylocta-1,3-dienyl]-5-oxopyrrolidin-1-yl}ethyl)benzoic acid The second isomer from RP-HPLC, $^1$HNMR (CD$_3$OD): δ 0.920 (t, J=7.0 Hz, 3H), 1.37 (m, 4H), 1.72 (s, 3H), 2.15 (m, 2H), 2.60 (m, 3H), 2.73 (m, 1H), 2.86 (m, 1H), 3.19 (m, 1H), 3.65 (m, 1H), 3.91 (m, 1H), 5.29 (dd, J=6.8 and 15.4 Hz, 1H), 5.54 (t, J=7.4, 1H), 6.19 (d, J=15.4 Hz, 1H), 7.17 (d, J=8.1 Hz, 2H), 7.87 (d, J=8.1 Hz, 2H), MS (m/z): 356.3 (M+H$^+$).

Example 23

Synthesis of 5-(3-{(2R)-2-[(1E,3E)-3-methylocta-1,3-dienyl]-5-oxopyrrolidin-1-yl}propyl)thiophene-2-carboxylic acid

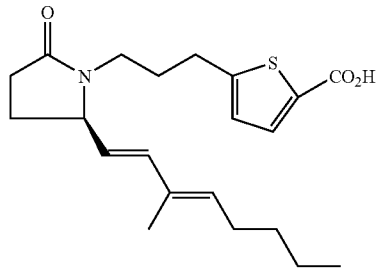

The title compound was prepared from methyl 5-[3-(2-(hydroxymethyl)-5-oxopyrrolidin-1-yl)propyl]thiophene-2-carboxylate (U.S. Pat. No. 6,498,172) and Intermediate 21.4 using the procedure for Examples 21 and 22.

Example 23

$^1$HNMR (CD$_3$OD): δ 0.912 (t, J=7.3 Hz, 3H), 1.26-1.38 (m, 6H), 1.73 (s, 3H), 1.90 (m, 2H), 2.04 (m, 1H), 2.42 (m, 2H), 2.82 (m, 2H), 3.03 (m, 1H), 3.45 (m, 1H), 4.17 (m, 1H), 5.40 (dd, J=8.3 and 15.4 Hz, 1H), 5.50 (t, J=7.3 Hz, 1H), 6.25 (d, J=15.4 Hz, 1H), 6.72 (d, J=3.7 Hz, 1H), 7.33 (d, J=3.7 Hz, 1H), MS (m/z): 376.3 (M+H$^+$).

Examples 24 and 25

Synthesis of 5-(3-{(2R)-2-[(1Z,3E)-methylocta-1,3-dienyl]-5-oxopyrrolidin-1-yl}propyl)-2-furoic acid and 5-(3-{(2R)-2-[(1E,3E)-3-methylocta-1,3-dienyl]-5-oxopyrrolidin-1-yl}propyl)-2-furoic acid

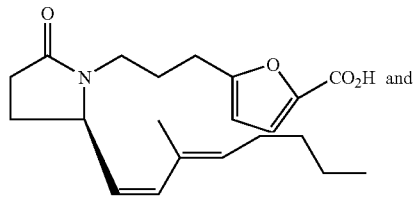

and

-continued

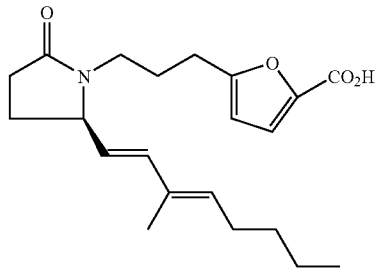

The title compounds were prepared form methyl 5-[3-(2-(hydroxymethyl)-5-oxopyrrolidin-1-yl)propyl]-2-furoate (prepared from (5R)-5-hydroxymethyl)pyrrolidin-2-one according to WO 0242268) and Intermediate 21.4 using the procedure for Examples 21 and 22.

Example 24

5-(3-{(2R)-2-[(1Z,3E)-3-methylocta-1,3-dienyl]-5-oxopyrrolidin-1-yl}propyl)-2-furoic acid The first isomer from RP-HPLC. $^1$HNMR (CD$_3$OD): δ 0.912 (t, J=7.3 Hz, 3H), 126-1.38 (m, 6H), 1.73 (s, 3H), 1.90 (m, 2H), 2.04 (m, 1H), 2.42 (m, 2H), 2.82 (m, 2H), 3.03 (m, 1H), 3.45 (m, 1H), 4.17 (m, 1H), 5.40 (t, J=11 Hz, 1H), 5.50 (t, J=7.3 Hz, 1H), 6.25 (d, J=15.4 Hz, 1H), 6.72 (d, J=3.7H, 1H), 7.33 (d, J=3.7 Hz, 1H), MS (m/z): 360.4 (M+H$^+$).

Example 25

5-(3-{(2R)-2-[(1E,3E)-3-methylocta-1,3-dienyl]-5-oxopyrrolidin-1-yl}propyl)-2-furoic acid The second isomer from RP-HPLC. $^1$HNMR (CD$_3$OD): δ 0.912 (t, J=7.3 Hz, 3H), 1.26-1.38 (m, 6H), 1.73 (s, 3H), 1.90 (m, 2H), 2.04 (m, 1H), 2.42 (m, 2H), 2.82 (m, 2H), 3.03 (m, 1H), 3.45 (m, 1H), 4.17 (m, 1H), 5.38 (dd, J=8.3 and 15.4 Hz, 1H), 5.52 (t, J=7.3 Hz, 1H), 6.25 (d, J=15.4 Hz, 1H), 6.72 (d, J=3.7H, 1H), 7.33 (d, J=3.7 Hz, 1H), MS (m/z): 360.4 (M+H).

Examples 26 and 27

Synthesis of 4-(2-{(2R)-2-[(1Z,3E)-6-cyclopropyl-4-methylhexa-1,3-dienyl]-5-oxopyrrolidin-1-yl}ethyl)benzoic acid and 4-(2-{(2R)-2-[(1E,3E)-6-cyclopropyl-4-methylhexa-1,3-dienyl]-5-oxopyrrolidin-1-yl}ethyl)benzoic acid

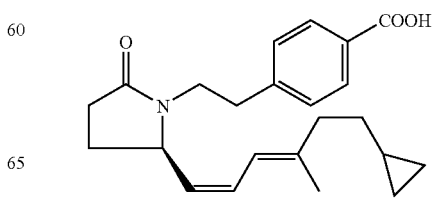

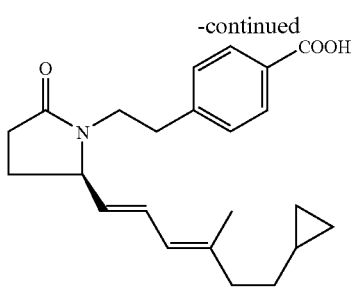

Intermediate 26.1

Methyl (2E)-5-cyclopropyl-3-(diethoxy-phosphoryloxy)-pent-2-enoate

To a suspension of 60% NaH in mineral oil (4.48 g, 112 mmol) in dry THF (200 mL) at 0° C. was added methyl acetoacetate dropwise. The mixture was stirred for 15 minutes. N-Butyl lithium (70 mL, 1.6 M in hexanes, 112 mmol) was added dropwise. The mixture was stirred at 0° C. for another 15 minutes. (Bromomethyl)cyclopropane (10.85 mL, 100 mmol) was added dropwise. The mixture was stirred for 1 hour at this temperature and warmed to room temperature and continued to stir for 2 hours at room temperature. Then the mixture was cooled to 0° C. again and diethylchlorophosphate was added dropwise. The mixture was stirred for 1 hour at 0° C. and warmed to room temperature and continued to stir for overnight. The mixture was quenched with water and separated organic layer. Organic layer was washed with water (3×10 mL) and brine (4×30 mL), dried over MgSO$_4$, concentrated. The residue was purified through flash column chromatography on silica (EtOAc:Hexanes=1:4) to afford 24 g of a colorless oil (78%).

(CCl$_3$D): δ 0.063(dt, J=1.5 and 4.8 Hz, 2H), 0.447 (dt, J=1.5 and 4.8 Hz, 2H), 0.705 (m, 1H), 1.36 (t, J=6.9 Hz, 6H), 1.51 (t, J=7.4 Hz, 2H), 2.53 (t, J=7.3 Hz, 2H), 3.68 (s, 3H), 4.27 (q, J=6.9 Hz, 4H), 5.36 (s, 1H).

Intermediate 26.2

Methyl 4-(2-{(2R)-2-[(1E/Z,3E)-6-cyclopropyl-4-methylhexa-1,3-dienyl]-5-oxopyrrolidin-1-yl}ethyl)benzoate To a suspension of 5-cyclopropyl-3-methyl-pent-2-enyl triphenylphosphonium bromide (1.4 g, 3.04 mmol), prepared from Intermediate 26.1, using the procedure for Intermediate 3.6 (Method B), in dry THF (20 mL) at −78° C. was added n-BuLi (2.84 mL, 1.6 M in hexanes, 4.55 mmol). The resulting red colored mixture was stirred for 30 minutes and Intermediate 1.4 (400 mg, 1.45 mmol) in THF (3 mL) was added. The mixture was stirred at −78° C. for 30 minutes and was warm to room temperature. The reaction was quenched with water (10 mL) and extracted with EtOAc (3×25 mL), washed with brine (3×10 mL). The organic layer was dried over MgSO$_4$, filtered and concentrated. The residue was used for the next reaction without purification (200 mg, 36%).

Examples 26 and 27

To a solution of Intermediate 26.2 (200 mg) in MeOH/THF (3/3 mL) was added NaOH (2.7 mL, 1.0 M, 2.7 mmol). The mixture was stirred for overnight. The product was purified through RP-HPLC using CAN/H$_2$O/TFA to afford the desired single compounds.

Example 26

4-(2-{(2R)-2-[(1Z,3E)-6-cyclopropyl-4-methylhexa-1,3-dienyl]-5-oxopyrrolidin-1-yl}ethyl)benzoic acid The first isomer from RP-HPLC. $^1$HNMR (CD$_3$OD): δ 0.024(dt, J=1.5 and 4.8 Hz, 2H), 0.39 (dt, J=1.5 and 4.8 Hz, 2H), 0.679 (m, 1H, 1.37 (m, 2H), 1.67 (m, 1H), 1.80 (s, 3H), 2.77 (m, 1H), 2.88 (m, 1H), 3.09 (m, 1H), 3.66 (m, 1H), 4.56 (m, 1H), 5.12 (t, J=10.7 Hz, 1H), 6.17 (d, J=11.3 Hz, 1H), 6.47 (t, J=11.3 Hz, 1H), 7.15 (d, J=8.4 Hz, 2H), 7.86 (d, J=8.4 Hz, 2H), MS (m/z): 368.4 (M+H$^+$).

Example 27

4-(2-{(2R)-2-[(1E,3E-6-cyclopropyl-4-methylhexa-1,3-dienyl]-5-oxopyrrolidin-1-yl}ethyl)benzoic acid The second isomer from RP-HPLC. $^1$HNMR (CD$_3$OD): δ 0.024 (dt, J=1.5 and 4.8 Hz, 2H), 0.39 (dt, J=1.5 and 4.8 Hz, 2H), 0.679 (m, 1H), 1.37 (m, 2H), 1.67 (m, 1H), 1.80 (s, 3H), 2.77 (m, 1H), 2.88 (m, 1H), 3.09 (m, 1H), 3.66 (m, 1H), 4.56 (m, 1H), 5.26 (dd, J=9.2 and 15 Hz, 1H), 5.87 (d, J=11 Hz, 1H), 6.38 (t, J=10.6 and 15 Hz, 1H), 7.17 (d, J=8.4Hz, 2H), 7.88 (d, J=8.4 Hz, 2H), MS (m/z): 368.4 (M+H$^+$).

Examples 28 and 29

Synthesis of 4-(2-{(2R)-2-[(1Z,3E)-4,7-dimethylocta-1,3-dienyl]-5-oxopyrrolidin-1-yl}ethyl)benzoic acid and 4-(2-{(2R)-2-[(1E,3E)-4,7-dimethylocta-1,3-dienyl]-5-oxopyrrolidin-1-yl}ethyl)benzoic acid

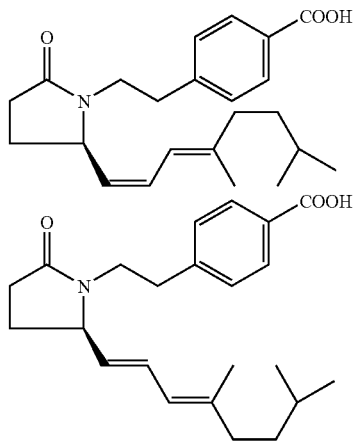

Intermediate 28.1

Methyl 4-(2-{(2R)-2-[(1E/Z,3E)-4,7-dimethylocta-1,3-dienyl]-5-oxopyrrolidin-1-yl}ethyl)benzoate.
(Scheme 6)

To a suspension of 3,6-dimethylhepta-2-enyl triphenylphosphonium bromide (460 mg, 0.985 mmol), prepared from methyl acetoacetate, using the procedure for Examples 26 and 27, in dry THF (20 mL) at −78° C. was added n-BuLi (1.23 mL, 1.6 M in hexanes, 1.97 mmol). The resulting red colored mixture was stirred for 30 minutes and Intermediate 1.4 (400 mg, 1.45 mmol) in THF (3 mL) was added. The mixture was stirred at −78° C. for 30 minutes and was warm to room temperature. The reaction was quenched with water (10 mL) and extracted with EtOAc (3×25 mL), washed with brine (3×10 mL). The organic layer was dried over MgSO$_4$, filtered and concentrated. The residue was used for the next reaction without purification (200 mg, 53%).

Examples 28 and 29

To a solution of Intermediate 28.1 (200 mg) in MeOH/THF (3/3 mL) was added NaOH (2.7 mL, 1.0 M, 2.7 mmol). The mixture was stirred for overnight. The product was purified through RP-HPLC using CAN/H$_2$O/TFA to afford the desired single compounds.

Example 28

4-(2-{(2R)-2-[(1Z,3E)-4,7-dimethylocta-1,3-dienyl]-5-oxopyrrolidin-1-yl}ethyl)benzoic acid The first isomer from RP-HPLC. $^1$HNMR (CD$_3$OD): δ 0.909 (d, J=6.4 Hz, 5H), 1.33 (m, 2H), 1.5-1.7 (m, 3H), 1.80 (s, 3H), 2.16 (m, 2H), 2.36 (m, 2H), 2.78 (m, 1H), 2.88 (m, 1H), 3.09 (m, 1H), 3.67 (m, 1H), 4.63 (m, 1H), 5.07 (t, J=10.6 Hz, 1H), 6.17 (d, J=11.3 Hz, 1H), 6.47 (t, J=11.3 Hz, 1H), 7.15 (d, J=8.4 Hz, 2H), 7.86 (d, J=8.4 Hz, 2H), MS (m/z): 370.3 (M+H$^+$).

Example 29

4-(2-{(2R)-2-[(1E,3E)-4,7-dimethylocta-1,3-dienyl]-5-oxopyrrolidin-1-yl}ethyl)benzoic acid The second isomer from RP-HPLC. $^1$HNMR (CD$_3$OD): δ 0.909 (d, J=6.3 Hz, 5H), 1.33 (m, 2H), 1.5-1.7 (m, 3H), 1.80 (s, 3H), 2.16 (m, 2H), 2.36 (m, 2H), 2.78 (m, 1H), 2.88 (m, 1H), 3.09 (m, 1H), 3.67 (m, 1H), 4.63 (m, 1H), 5.29 (dd, J=9.2 and 15 Hz, 1H), 5.89 (d, J=10.7 Hz, 1H), 6.39 (dd, J=11 and 15 Hz, 1H), 7.18 (d, J=8.4 Hz, 2H), 7.88 (d, J=8.4 Hz, 2H), MS (m/z): 370.3 (M+H$^+$).

Examples 30 and 31

Synthesis of: 4-(2-{(2R)-2-[(1Z,3E)-5-cyclopentyl-4-methylpenta-1,3-dienyl]-5-oxopyrrolidin-1-yl}ethyl)benzoic acid and 4-(2-{(2R)-2-[1E,3E)-5-cyclopentyl-4-methylpenta-1,3-dienyl]-5-oxopyrrolidin-1-yl}ethyl)benzoic acid

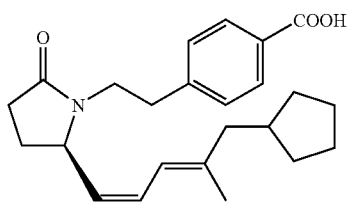

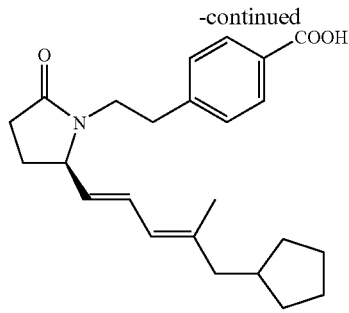

Intermediate 30.1 methyl (2E)-4-cyclopentyl-3-methylbut-2-enoate. (Scheme 6)

To a suspension of sodium hydride (956 mg, 60% in oil, 23.9 mmol) in THF (60 mL) cooled at 0° C. was added dropwise trimethyl phosphonoacetate (3.87 mL, 4.35 g, 23.9 mmol). The mixture was stirred for 20 mn at 0° C. and cyclopentylacetone (2.22 mL, 2.00 g, 15.9 mmol) was added dropwise. The solution was warmed to 25° C., then refluxed for 2 h, and poured in a solution of brine (100 mL). The reaction mixture was extracted with ethyl acetate (2×50 mL) and the combined organic phase was dried over sodium sulfate and concentrated to give the ester (2.87 g, 99%) as a mixture of E and Z isomers 3:1. MS (m/z) 182 (M).

Examples 30 and 31

The title compounds were synthesized from Intermediate 1.4 and Intermediate 30.1 using procedure described for Example 3 (Method B).

Example 30

4-(2-{(2)-2-[(1Z,3E)-5-cyclopentyl-4-methylpenta-1,3-dienyl]-5-oxopyrrolidin-1-yl}ethyl)benzoic acid (first isomer in HPLC: ACN/H$_2$O/TFA):

$^1$H NMR (CD$_3$OD) δ 1.07-1.20 (m, 2H), 1.49-1.73 (m, 7H), 1.79 (s, 3H), 2.00-2.25 (m, 4H), 2.29-2.45 (m, 2H), 2.75-2.83 (m, 1H), 2.87-2.95 (m, 1H), 3.07-3.15 (m, 1H), 3.65-3.73 (m, 1H), 4.50-4.56 (m, 1H), 5.11 (t, J=10.6 Hz, 1H), 6.05 (d, J=11.7 Hz, 1H), 6.47 (t, J=11.4 Hz, 1H), 7.22 (d, J=8.1 Hz, 2H), 7.91 (d, J=8.0 Hz, 2H); MS (m/z) 382 (M+1).

Example 31

4-(2-{(2R)-2-[(1E,3E)-5-cyclopentyl-4-methylpenta-1,3-dienyl]-5-oxopyrrolidin-1-yl}ethyl)benzoic acid (second isomer in HPLC): ACN/H$_2$O/TFA:

$^1$H NMR (CD$_3$OD) δ 1.08-1.19 (m, 2H), 1.51-1.74 (m, 7H), 1.78 (s, 3H), 2.02-2.20 (m, 4H), 2.25-2.42 (m, 2H), 2.73-2.81 (m, 1H), 2.85-2.93 (m, 1H), 3.14-3.22 (m, 1H), 3.60-3.68 (m, 1H), 3.90-3.96 (m, 1H), 5.25 (dd, J=15.0, 9.2 Hz, 1H), 5.83 (d, J=11.0 Hz, 1H), 6.39 (dd, J=15.0, 11.0 Hz, 1H), 7.17 (d, J=8.1 Hz, 2H), 7.87 (d, J=8.1 Hz, 2H); MS (m/z) 382 (M+1).

Examples 32 and 33

Synthesis of 4-(2-{(2R)-2-[(1Z,3E)-4-phenylpenta-1,3-dienyl]-5-oxopyrrolidin-1-yl}ethyl)benzoic acid and 4-(2-{(2R)-2-[(1E,3E)-4-phenylpenta-1,3-dienyl]-5-oxopyrrolidin-1-yl}ethyl)benzoic acid

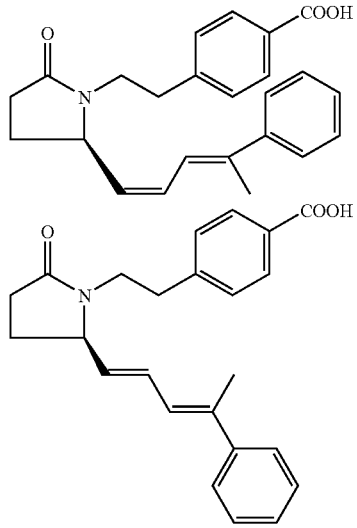

Intermediate 32.1

Methyl 4-(2-{(2R)-2-[(1E/Z,3E)-4-methylhexa-1,3-dienyl]-5-oxopyrrolidin-1-yl}ethyl)benzoate. (Scheme 6)

To a suspension of (2E)-3-phenylbut-2-enyl triphenylphosphonium bromide (893 mg, 1.89 mmol), prepared from ethyl benzoylacetate, using the procedure for Intermediate 3.6 (Method B), in dry THF (20 mL) at −78° C. was added n-BuLi (2.27 mL, 1.6 M in hexanes, 3.26 mmol). The resulting red colored mixture was stirred for 30 minutes and Intermediate 1.4 (400 mg, 1.45 mmol) in THF (3 mL) was added. The mixture was stirred at −78° C. for 30 minutes and was warm to room temperature. The reaction was quenched with water (10 mL) and extracted with EtOAc (3×25 mL), washed with brine (3×10 mL). The organic layer was dried over MgSO$_4$, filtered and concentrated. The residue was used for the next reaction without purification (400 mg).

Examples 32 and 33

To a solution of Intermediate 32.1 (400 mg) in MeOH/THF (3/3 mL) was added NaOH (3.5 mL, 1.0 M, 3.5 mmol). The mixture was stirred for overnight. The product was purified through RP-HPLC using CAN/H$_2$O/TFA to afford the desired single compounds.

Example 32

4-(2-{(2R)-2-[(1Z,3E)-4-phenylpenta-1,3-dienyl]-5-oxopyrrolidin-1-yl}ethyl)benzoic acid The first isomer from RP-HPLC.
$^1$HNMR (CD$_3$OD): δ 1.71 (m, 1H), 2.21 (s, 3H), 2.40 (m, 2H), 2.80 (m, 1H), 2.88 (m, 1H), 3.11 (m, 1H), 3.69 (m, 1H), 4.68 (m, 1H), 5.10 (t, J=9.4 Hz, 1H), 6.71 (m, 2H), 7.11 (d, J=8.1 Hz, 2H), 7.27 (d, J=7.4 Hz, 1H), 7.34 (t, J=7.4 Hz, 2H), 7.47 (d, J=7.4 Hz, 2H), 7.82 (d, J=8.1 Hz, 2H), MS (m/z): 376.4 (M+H$^+$).

Example 33

4-(2-{(2R)-2-[(1E,3E)-4-phenylpenta-1,3-dienyl]-5-oxopyrrolidin-1-yl}ethyl)benzoic acid The second isomer from RP-HPLC.
$^1$HNMR (CD$_3$OD): δ 1.74 (m, 1H), 2.18 (s, 3H), 235 (m, 2H), 2.80 (m, 1H), 2.88 (m, 1H), 3.11 (m, 1H), 3.69 (m, 1H), 4.68 (m, 1H), 5.32 (dd, J=9.2 and 14.7 Hz, 1H), 6.47 (d, J=11 Hz, 1H), 6.54 (dd, J=11 and 14.7 Hz, 1H) 7.19 (d, J=8.1 Hz, 2H), 7.21 (d, J=7.4 Hz, 1H), 7.31 (t, J=7.4 Hz, 2H), 7.47 (d, J=7.4 Hz, 2H), 7.82 (d, J=8.1 Hz, 2H), MS (m/z): 376.4 (M+H$^+$).

Examples 34 and 35

Synthesis of 4-(2-{(2R)-2-[(1Z,3Z)-4-phenylpenta-1,3-dienyl]-5-oxopyrrolidin-1-yl}ethyl)benzoic acid and 4-(2-{(2R)-2-[(1E,3Z)-4-phenylpenta-1,3-dienyl]-5-oxopyrrolidin-1-yl}ethyl)benzoic acid

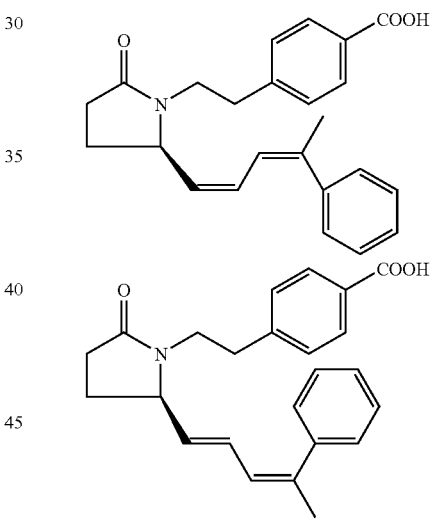

Intermediate 34.1

3-(diethoxyphosphoryloxy)-3-pheny-(2E)acrylic acid ethyl ester

To a solution of ethyl benzoylacetate (10 g, 52.03 mmol) was added DMAP (699.2 mg, 5.72 mmol), HMPA (9.96 mL, 57.23 mmol), TEA (7.98 mL, 57.23 mmol). The resulting yellow solution was stirred at 0° C. for 30 minutes and then coiled to −20° C. Diethyl chlorophosphate was added dropwise to the cooled solution and a heavy precipitate began to form immediately. The yellow-orange paste was warmed to room temperature and stirred for another 4 hours. The reaction mixture was diluted with ether and acidified with 1N HCl. The ethereal extracts were washed with saturated aqueous CuSO$_4$ to remove HMPA, dried over MgSO$_4$, and concentrated. The residue was purified through flash column chromatography on silica gel (EtOAc:hexanes=2:3) to give 11.6 g in 68% yield.

$^1$HNMR (CDCl$_3$): δ 1.15 (t, J=6.6 Hz, 3H), 1.30 (t, J=8.2 Hz, 6H), 4.22 (m, 6H), 6.12 (s, 1H), 7.39 (m, 3H), 7.51 (m, 2H).

Intermediate 34.2

Methyl 4-(2-{(2R)-2-[(1E/Z,3Z)-4-methylhexa-1,3-dienyl]-5-oxopyrrolidin-1-yl}ethyl)benzoate. (Scheme 6)

To a suspension of (2Z)-3-phenylbut-2-enyl triphenylphosphonium bromide (473 mg, 1.0 mmol), prepared from Intermediate 34.1 using the procedure for Intermediate 3.6, in dry THF (20 mL) at −78° C. was added n-BuLi (1.38 mL, 1.6 M in hexanes, 2.2 mmol). The resulting red colored mixture was stirred for 30 minutes and the aldehyde (275 mg, 1.0 mmol) in THF (3 mL) was added. The mixture was stirred at −78° C. for 30 minutes and was warm to room temperature. The reaction was quenched with water (10 mL) and extracted with EtOAc (3×25 mL), washed with brine (3×10 mL). The organic layer was dried over MgSO$_4$, filtered and concentrated. The residue was used for the next reaction without purification (150 mg).

Examples 34 and 35

To a solution of Intermediate 34.1 (150 mg) in MeOH/THF (3/3 mL) was added NaOH (3.5 mL, 1.0 M, 3.5 mmol). The mixture was stirred for overnight. The product was purified through RP-HPLC using CAN/H$_2$O/TFA to afford the desired single compounds.

Example 34

4-(2-{(2R)-2-[(1Z,3Z)-4-phenylpenta-1,3-dienyl]-5-oxopyrrolidin-1-yl}ethyl)benzoic acid The first isomer from RP-HPLC.

$^1$HNMR (CD$_3$OD): δ 1.68 (m, 1H), 2.21 (s, 3H), 2.20-2.40 (m, 2H), 2.81 (m, 1H), 2.88 (m, 1H), 3.11 (m, 1H), 3.69 (m, 1H), 4.68 (m, 1H), 5.10 (dd, J=9.0 and 12.9 Hz, 1H), 6.71 (m, 2H), 7.11 (d, J=8.1 Hz, 2H), 7.27 (d, J=7.4 Hz, 1H), 7.34 (t, J=7.4 Hz, 2H), 7.47 (d, J=7.4 Hz, 2H), 7.82 (d, J=8.1 Hz, 2H), MS (m/z): 376.4 (M+H$^+$).

Example 35

4-(2-{(2R)-2-[(1E,3E)-4-phenylpenta-1,3-dienyl]-5-oxopyrrolidin-1-yl}ethyl)benzoic acid The second isomer from RP-HPLC.

$^1$HNMR (CD$_3$OD): δ 1.74 (m, 1H), 2.18 (s, 3H), 2.35 (m, 2H), 2.80 (m, 1H), 2.88 (m, 1H), 3.11 (m, 1H), 3.69 (m, 1H), 4.68 (m, 1H), 5.51 (dd, J=8.8 and 14.6 Hz, 1H), 6.52 (d, J=10.3 Hz, 1H), 6.51 (dd, J=10.3 and 14.6 Hz, 1H) 7.19 (d, J=8.1 Hz, 2H), 7.21 (d, J=7.4 Hz, 1H), 7.31 (t, J=7.4 Hz, 2H), 7.47 (d, J=7.4 Hz, 2H), 7.82 (d, J=8.1 Hz, 2H), MS (m/z): 376.4 (M+H$^+$).

Examples 36 and 37

Synthesis of 5-(3-{(2R)-2-[(1Z,3E)-octa-1,3-dienyl]-5-oxopyrrolidin-1-yl}propyl)-2-furoic acid and 5-(3-{(2R)-2-[(1E,3E)-octa-1,3-dienyl]-5-oxopyrrolidin-1-yl}propyl)-2-furoic acid

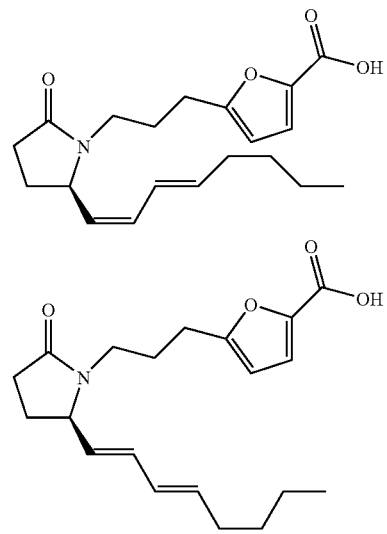

The title compound was prepared from methyl 5-{3-[(2R)-2-(hydroxymethyl)-5-oxopyrrolidin-1-yl]propyl}-2-furoate (prepared from (5R)-5-(hydroxymethyl)pyrrolidin-2-one according to WO 0242268) and (E)-2-heptenyltriphenyl phosphonium bromide (Watanabe et al., 1989) using the procedure of Examples 13 and 14.

Example 36

5-(3-{(2R)-2-[(1Z,3E)-octa-1,3-dienyl]-5-oxopyrrolidin-1-yl}propyl)-2-furoic acid $^1$HNMR (CD$_3$OD) δ 0.90 (t, J=7.0 Hz, 3H), 1.25~1.45 (m, 4H), 1.65~1.75 (m, 1H), 1.85~1.96 (m, 2H), 2.10~2.45 (m, 5H), 2.65 (t, J=7.7 Hz, 2H), 2.95~3.05 (m, 1H), 3.45~3.55 (m, 1H), 4.68~4.75 (m, 1H), 5.12 (t, J=10 Hz, 1H), 5.78~5.87 (m, 1H), 6.10 (d, J=3.3 Hz, 1H), 6.19 (t, J=11 Hz, 1H), 6.40~6.50 (m, 1H), 6.83 (d, J=3.3 Hz, 1H). MS (m/z) 346.3 (M+H).

Example 37

5-(3-{(2R)-2-[(1E,3E)-octa-1,3-dienyl]-5-oxopyrrolidin-1-yl}propyl)-2-furoic acid $^1$HNMR (CD$_3$OD) δ 0.90 (t, J=7.3 Hz, 3H), 1.28~1.42 (m, 4H), 1.68~1.78 (m, 1H), 1.82~1.96 (m, 2H), 2.06~2.42 (m, 5H), 2.63 (t, J=7.3 Hz, 2H), 2.95~3.02 (m, 1H), 3.48~3.58 (m, 1H), 4.12~4.20 (m, 1H), 5.38 (dd, J=8.8, 15 Hz, 1H), 5.72~5.80 (m, 1H), 6.02~6.08 (m, 1H), 6.09 (d, J=3.3 Hz, 1H), 6.24 (dd, J=11, 15 Hz, 1H), 6.80 (d, J=3.3 Hz, 1H). MS (m/z) 346.3 (M+M).

Examples 38 and 39

Synthesis of 4-(3-{(2R)-Z-[(1Z,3E)-octa-1,3-dienyl]-5-oxopyrrolidin-1-yl}propyl)benzoic acid and 4-(3-{(2R)-2-[(1E,3E)-octa-1,3-dienyl]-5-oxopyrrolidin-1-yl}propyl)benzoic acid

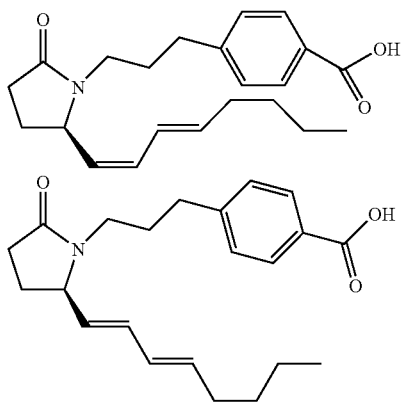

The title compound was prepared from methyl 4-{3-[(2R)-2-(hydroxymethyl)-5-oxopyrrolidin-1-yl]propyl}benzoate (prepared from (5R)-5-(hydroxymethyl)pyrrolidin-2-one according to WO 0242268) and (E)-2-heptenyltriphenyl phosphonium bromide (Watanabe et al., 1989) using the procedure of Examples 13 and 14.

Example 38

4-(3-{(2R)-2-[(1Z,3E)-octa-1,3-dienyl]-5-oxopyrrolidin-1-yl}propyl)benzoic acid $^1$HNMR (CD$_3$OD) δ 0.90 (t, J=7.0 Hz, 3H), 1.28~1.45 (m, 4H), 1.60~1.90 (m, 3H), 2.10~2.45 (m, 5H), 2.62 (t, J=7.7 Hz, 2H), 2.88~2.98 (m, 1H), 3.48~3.58 (m, 1H), 4.65~4.75 (m, 1H), 5.12 (t, J=10 Hz, 1H), 5.78~5.88 (m, 1H), 6.19 (t, J=11 Hz, 1H), 6.38~6.48 (m, 1H), 7.18 (d, J=8.1 Hz, 2H), 7.86 (d, J=8.1 Hz, 1H). MS (m/z) 356.2 (M+H).

Example 39

4-(3-{(2R)-2-[(1E,3E)-octa-1,3-dienyl]-5-oxopyrrolidin-1-yl}propyl)benzoic acid $^1$HNMR (CD$_3$OD) δ 0.90 (t, J=7.0 Hz, 3H), 1.28~1.45 (m, 4H), 1.60~1.90 (m, 3H), 2.10~2.45 (m, 5H), 2.61 (t, J=7.7 Hz, 2H), 2.95~3.04 (m, 1H), 3.42~3.52 (m, 1H), 4.06~4.15 (m, 1H), 5.39 (dd, J=9.2, 15 Hz, 1H), 5.70~5.80 (m, 1H), 6.04 (dd, J=10, 15 Hz, 1H), 6.18 (dd, J=10, 15 Hz, 1H), 7.17 (d, J=8.1 Hz, 2H), 7.85 (d, J=8.1 Hz, 1H). MS (m/z) 356.2 (M+H).

Examples 40 and 41

Synthesis of 4-(2-{(2R)-2-[(1Z,3Z)-3-fluoro-4-methylocta-1,3-dienyl]-5-oxopyrrolidin-1-yl}ethyl)benzoic acid and 4-(2-{(2R)-2-[(1E,3Z)-3-fluoro-4-methylocta-1,3-dienyl]-5-oxopyrrolidin-1-yl}ethyl)benzoic acid

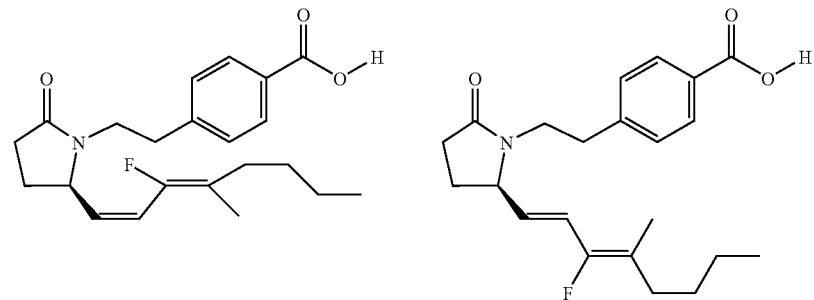

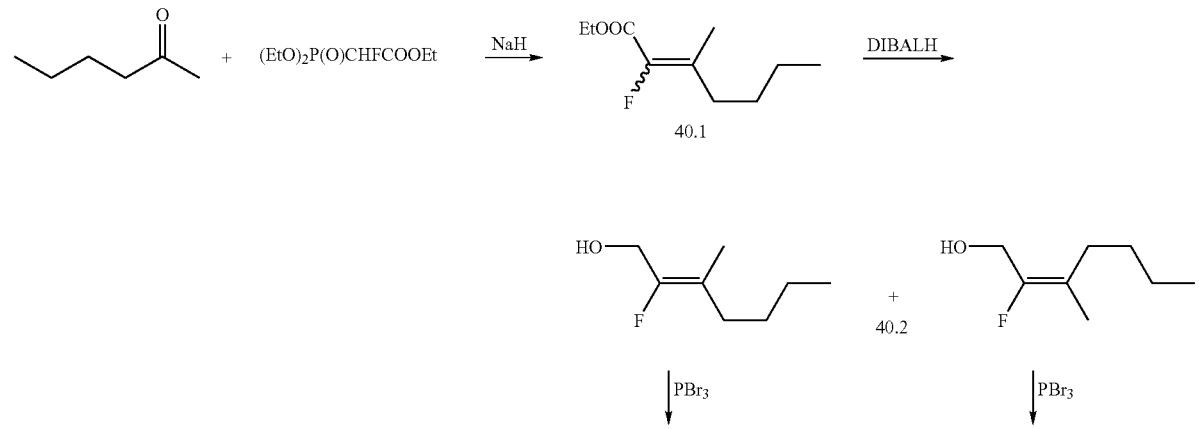

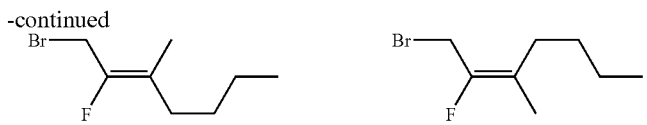
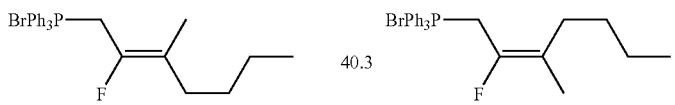
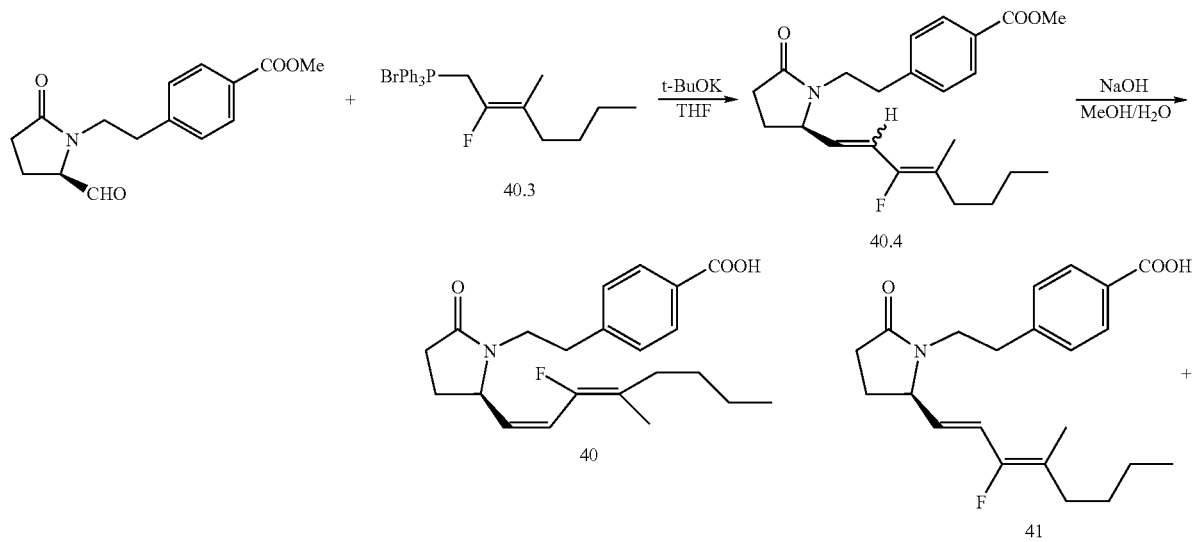

Intermediate 40.1 ethyl 2-fluoro-3-methylhept-2-enoate

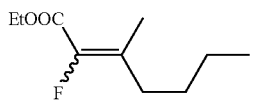

To a suspension of NaH (1.9 g, 60% in mineral oil, 48 mmol) in THF (60 mL) at 0° C. was added triethyl 2-fluoro-2-phosphonacetate (15 g, 62 mmol) in THF (60 mL) under Ar. The reaction mixture was stirred for 1 hr. A solution of 2-hexanone (4.14 g, 41 mmol) in THF (40 mL) was added dropwise and stirring was continued for another 1 hr. The mixture was refluxed for 2 hr. after which it was cooled to rt overnight. A mixture of ether and 0.5 N HCl (200 mL, 1:1) was added. After separation, the aqueous phase was extracted with ether (2×100 mL), the combined organic phase was washed with 0.5 N HCl (100 mL), saturated aqueous NaHCO₃ (100 mL), brine (100 mL), dried, concentrated, the crude product was used directly for next step.

Intermediate 40.2

(2Z)-2-fluoro-3-methylhept-2-en-1-ol

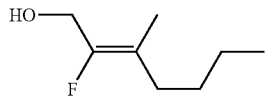

Crude intermediate 40.1 was reduced with DIBALH according to the procedure of intermediate 3.4. The (Z) isomer intermediate was isolated after column purification. ¹HNMR (CDCl₃) δ 0.89 (t, J=7.1 Hz, 3H), 1.20~1.45 (m, 4H), 1.64 (d, J=2.9 Hz, 3H), 2.09 (dt, J=2.6, 7.3 Hz, 2H), 4.22 (dd, J=6.2, 23 Hz, 2H).

Intermediate 40.3

(2Z)-2-fluoro-3-methylhept-2-enyltriphenylphosphonium bromide (Scheme 5)

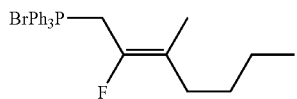

The title intermediate was synthesized from Intermediate 40.2 according to procedure of Intermediate 5.1. ¹HNMR (CDCl₃) δ 0.80 (m, 3H), 1.09~1.20 (m, 4H), 1.35~1.45 (m, 3H), 1.90~2.00 (m, 2H), 5.08 (dd, J=14, 21 Hz, 2H), 7.65~7.90 (m, 15H).

Intermediate 40.4 methyl 4-(2-{(2R)-2-[(3Z)-3-fluoro-4-methylocta-1,3-dienyl]-5-oxopyrrolidin-1-yl}ethyl)benzoate (Scheme 6)

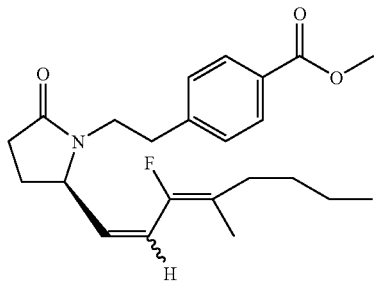

A suspension of Intermediate 40.3 (344 mg, 0.73 mmol) in THF (10 mL) was stirred at rt for 0.5 hr to form an evenly distributed slurry. This mixture was cooled to −78° C. and stirred for 0.5 hr under Ar. A solution of t-BuOK in THF (0.80 mL of 1.0 M, 0.80 mmol) was added dropwise under Ar at −78° C. The mixture was stirred for 0.5 hr at −78° C. A solution of Intermediate 1.4 (200 mg, 0.73 mmol) in THF was added dropwise under Ar at −78° C. After stirred for 1 hr at this temperature, the mixture was allowed to warm to 0° C. and stirred overnight at 4° C. The reaction was quenched with water (6 mL) at rt and concentrated. The aqueous phase was extracted with EtOAc (3×30 mL). The combined organic phase was washed with brine, dried (Na₂SO₄), concentrated. The crude (1Z),(1E) mixture was obtained after a short column (silica gel), and was used directly for next step after concentration.

Examples 40 and 41

The title compound was prepared from Intermediate 40.4 using the procedure of Examples 5 and 6.

Example 40

4-(2-{(2R)-2-[(1Z,3Z)-3-fluoro-4-methylocta-1,3-dienyl]-5-oxopyrrolidin-1-yl}ethyl)benzoic acid ¹HNMR (CD₃OD) δ 0.92 (t, J=7.3 Hz, 3H), 1.20~1.42 (m, 4H), 1.73 (s, 3H), 2.10~2.40 (m, 5H), 2.70~2.80 (m, 2H), 3.05~3.18 (m, 1H), 3.60~3.75 (m, 1H), 3.90~4.00 (m, 1H), 5.61 (dd, J=6.3, 9.1 Hz, 1H), 6.30 (dd, J=15, 28 Hz, 1H), 7.18 (d, J=8.4 Hz, 2H), 7.87 (d, J=8.4 Hz, 2H).

Example 41

4-(2-{(2R)-2-[(1E,3Z)-3-fluoro-4-methylocta-1,3-dienyl]-5-oxopyrrolidin-1-yl}ethyl)benzoic acid ¹HNMR (CD₃OD) δ 0.92 (t, J=7.3 Hz, 3H), 1.20~1.42 (m, 4H), 1.73 (m, 3H), 2.10~2.20 (m, 3H), 2.20~2.40 (m, 2H), 2.70~2.80 (m, 2H), 3.05~3.18 (m, 1H), 3.60~3.75 (m, 1H), 3.90~4.00 (m, 1H), 4.80~5.20 (m, 2H), 7.19 (d, J=8.4 Hz, 2H), 7.86 (d, J=8.4 Hz, 2H). MS (m/z) 374.4 (M+H).

Examples 42 and 43

Synthesis of 4-(2-{(2R)-2-[(1Z,3E)-3-fluoro-4-methylocta-1,3-dienyl]-5-oxopyrrolidin-1-yl}ethyl)benzoic acid and 4-(2-{(2R)-2[(1E,3E)-3-fluoro-4-methylocta-1,3-dienyl]-5-oxopyrrolidin-1-yl}ethyl)benzoic acid

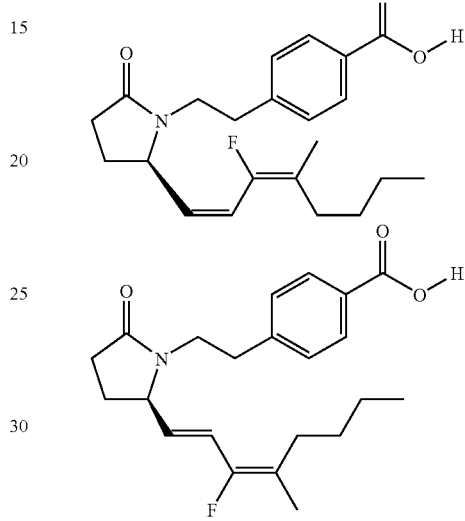

Intermediate 42.1

(2E)-2-fluoro-3-methylhept-2-en-1-ol

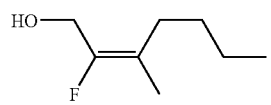

This intermediate was also isolated during the purification of Intermediate 40.2. ¹HNMR (CDCl₃) δ 0.89 (t, J=7.1 Hz, 3H), 1.20~1.45 (m, 4H), 1.66 (d, J=3.7 Hz, 3H), 2.00 (dt, J=1.1, 7.7 Hz, 2H), 4.22 (dd, J=6.2, 23 Hz, 2H).

Examples 42 and 43

The title compound was prepared from Intermediate 1.4 and Intermediate 42.1 using the procedure of Examples 40 and 41.

Example 42

4-(2-{(2R)-2-[(1Z,3E)-3-fluoro-4-methylocta-1,3-dienyl]-5-oxopyrrolidin-1-yl}ethyl)benzoic acid ¹HNMR (CD₃OD) δ 0.90 (t, J=7.3 Hz, 3H), 1.20~1.42 (m, 4H), 1.73 (s, 3H), 2.10~2.40 (m, 5H), 2.70~2.80 (m, 2H), 3.05~3.18 (m, 1H), 3.60~3.75 (m, 1H), 3.90~4.00 (m, 1H), 5.61 (dd, J=6.3, 9.1 Hz, 1H), 6.30 (dd, J=15, 28 Hz, 1H), 7.18 (d, J=8.4 Hz, 2H), 7.87 (d, J=8.4 Hz, 2H).

Example 43

4-(2-{(2R)-2-[(1E,3E)-3-fluoro-4-methylocta-1,3-dienyl]-5-oxopyrrolidin-1-yl}ethyl)benzoic acid ¹HNMR (CD₃OD) δ 0.92 (t, J=7.3 Hz, 3H), 1.20~1.42 (m, 4H), 1.73 (s, 3H), 2.10~2.40 (m, 5H), 2.70~2.80 (m, 2H), 3.05~3.18 (m, 1H), 3.60~3.75 (m, 1H), 3.90~4.00 (m, 1H), 5.61 (dd, J=6.3, 9.1 Hz, 1H), 6.30 (dd, J=15, 28 Hz, 1H), 7.18 (d, J=8.4 Hz, 2H), 7.87 (d, J=8.4 Hz, 2H).

Examples 44 and 45

Synthesis of: 4-(2-{(2R)-2-[(1Z,3E)-4-methylhepta-1,3-dienyl]-5-oxopyrrolidin-1-yl}ethyl)benzoic acid and 4-(2-{(2R)-2-[(1E,3E)-4-methylhepta-1,3-dienyl]-5-oxopyrrolidin-1-yl}ethyl)benzoic acid

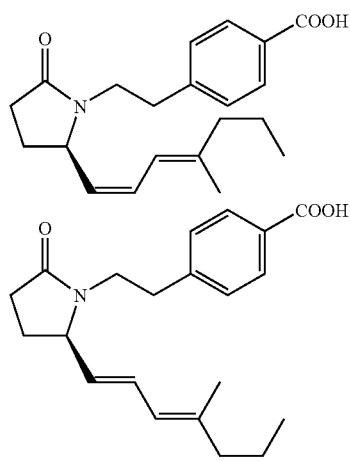

The title compound was synthesized from Intermediate 1.4 and methyl 3-oxohexanoate following the procedure described for Example 26.

Example 44

4-(2-{(2R)-2-[(1Z,3E)-4-methylhepta-1,3-dienyl]-5-oxopyrrolidin-1-yl}ethyl)benzoic acid (first isomer in HPLC ACN/H₂O/TFA): ¹H NMR (CD₃OD) δ 0.91 (t, J=7.3 Hz, 3H), 1.49 (hex, J=7.3 Hz, 2H), 1.61-1.71 (m, 1H), 1.78 (s, 3H), 2.11 (t, J=7.7 Hz, 2H), 2.15-2.24 (m, 1H), 2.29-2.44 (m, 2H), 2.74-2.82 (m, 1H), 2.86-2.93 (m, 1H), 3.06-3.13 (m, 1H), 3.64-3.72 (m, 1H), 4.48-4.55 (m, 1H), 5.10 (t, J=10.6 Hz, 1H), 6.06 (d, J=11.8 Hz, 1H), 6.47 (t, J=11.7 Hz, 1H), 7.19 (d, J=6.9 Hz, 2H), 7.88 (d, J=7.7 Hz, 2H); MS (m/z) 364 (M+23).

Example 45

4-(2-{(2R)-2-[(1E,3E)-4-methylhepta-1,3-dienyl]-5-oxopyrrolidin-1-yl}ethyl)benzoic acid (second isomer in HPLC ACN/H₂O/TFA): ¹H NMR (CD₃OD) δ 0.90 (t, J=7.3 Hz, 3H), 1.48 (hex, J=7.3 Hz, 2H), 1.63-1.73 (m, 1H), 1.77 (s, 3H), 2.06 (t, J=7.3 Hz, 2H), 2.10-2.20 (m, 1H), 2.26-2.41 (m, 2H), 2.74-2.81 (m, 1H), 2.85-2.92 (m, 1H), 3.13-3.22 (m, 1H), 3.61-3.69 (m, 1H), 3.89-3.95 (m, 1H), 5.25 (dd, J=15.0, 9.1 Hz, 1H), 5.83 (d, J=10.6 Hz, 1H), 6.39 (dd, J=15.0, 11.0 Hz, 1H), 7.17 (d, J=8.1 Hz, 2H), 7.87 (d, J=8.0 Hz, 2E1); MS (m/z) 364 (M+23).

Examples 46 and 47

Synthesis of 4-(2-{(2R)-2-[(1Z,3E)-4-methylhexa-1,3-dienyl]-5-oxopyrrolidin-1-yl}ethyl)benzoic acid and 4-(2-{(2R)-2-[(1E,3E)-4-methylhexa-1,3-dienyl]-5-oxopyrrolidin-1-yl}ethyl)benzoic acid

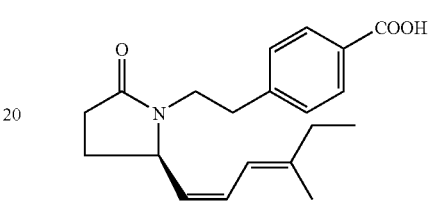

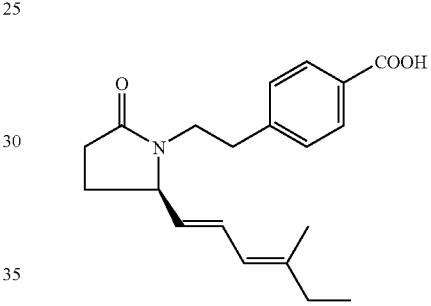

Intermediate 46.1

Methyl 4-(2-{(2R)-2-[(1E/Z,3E)-4-methylhexa-1,3-dienyl]-5-oxopyrrolidin-1-yl}ethyl)benzoate
(Scheme 6)

To a suspension of 3-dimethylpent-2-enyl triphenylphosphonium bromide (803 mg, 1.89 mmol), prepared from butan-2-one, using the procedure for Examples 30 and 31, in dry THF (20 mL) at −78° C. was added n-BuLi (2.27 mL, 1.6 M in hexanes, 3.26 mmol). The resulting red colored mixture was stirred for 30 minutes and Intermediate 1.4 (400 mg, 1.45 mmol) in THF (3 mL) was added. The mixture was stirred at −78° C. for 30 minutes and was warm to room temperature. The reaction was quenched with water (10 mL) and extracted with EtOAc (3×25 mL), washed with brine (3×10 mL). The organic layer was dried over MgSO₄, filtered and concentrated. The residue was used for the next reaction without purification (470 mg, 95%).

Examples 46 and 47

To a solution of Intermediate 30.1 (470 mg) in MeOH/THF (3/3 mL) was added NaOH (3.5 mL, 1.0 M, 3.5 mmol). The mixture was stirred for overnight. The product was purified through RP-HPLC using CAN/H₂O/TFA to afford the desired single compounds.

Example 46

4-(2-{(2R)-2-[(1Z,3E)-4-methylhexa-1,3-dienyl]-5-oxopyrrolidin-1-yl}ethyl)benzoic acid The first isomer from RP-HPLC.

$^1$HNMR (CD$_3$OD): δ 1.084 (t, J=7.3 Hz, 2H), 1.78 (q, J=7.3 Hz, 2H), 1.84 (s, 3H), 2.14 (m, 3H), 2.36 (m, 2H), 2.78 (m, 1H), 2.88 (m, 1H), 3.09 (m, 1H), 3.67 (m, 1H), 4.54 (m, 1H), 5.10 (t, J=10.3 Hz, 1H), 6.09 (d, J=11.4 Hz, 1H), 6.47 (t, J=10.3 Hz, 1H), 7.15 (d, J=8.4 Hz, 2H), 7.86 (d, J=8.4 Hz, 2H), MS (m/z): 328.3 (M+H$^+$).

Example 47

4-(2-{(2R)-2-[(1E,3E)-4-methylhexa-1,3-dienyl]-5-oxopyrrolidin-1-yl}ethyl)benzoic acid The second isomer from RP-HPLC.

$^1$HNMR (CD$_3$OD): δ 1.084 (t, J=7.3 Hz, 2H), 1.78 (q, J=7.3 Hz, 2H), 1.84 (s, 3H), 2.14 (m, 3H), 2.36 (m, 2H), 2.78 (m, 1H), 2.88 (m, 1H), 3.09 (m, 1H), 3.67 (m, 1H), 4.88 (m, 1H), 5.24 (dd, J=9.2 and 15 Hz, 1H), 5.84 (d, J=11 Hz, 1H), 6.47 (dd, J=11 and 15 Hz, 1H), 7.17 (d, J=8.4 Hz, 2H), 7.88 (d, J=8.4 Hz, 2H), MS (m/z): 328.4 (M+H$^+$).

Examples 48 and 49

Synthesis of: 6-(3-{(2R)-2-[(1Z,3E)-4-methylocta-1,3-dienyl]-5-oxopyrrolidin-1-yl}propyl)pyridine-2-carboxylic acid and 6-(3-{(2R)-2-[(1E,3E)-4-methylocta-1,3-dienyl]-5-oxopyrrolidin-1-yl}propyl)pyridine-2-carboxylic acid

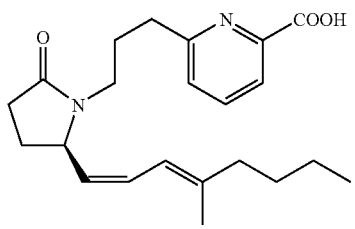

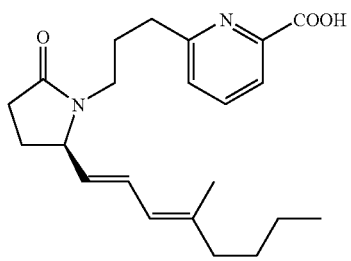

The title compounds were synthesized from 6-bromopyridine-2-carboxylic acid (using procedure U.S. Pat. No. 6,498,172) and Intermediate 3.6 following the procedure described for Example 3 (Method B).

Example 48

6-(3-{(2R)-2-[(1Z,3E)-4-methylocta-1,3-dienyl]-5-oxopyrrolidin-1-yl}propyl)pyridine-2-carboxylic acid (first isomer in HPLC: ACN/H$_2$O/TFA)

$^1$H NMR (CD$_3$OD) δ 0.85 (t, J=7.3 Hz, 3H), 1.19-1.31 (m, 2H), 1.33-1.41 (m, 2H), 1.63-1.71 (m, 1H), 1.74 (s, 3H), 1.89-2.00 (m, 2H), 2.08 (t, J=7.5 Hz, 2H), 2.17-2.27 (m, 1H), 2.30-2.44 (m, 2H), 2.83-2.87 (m, 2H), 2.96-3.04 (m, 1H), 3.50-3.58 (m, 1H), 4.75-4.82 (m, 1H), 5.14 (t, J=10.6 Hz, 1H), 6.17 (d, J=11.7 Hz, 1H), 6.43 (t, J=11.4 Hz, 1H), 7.54 (d, J=7.6 Hz, 1H), 7.93 (t, J=7.7 Hz, 1H), 8.00 (d, J=7.6 Hz, 1H); MS (m/z) 393 (M+23).

Example 49

6-(3-{(2R)-2-[(1E,3E)-4-methylocta-1,3-dienyl]-5-oxopyrrolidin-1-yl}propyl)pyridine-2-carboxylic acid (second isomer in HPLC: ACN/H$_2$O/TFA)

$^1$H NMR (CD$_3$OD) δ 0.91 (t, J=7.3 Hz, 3H), 1.24-1.34 (m, 2H), 1.37-1.46 (m, 2H), 1.67-1.76 (m, 1H), 1.74 (s, 3H), 1.91-2.00 (m, 2H), 2.06 (t, J=7.5 Hz, 2H), 2.14-2.43 (m, 3H), 2.85 (, J=7.5 Hz, 2H), 2.97-3.05 (m, 1H), 3.48-3.56 (m, 1H), 4.19-4.25 (m, 1H), 5.35 (dd, J=14.7, 9.2 Hz, 1H), 5.81 (d, J=11.0 Hz, 1H), 6.48 (dd, J=15.0, 11.0 Hz, 1H), 7.49 (d, J=6.9 Hz, 1H), 7.88 (t, J=7.7 Hz, 1H), 7.96 (d, J=6.9 Hz, 1H); MS (m/z) 393 (M+23).

Examples 50 and 51

Synthesis of: 4-(2-{(2R)-2-[(1Z,3E)-4,6-dimethylhepta-1,3-dienyl]-5-oxopyrrolidin-1-yl}ethyl)benzoic acid and 4-(2-{(2R)-2-[(1E,3E)-4,6-dimethylhepta-1,3-dienyl]-5-oxopyrrolidin-1-yl}ethyl)benzoic acid

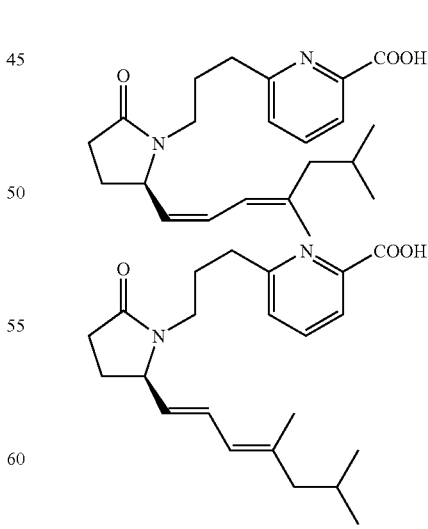

The title compounds were synthesized from Intermediate 1.4 and 4-methylpentan-2-one following the procedure described for Examples 30 and 31.

Example 50

4-(2-{(2R)-2-[(1Z,3E)-4,6-dimethylhepta-1,3-dienyl]-5-oxopyrrolidin-1-yl}ethyl)benzoic acid (first isomer in HPLC: ACN/H₂O/TFA)

¹H NMR (CD₃OD) δ 0.80-0.95 (m, 6H), 1.60-1.85 (m, 4H), 1.77 (s, 3H), 2.16-2.25 (m, 1H), 2.26-2.41 (m, 2H), 2.74-2.92 (m, 2H), 3.05-3.15 (m, 1H), 3.65-3.75 (m, 1H), 4.45-4.55 (m, 1H), 5.10 (t, J=10.6 Hz, 1H), 6.00 (d, J=12 Hz, 1H), 6.47 (t, J=12 Hz, 1H), 7.25 (m, 2H), 7.88 (m, 2H); MS (m/z) 356.3 (M+H).

Example 51

4-(2-{(2R)-2-[(1E,3E)-4,6-dimethylhepta-1,3-dienyl]-5-oxopyrrolidin-1-yl}ethyl)benzoic acid (second isomer in HPLC: ACN/H₂O/TFA)

¹H NMR (CD₃OD) δ 0.80-0.90 (m, 6H), 1.63-1.85 (m, 4H), 1.77 (s, 3H), 2.06-2.20 (m, 1H), 2.26-2.41 (m, 2H), 2.74-2.81 (m, 1H), 2.85-2.92 (m, 1H), 3.13-3.22 (m, 1H), 3.61-3.69 (m, 1H), 3.89-3.95 (m, 1H), 5.25 (dd, J=9.1, 15 Hz, 1H), 5.82 (d, J=11 Hz, 1H), 6.38 (dd, J=15.0, 11 Hz, 1H), 7.18 (d, J=8.1 Hz, 2H), 7.87 (d, J=8.0 Hz, 2H); MS (m/z) 356.3 (M+H).

Examples 52 and 53

Synthesis of 4-(2-{(2R)-2-[(1Z,3E)-4,7,7-trimethylocta-1,3-dienyl]-5-oxopyrrolidin-1-yl}ethyl)benzoic acid and 4-(2-{(2R)-2-[(1E,3E)-4,7,7-trimethylocta-1,3-dienyl]-5-oxopyrrolidin-1-yl}ethyl)benzoic acid

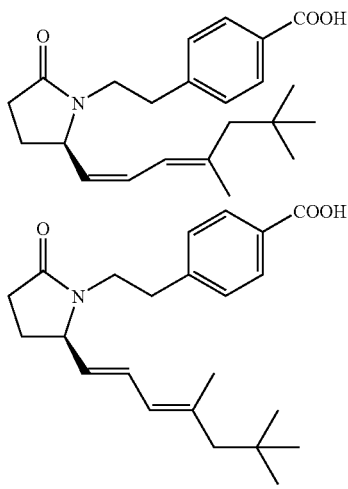

Intermediate 52.1

Methyl 4-(2-{(2R)-2-[(1E/Z,3E)-4,7,7-trimethylocta-1,3-dienyl]-5-oxopyrrolidin-1-yl}ethyl)benzoate (Scheme 6)

To a suspension of 3,6,6-trimethylhepta-2-enyl triphenylphosphonium bromide (988.36 mg, 2.18 mmol), prepared from methyl acetoacetate, using the procedure for Intermediate 26.1, in dry THF (20 mL) at −78° C. was added n-BuLi (2.37 mL, 1.6 M in hexanes, 4.36 mmol). The resulting red colored mixture was stirred for 30 minutes and Intermediate 1.4 (400 mg, 1.45 mmol) in THF (3 mL) was added. The mixture was stirred at −78° C. for 30 minutes and was warmed to room temperature. The reaction was quenched with water (10 mL) and extracted with EtOAc (3×25 mL), washed with brine (3×10 mL). The organic layer was dried over MgSO₄, filtered and concentrated. The residue was used for the next reaction without purification (400 mg, 69%).

Examples 52 and 53

To a solution of Intermediate 52.1 (400 mg) in MeOH/THF (3/3 mL) was added NaOH (2.7 mL, 1.0 M, 2.7 mmol). The mixture was stirred for overnight. The product was purified through RP-HPLC using ACN/H₂O/TFA to afford the desired single compounds.

Example 52

4-(2-{(2R)-2-[(1Z,3E)-4,7,7-trimethylocta-1,3-dienyl]-5-oxopyrrolidin-1-yl}ethyl)benzoic acid The first isomer from RP-HPLC.

¹HNMR (CD₃OD): δ 0.909 (s, 9H), 1.5-1.7 (m, 3H), 1.80 (s, 3H), 2.16 (m, 2H), 2.36 (m, 2H), 2.78 (m, 1H), 2.88 (m, 1H), 3.09 (m, 1H), 3.67 (m, 1H), 4.63 (m, 1H), 5.07 (t, J=10.6 Hz, 1H), 6.17 (d, J=11.3 Hz, 1H), 6.47 (t, J=11.3 Hz, 1H), 7.15 (d, J=8.4 Hz, 2H), 7.86 (d, J=8.4 Hz, 2H), MS (m/z): 370.2 (M+H⁺).

Example 53

4-(2-{(2R)-2-[(1E,3E)-4,7,7-trimethylocta-1,3-dienyl]-5-oxopyrrolidin-1-yl}ethyl)benzoic acid The second isomer from RP-HPLC.

¹HNMR (CD₃OD): δ 0.909 (s, 9H), 1.5-1.7 (m, 3H), 1.80 (s, 3H), 2.16 (m, 2H), 2.36 (m, 2H), 2.78 (m, 1H), 2.88 (m, 1H), 3.09 (m, 1H), 3.67 (m, 1H), 4.63 (m, 1H), 5.29 (dd, J=9.2 and 15 Hz, 1H), 5.89 (d, J=10.7 Hz, 1H), 6.39 (dd, J=11 and 15 Hz, 1H), 7.18 (d, J=8.4 Hz, 2H), 7.88 (d, J=8.4 Hz, 2H), MS (m/z): 370.2 (M+H⁺).

Examples 54 and 55

Synthesis of 4-(2{(2R)-2-[(1Z,3E)-4-dimethylhexa-1,3-dienyl]-5-oxopyrrolidin-1-yl}ethyl)benzoic acid and 4-(2-{(2R)-2-[(1E,3E)-4,5-dimethylhexa-1,3-dienyl]-5-oxopyrrolidin-1-yl}ethyl)benzoic acid

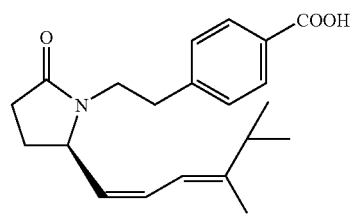

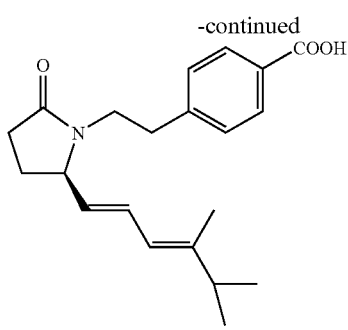

Intermediate 54.1

Methyl 4-(2-{(2R)-2-[(1E/Z,3E)-4,5-dimethylhexa-1,3-dienyl]-5-oxopyrrolidin-1-yl}ethyl)benzoate (Scheme 6)

To a suspension of 3,4-dimethylpent-2-enyl triphenylphosphonium bromide (957.02 mg, 2.18 mmol), prepared from 3-methylbutan-2-one, using the procedure for Intermediate 26.1, in dry THF (20 mL) at −78° C. was added n-BuLi (2.73 mL, 1.6 M in hexanes, 4.36 mmol). The resulting red colored mixture was stirred for 30 minutes and Intermediate 1.4 (400 mg, 1.45 mmol) in THF (3 mL) was added. The mixture was stirred at −78° C. for 30 minutes and was warm to room temperature. The reaction was quenched with water (10 mL) and extracted with EtOAc (3×25 mL), washed with brine (3×10 mL). The organic layer was dried over MgSO₄, filtered and concentrated. The residue was used for the next reaction without purification (400 mg, 69%).

Examples 54 and 55

To a solution of Intermediate 54.1 (400 mg) in MeOH/THF (3/3 mL) was added NaOH (2.8 mL, 1.0 M, 2.8 mmol). The mixture was stirred for overnight. The product was purified through RP-HPLC using ACN/H₂O/TFA to afford the desired single compounds.

Example 54

4-(2-{(2R)-2-[(1Z,3E)-4,5-dimethylhexa-1,3-dienyl]-5-oxopyrrolidin-1-yl}ethyl)benzoic acid The first isomer from RP-HPLC.
¹HNMR (CD₃OD): δ 1.084 (d, J=7.3 Hz, 6H), 1.56 (q, J=7.3 Hz, 1H), 1.84 (s, 3H), 2.14 (m, 3H), 2.36 (m, 2H), 2.78 (m, 1H), 2.88 (m, 1H), 3.09 (m, 1H), 3.67 (m, 1H), 4.54 (m, 1H), 5.10 (t, J=10.3 Hz, 1H), 6.09 (d, J=11.4 Hz, 1H), 6.47 (t, J=10.3 Hz, 1H), 7.15 (d, J=8.4 Hz, 2H), 7.86 (d, J=8.4 Hz, 2H), MS (m/z): 342.1 (M+H⁺).

Example 55

4-(2-{(2R)-2-[(1E,3E)-4,5-dimethylhexa-1,3-dienyl]-5-oxopyrrolidin-1-yl}ethyl)benzoic acid The second isomer from RP-HPLC.
¹HNMR (CD₃OD): δ 1.080 (d, J=7.3 Hz, 6H), 1.57 (q, J=7.3 Hz, 1H), 1.84 (s, 3H), 2.14 (m, 3H), 2.36 (m, 2H), 2.78 (m, 1H), 2.88 (m, 1H), 3.09 (m, 1H), 3.67 (m, 1H), 4.88 (m, 1H), 5.24 (dd, J=9.2 and 15 Hz, 1H), 5.84 (d, J=11 Hz, 1H), 6.47 (dd, J=11 and 15 Hz, 1H), 7.17 (d, J=8.4Hz, 2H), 7.88 (d, J=8.4H, 2H), MS (m/z): 342.1 (M+H⁺).

Examples 56 and 57

Synthesis of 4-(2-{(2R)-2-[(1Z,3E)-4-cyclohexylbuta-1,3-dienyl]-5-oxopyrrolidin-1-yl}ethyl)benzoic acid and 4-(2-{(2R)-2-[(1E,3E)-4-cyclohexylbuta-1,3-dienyl]-5-oxopyrrolidin-1-yl}ethyl)benzoic acid

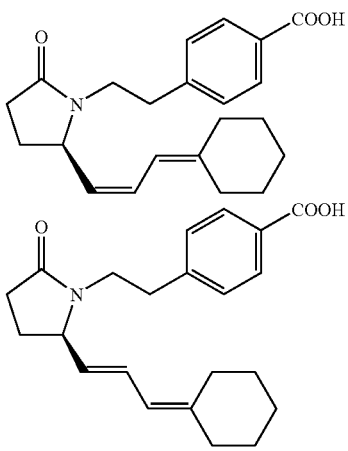

Intermediate 56.1

Methyl 4-(2-{(2R)-2-[(1E/Z,3E)-4-cyclohexylbuta-1,3-dienyl]-5-oxopyrrolidin-1-yl}ethyl)benzoate (Scheme 6)

To a suspension of 3-cyclohexyprop-2-enyl triphenylphosphonium bromide (984 mg, 2.18 mmol), prepared from ethyl cyclohexnone, using the procedure for Intermediate 26.1, in dry THF (20 mL) at −78° C. was added n-BuLi (2.73 mL, 1.6 M in hexanes, 4.36 mmol). The resulting red colored mixture was stirred for 30 minutes and Intermediate 1.4 (400 mg, 1.45 mmol) in THF (3 mL) was added. The mixture was stirred at −78° C. for 30 minutes and was warm to room temperature. The reaction was quenched with water (10 mL) and extracted with EtOAc (3×25 mL), washed with brine (3×10 mL). The organic layer was dried over MgSO₄, filtered and concentrated. The residue was used for the next reaction without purification (430 mg).

Examples 56 and 57

To a solution of Intermediate 56.1 (430 mg) in MeOH/THF (3/3 mL) was added NaOH (2.93 mL, 1.0 M, 2.93 mmol). The mixture was stirred for overnight. The product was purified through RP-HPLC using ACN/H₂O/TFA to afford the desired single compounds.

Example 56

4-(2-{(2R)-2-[(1Z,3E)-4-cyclohexylbuta-1,3-dienyl]-5-oxopyrrolidin-1-yl}ethyl)benzoic acid The first isomer from RP-HPLC. ¹HNMR (CD₃OD): δ 1.63 (m, 6H), 2.21 (m, 3H), 2.40 (m, 2H), 2.80 (m, 1H), 2.88

(m, 1H), 3.11 (m, 1H), 3.69 (m, 1H), 4.68 (m, 1H), 5.10 (t, J=9.4 Hz, 1H), 6.71 (m, 2H), 7.11 (d, J=8.1 Hz, 2H), 7.82 (d, J=8.1 Hz, 2H), MS (m/z): 354.1 (M+H$^+$).

Example 57

4-(2-{(2R)-2-[(1E,3E)-4-cyclohexybuta-1,3-dienyl]-5-oxopyrrolidin-1-yl}ethyl)benzoic acid The second isomer from RP-HPLC. $^1$HNMR (CD$_3$OD): δ 1.65 (m, 6H), 2.20 (m, 3H), 2.35 (m, 2H), 2.80 (m, 1H), 2.88 (m, 1H), 3.11 (m, 1H), 3.69 (m, 1H), 4.68 (m, 1H), 5.32 (dd, J=9.2 and 14.7 Hz, 1H), 6.47 (d, J=11 Hz, 1H), 6.54 (dd, J=11 and 14.7 Hz, 1H) 7.19 (d, J=8.1 Hz, 2H), 7.82 (d, J=8.1 Hz, 2H), MS (m/z): 354.1 (M+H$^+$).

Examples 58, 59, 60 and 61

Synthesis of 4-(2-{(2R)-2-[(1Z,3E)-4-phenyl-4-triflurobuta-1,3-dienyl]-5-oxopyrrolidin-1-yl}ethyl)benzoic acid, 4-(2-{(2R)-2-[(1E,3E)-4-phenyl-4-triflurobuta-1,3-dienyl]-5-oxopyrrolidin-1-yl}ethyl)benzoic acid, 4-(2-{(2R)-2-[(1Z,3Z)-4-phenyl-4-triflurobuta-1,3-dienyl]-5-oxopyrrolidin-1-yl}ethyl)benzoic acid and 4-(2-{(2R)-2-[(1E,3Z)-4-phenyl-4-triflurobuta-1,3-dienyl]-5-oxopyrrolidin-1-yl}ethyl)benzoic acid

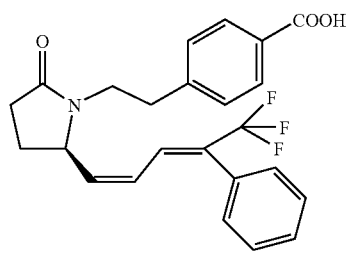

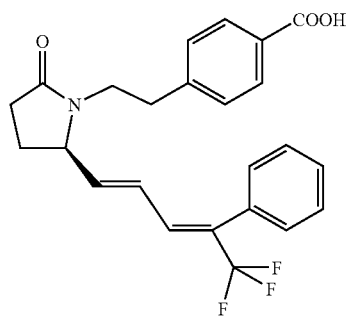

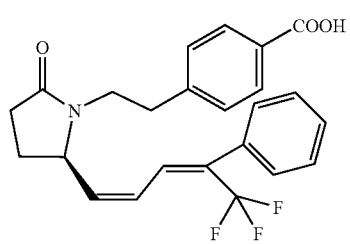

-continued

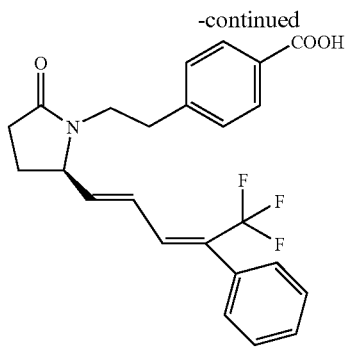

Intermediate 58.1

4-(2-{(2R)-2-[(1E/Z,3E/Z)-4-phenyl-4-triflurobuta-1,3-dienyl]-5-oxopyrrolidin-1-yl}ethyl)benzoate (Scheme 6)

To a suspension of (2Z)-3-phenyl-3-trifluoroprop-2-enyl triphenylphosphonium bromide (360 mg, 0.683 mmol), prepared from trifluoroacetophenone, using the procedure for Intermediate 26.1, in dry THF (20 mL) at −78° C. was added n-BuLi (0.85 mL, 1.6 M in hexanes, 1.36 mmol). The resulting red colored mixture was stirred for 30 minutes and Intermediate 1.4 (192 mg, 0.7 mmol) in THF (3 mL) was added. The mixture was stirred at −78° C. for 30 minutes and was warm to room temperature. The reaction was quenched with water (10 mL) and extracted with EtOAc (3×25 mL), washed with brine (3×10 mL). The organic layer was dried over MgSO$_4$, filtered and concentrated. The residue was used for the next reaction without purification (160 mg).

Examples 58, 59, 60 and 61

To a solution of Intermediate 58.1 (160 mg) in MeOH/THF (3/3 mL) was added NaOH (3.5 mL, 1.0 M, 3.5 mmol). The mixture was stirred for overnight. The product was purified through RP-HPLC using CAN/H$_2$O/TFA to afford the desired single compounds.

Example 58

4-(2-{(2R)-2-[(1Z,3E)-4-phenyl-4-trifluorobuta-1,3-dienyl]-5-oxopyrrolidin-1-yl}ethyl)benzoic acid The third isomer from RP-HPLC.
$^1$HNMR (CD$_3$OD): δ 1.68 (m, 1H), 2.20-2.40 (m, 2H), 2.81 (m, 1H), 2.88 (m, 1H), 3.11 (m, 1H), 3.69 (m, 1H), 4.68 (m, 1H), 5.10 (dd, J=9.0 and 12.9 Hz, 1H), 6.71 (m, 2H), 7.11 (d, J=8.1 Hz, 2H), 7.27 (d, J=7.4 Hz, 1H), 7.34 (t, J=7.4 Hz, 2H), 7.47 (d, J=7.4 Hz, 2H), 7.82 (d, J=8.1 Hz, 2H).

Example 59

4-(2-{(2R)-2-[(1E,3E)-4-phenyl-4-trifluorobuta-1,3-dienyl]-5-oxopyrrolidin-1-yl}ethyl)benzoic acid The fourth isomer from RP-HPLC.

$^1$HNMR (CD$_3$OD): δ 1.74 (m, 1H), 2.35 (m, 2H), 2.80 (m, 1H), 2.88 (m, 1H), 3.11 (m, 1H), 3.69 (m, 1H), 4.68 (m, 1H), 5.51 (dd, J=8.8 and 14.6 Hz, 1H), 6.52 (d, J=10.3 Hz, 1H), 6.51 (dd, J=10.3 and 14.6 Hz, 1H) 7.19 (d, J=8.1 Hz, 2H), 7.21 (d, J=7.4 Hz, 1H), 7.31 (t, J=7.4 Hz, 2H), 7.47 (d, J=7.4 Hz, 2H), 7.82 (d, J=8.1 Hz, 2H).

Example 60

4-(2-{(2R)-2-[(1Z,3Z)-4-phenyl-4-trifluorobuta-1,3-dienyl]-5-oxopyrrolidin-1-yl}ethyl)benzoic acid The first isomer from RP-HPLC.

$^1$HNMR (CD$_3$OD): δ 1.65 (m, 1H), 2.20-2.40 (m, 2H), 2.81 (m, 1H), 2.88 (m, 1H), 3.11 (m, 1H), 3.69 (m, 1H), 4.68 (m, 1H), 5.10 (dd, J=9.0 and 12.9 Hz, 1H), 6.71 (m, 2H), 7.11 (d, J=8.1 Hz, 2H), 7.27 (d, J=7.4 Hz, 1H), 7.34 (t, J=7.4 Hz, 2H), 7.47 (d, J=7.4 Hz, 2H), 7.84 (d, J=8.1Hz, 2H).

Example 61

4-(2-{(2R)-2-[(1E,3Z)-4-phenyl-4-trifluorobuta-1,3-dienyl]-5-oxopyrrolidin-1-yl}ethyl)benzoic acid The second isomer from RP-HPLC.

$^1$HNMR (CD$_3$OD): δ 1.70 (m, 1H), 2.37 (m, 2H), 2.84 (m, 1H), 2.88 (m, 1H), 3.11 (m, 1H), 3.69 (m, 1H), 4.68 (m, 1H), 5.51 (dd, J=8.8 and 14.6 Hz, 1H), 6.52 (d, J=10.3 Hz, 1H), 6.51 (dd, J=10.3 and 14.6 Hz, 1H) 7.19 (d, J=8.1 Hz, 2H), 7.21 (d, J=7.4 Hz, 1H), 7.31 (t, J=7.4 Hz, 2H), 7.47 (d, J=7.4 Hz, 2H), 7.86 (d, J=8.1 Hz, 2H).

Examples 62 and 63

Synthesis of 4-(2-{(2R)-2-[(1Z,3E)-4-cyclopropyl-penta-1,3-dienyl]-5-oxopyrrolidin-1-yl}ethyl)benzoic acid and 4-(2-{(2R)-2-[(1E,3E)-4-cyclopropyl-penta-1,3-dienyl]-5-oxopyrrolidin-1-yl}ethyl)benzoic acid

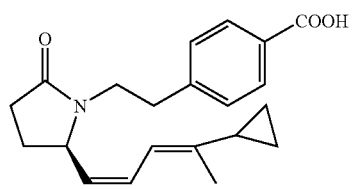

-continued

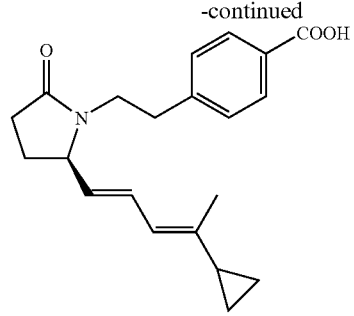

Intermediate 62.1

4-(2-{(2R)-2-[(1E/Z,3E)-4-cyclopropylpenta-1,3-dienyl]-5-oxopyrrolidin-1-yl}ethyl)benzoate
(Scheme 6)

To a suspension of (2E)-3-cyclopropylbut-2-enyl triphenylphosphonium bromide (570 mg, 1.3 mmol), prepared from cyclopropyl methyl ketone, using the procedure for Intermediate 26.1, in dry THF (20 mL) at −78° C. was added n-BuLi (2.0 mL, 1.6 M in hexanes, 3.25 mmol). The resulting red colored mixture was stirred for 30 minutes and Intermediate 1.4 (357.5 mg, 1.3 mmol) in THF (3 mL) was added. The mixture was stirred at −78° C. for 30 minutes and was warm to room temperature. The reaction was quenched with water (10 mL) and extracted with EtOAc (3×25 mL), washed with brine (3×10 mL). The organic layer was dried over MgSO$_4$, filtered and concentrated. The residue was used for the next reaction without purification (50 mg).

Examples 62 and 63

To a solution of Intermediate 62.1 (160 mg) in MeOH/THF (3/3 mL) was added NaOH (3.5 mL, 1.0 M, 3.5 mmol). The mixture was stirred for overnight. The product was purified through RP-HPLC using ACN/H$_2$O/TFA to afford the desired single compounds.

Example 62

4-(2-{(2R)-2-[(1Z,3E)-4-cyclopropylpenta-1,3-dienyl]-5-oxopyrrolidin-1-yl}ethyl)benzoic acid The first isomer from RP-HPLC.

$^1$HNMR (CD$_3$OD): δ 1.74 (m, 5H), 2.18 (s, 3H), 2.20-2.40 (m, 2H), 2.81 (m, 1H), 2.88 (m, 1H), 3.11 (m, 1H), 3.69 (m, 1H), 4.68 (m, 1H), 5.10 (dd, J=9.0 and 12.9 Hz, 1H), 6.71 (m, 2H), 7.11 (d, J=8.1 Hz, 2H), 7.82 (d, J=8.1 Hz, 2H).

Example 63

4-(2-{(2R)-2-[(1E,3E)-4-cyclopropylpenta-1,3-dienyl]-5-oxopyrrolidin-1-yl}ethyl)benzoic acid The fourth isomer from RP-HPLC.

$^1$HNMR (CD$_3$OD): δ 1.69 (m, 5H), 2.21 (s, 3H), 2.35 (m, 2H), 2.80 (m, 1H), 2.88 (m, 1H), 3.11 (m, 1H), 3.69 (m, 1H), 4.68 (m, 1H), 5.51 (dd, J=8.8 and 14.6 Hz, 1H), 6.52 (d, J=10.3 Hz, 1H), 6.51 (dd, J=10.3 and 14.6 Hz, 1H) 7.19 (d, J=8.1 Hz, 2H), 7.82 (d, J=8.1 Hz, 2H).

Examples 64 and 65

Synthesis of 5-(3-{(2R)-2-[(1Z,3E)-4-methylocta-1,3-dienyl]-5-oxopyrrolidin-1-yl}propyl)nicotinic acid and 5-(3-{(2R)-2-[(1E,3E)-4-methylocta-1,3-dienyl]-5-oxopyrrolidin-1-yl}propyl)nicotinic acid

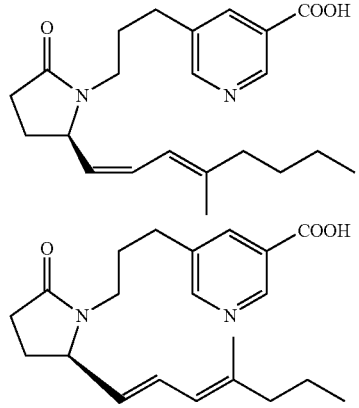

The title compounds were synthesized from 5-bromonicotinic acid (prepared from (5R)-5-(hydroxymethyl)pyrrolidin-2-one according to WO 0242268) and Intermediate 3.6 following the procedure described for Example 3 (Method B).

Example 64

5-(3-{(2R)-2-[(1Z,3E)-4-methylocta-1,3-dienyl]-5-oxopyrrolidin-1-yl}propyl)nicotinic acid (first isomer in HPLC: ACN/H$_2$O/TFA)

$^1$H NMR (CD$_3$OD) δ 0.86 (t, J=7.3 Hz, 3H), 1.21-1.31 (m, 2H), 1.32-1.42 (m, 2H), 1.65-1.73 (m, 1H), 1.75 (s, 3H), 1.78-1.91 (m, 2H), 2.05-2.12 (m, 2H), 2.17-2.29 (m, 1H), 2.37-2.42 (m, 2H), 2.68-2.74 (m, 2H), 2.97-3.05 (m, 1H), 3.45-3.53 (m, 1H), 4.69-4.76 (m, 1H), 5.154 (t, J=10.3 Hz, 1H), 6.15 (d, J=11.8 Hz, 1H), 6.45 (t, J=11.3 Hz, 1H), 8.24 (s, broad, 1H); MS (m/z) 393 (M+23).

Example 65

5-(3-{(2R)-2-[(1E,3E)-4-methylocta-1,3-dienyl]-5-oxopyrrolidin-1-yl}propyl)nicotinic acid (second isomer in HPLC: ACN/H$_2$O/TFA)

$^1$H NMR (CD$_3$OD) δ 0.91 (t, J=7.3 Hz, 3H), 1.25-1.34 (m, 2H), 1.37-1.46 (m, 2H), 1.69-1.79 (m, 1H), 1.74 (s, 3H), 1.80-1.93 (m, 2H), 2.06 (t, J=7.3 Hz, 2H), 1.98-2.44 (m, 3H), 2.71-2.76 (m, 2H), 3.01-3.08 (m, 1H), 3.42-3.50 (m, 1H), 4.16-4.22 (m, 1H), 5.36 (dd, J=15.0, 9.2 Hz, 1H), 5.81 (d, J=11.4 Hz, 1H), 6.48 (dd, J=15.0, 10.9 Hz, 1H), 8.34 (s, broad, 1H), 8.65 (s, broad, 1H), 8.97 (s, broad, 1H); MS (m/z) 393 (M+23).

Example 66

Preparation of a Pharmaceutical Formulation

The following Formulation examples illustrate representative pharmaceutical compositions according to the present invention being.

Formulation 1—Tablets

A gamma lactam diene compound of Formula I is admixed as a dry powder with a dry gelatin binder in an approximate 1:2 weight ration. A minor amount of magnesium stearate is added as a lubricant. The mixture is formed into 240-270 mg tablets (80-90 mg of active gamma lactam diene compound per tablet) in a tablet press.

Formulation 2—Capsules

A gamma lactam diene compound of Formula I is admixed as a dry powder with a starch diluent in an approximate 1:1 weight ratio. The mixture is filled into 250 mg capsules (125 mg of active gamma lactam diene compound per capsule).

Formulation 3—Liquid

A gamma lactam diene compound of Formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A gamma lactam diene compound of Formula I is admixed as a dry powder with a dry gelatin binder in an approximate 1:2 weight ratio. A minor amount of magnesium stearate is added as a lubricant. The mixture is formed into 450-900 mg tablets (150-300 mg of active gamma lactam diene compound) in a tablet press.

Formulation 5—Injection

A gamma lactam diene compound of Formula I is dissolved in a buffered sterile saline injectable aqueous medium to a concentration of approximately 5 mg/ml.

Example 67

Prostaglandin EP2 Binding Assay

Compounds of the invention were tested in an EP2 receptor binding assay of the following protocol. As referred to herein, the term an "EP2 receptor binding assay" designates the following protocol.

A mixture containing 20 μg of EP2 receptor membranes, 0.5 mg of wheat germ agglutinin coated PVT-SPA beads, with or without compound of the invention (25 μl per well) or 10 μM of cold PGE2 at 1% DMSO and 20 nM $^3$H-PGE2 in assay buffer containing 25 mM MES, 10 mM MgCl$_2$, 1 mM EDTA, pH 6.0 are incubated in Corning 3600 plates on a plate shaker for 2 hrs at room temperature. $^3$H-PGE2 binding is evaluated by counting the plates on the top count using the $^3$H SPA dpm2 program. % Binding and Ki value for inhibitors are calculated based on the one site competition parameter using the Graphpad® prism program. EP2 Ki values are set forth in the Table 1 which follows Example 69 below.

Example 68

EP2 cAMP Assay

It is known that PGE2 has a marked effect on cAMP (Cyclic adenosine monophosphate) levels (Coleman et al., 1989). This effect is thought to be achieved via EP2 and EP4 receptors (Choung et al. 1998).

Bone resorption properties of PGE2 is thought to result from a mechanism involving cAMP (Miyaura, 2001). In addition, the actions of gonadotrophins on the ovary and ovarian cyclicity (initiation of follicular development selection of a single preovulatory follicle, corpus luteum function, corpus luteum regression, and corpus luteum rescue during early pregnancy) are though to be controlled by cAMP.

Therefore, the compounds of the invention are tested for their ability in modulating cAMP levels in cells overexpressing EP2 (Example 68) or EP4 (Example 70 below) receptors.

Compounds of the invention were tested in a total cAMP assay as follows. HEK293-EBNA cells transfected with pCEP4-hEP2 receptors were seeded in 96 well opaque plate (Costar #3917) at $4\times10^4$ cells per well in 100 µl of culture medium (D-MEM/F12 supplemented with 10% FBS, 2 nM L-glutamine, and 250 µg/ml of hygromycin; all from GibcoBRL) and incubated at 37° C. After overnight incubation, the medium was removed from each well and replaced with 45 µl of assay medium consisted of phenol red free D-MEM/F-12, 0.1% BSA (GibcoBRL) and 0.1 mM 3-isobutyl-1-methyl-xanthine (Sigma). After 15 minutes of incubation at 37° C., 16-16-dimethyl PGE-2 or compounds at desired concentrations in 20 µl of assay medium were added to cells and further incubated at 37° C. for 1 hour. Total cAMP (intra- and extra-cellular) was measured by using a cAMP-screen ELISA System (Tropix, #CS1000). Results (EP2 $EC_{50}$ (µM)) are shown in the Table 2 which follows Example 70 below.

Example 69

EP4 Binding Assay

Compounds of the invention were tested in an EP4 receptor binding assay of the following protocol.

A mixture containing 20 µg of EP4 receptor membranes, 0.5 mg of wheat germ agglutinin coated PVT-SPA beads, with or without compounds of the invention (25 µl per well) or 10 µM of cold PGE2 at 1% DMSO and 20 nM $^3$H-PGE2 in assay buffer containing 25 mM MES, 10 mM $MgCl_2$, 1 mM EDTA, pH 6.0 are incubated in Corning 3600 plates on a plate shaker for 2 hrs at room temperature. $^3$H-PGE2 binding is evaluated by counting the plates on the top count using the $^3$H SPA dpm2 program. % Binding and Ki value for inhibitors are calculated based on the one site competition parameter using the Graphpad® prism program. EP4 Ki values are set forth in the Table 1 below.

Results of the assays of Examples 67 and 69 are set forth in the following Table 1 wherein the tested compound is identified both by the corresponding synthetic Example number above as well as structure of the tested compound.

TABLE 1

| Example Number | h-EP2 Ki (µM) | h-EP4 Ki (µM) |
|---|---|---|
| 1 | 0.088 | 0.025 |
| 7 | 1.53 | 0.071 |
| 11 | 0.41 | 0.045 |
| 12 | 0.75 | 0.47 |
| 13 | 0.06 | 0.006 |
| 17 | 0.044 | 0.051 |
| 19 | 0.06 | 0.006 |
| 22 | 0.034 | 0.145 |
| 30 | 0.06 | 0.117 |
| 32 | 0.749 | 0.029 |
| 44 | 0.079 | 0.006 |
| 52 | 0.021 | 0.045 |
| 55 | 0.036 | 0.164 |
| 56 | 0.027 | 0.307 |
| 58 | 0.1 | 0.069 |
| 63 | 0.277 | 0.165 |

Example 70

EP4 cAMP Assay

Compounds of the invention were tested in a total cAMP assay as follows. HEK293-EBNA cells transfected with pCEP4-hEP4 receptors were seeded in 96 well opaque plate (Costar #3917) at $4\times10^4$ cells per well in 100 µl of culture medium (D-MEM/F12 supplemented with 10% FBS, 2 nM L-glutamine, and 250 µg/ml of hygromycin; all from GibcoBRL) and incubated at 37° C. After overnight incubation, the medium was removed from each well and replaced with 45 µl of assay medium consisted of phenol red free D-MEM/F-12, 0.1% BSA (GibcoBRL) and 0.1 mM 3-isobutyl-1-methyl-xanthine (Sigma). After 15 minutes of incubation at 37° C., 16-16-dimethyl PGE-2 or compounds at desired concentrations in 20 µl of assay medium were added to cells and further incubated at 37° C. for 1 hour. Total cAMP (intra- and extra-cellular) was measured by using a cAMP-screen ELISA System (Tropix, #CS1000). Results (EP4 $EC_{50}$ (µM)) are shown in the Table 2 immediately below.

Results of the assays of Examples 68 and 70 are set forth in the following Table 2 wherein the tested compound is identified both by the corresponding synthetic Example number above as well as structure of the tested compound.

TABLE 2

| Example Number | h-EP2 $EC_{50}$ (µM) | h-EP4 $EC_{50}$ (µM) |
|---|---|---|
| 1 | 0.197 | 0.02 |
| 7 | 2.6 | 0.002 |
| 11 | 1.05 | 0.002 |
| 19 | 0.049 | 0.002 |
| 22 | 0.023 | 0.021 |

Example 71

In Vivo Ovulation Assay

Ovulation induction activity of compounds of the invention was tested in a mature mouse ovulation induction model.

Mature 10-week-old CD-mice were used. Reagents were prepared as follows: PMSG (pregnant mare serum gonadotropin) (Calbiochem, cat #367222) and hCG (Serono) are diluted in PBS. PGE2 (Cayman, Ann Arbor Mich.) was dissolved in ethanol and diluted with 0.154 M NaHCO2 Buffer (pH 8.0) to final concentration of ethanol of less than 3 percent. A compound of the invention (based on solubility) was pre-dissolved in ethanol, DMSO or other reagents. The compound of the invention was then diluted with saline or other diluents such as PBS or NP3S (5% N-methyl-pyrrolidinone/30% PEG400/25% PEG200/20% Propylene Glycol in saline). PMSG stimulates ovarian follicular development. After PMSG stimulation, the mature follicules can be stimulated to rupture and release oocytes by an ovulation trigger, such as hCG or a compound of the invention.

The following test protocol is employed for the test animals (typically 5 animals per test group).
Day 1: Inject 5 IU PMSG in 200 µl PBS (i.p. 15:00 PM)
Day 2: No administration
Day 3: Injection of ovulation trigger hCG (i.p.) or hCG replacement (PGE2 or compound of the invention, s.c., i.v. or oral route), 15:00 PM
Day 4: Eighteen hours after injections of the ovulation triggers, animals were sacrificed by $CO_2$ asphyxiation and abdominal cavities were opened using fine scissors and forceps. Uterus, oviducts and ovaries were collected and placed in pre-labeled dishes containing phosphate buffered saline (PBS). The collected tissues were transferred to the laboratory and intact oviduct carefully dissected out from uterus and ovary under the dissection microscope. The dissected oviducts were placed on the glass microscopic slide and covered with another slide. Two slides were taped on two edges. The numbers of ovulated ova in the oviducts were counted using upright microscope with 4× objective and recorded.

For evaluating the oral activity of this compound, two experiments are conducted, the first experiment is conducted with non-fasted animals and the second experiment is conducted in 24 h fasted animals (water provided). Compounds of the invention, based on their solubility, are pre-dissolved in ethanol, DMSO or other reagents. Compounds of the invention are then with saline or other diluents such as PBS or NP3S before oral administration (i.e. 5% N-methyl-pyrrolidinone/30% PEG400/25% PEG200/20% Propylene Glycol in saline).

Compounds of the invention were be submitted to testing in the in vivo ovulation induction model as described above in order to assess their ability to induce ovulation via subcutaneous (sc), oral (po) and intravenous (iv) routes of administration.

The number of ova released after oral administration of compound of Example 3 administered at a dose of 20 mg/kg was on average 20. Saline is used as negative control where the number of ova is 0.

The results show that compounds of the invention are able to stimulate ovulation in mature mice.

The calculated $ED_{50}$ (dose of drug which produces 50% of its effect) for Compounds 3 and 44 by p.o. administration route is 1 mg/kg.

Example 72

In Vivo Inhibition of Guinea Pig Broncho-constriction

The activity of compounds of the invention in dilation of bronchiolar muscles, may be tested in different models. Guinea pig pulmonary-cholinergic in vivo model is generally used to test the materials for the treatments of asthma in human (Fleisch et al., 1985) Compounds of the invention can be tested in this methacholine-induced bronchomuscle constriction model as described below.

Groups of 3 Duncan Hartley derived male or female guinea pigs weighing 250±50 g are anesthetized with pentobarbital sodium (50 mg/kg i.p., plus an additional 15 mg/kg i.p. if required) and succinylcholine chloride (2 mg/animal i.p.) is subsequently administered to prevent spontaneous respiration. Body temperature is maintained at 37° to 38° C.

The trachea is cannulated and the guinea pig is ventilated with a Harvard rodent respirator in a closed system. Tracheal pressure is recorded through a side-arm of the cannula connected to a P23ID Statham transducer. Respiratory rate is set at 50 strokes/minute with a stroke volume (approximately 1 ml/100 g) sufficient to produce a baseline tracheal pressure of 6 cm $H_2O$. Mean arterial pressure (BP) is monitored from a cannulated carotid artery, and heart rate (HR) is obtained from chest electrodes arranged for lead II. The jugular vein is cannulated for i.v. vehicle or drug administration in a volume of 1 ml/kg.

Cholinergic-induced bronchoconstrictor responses, reflected as increases in tracheal pressure (cm $H_2O$), are elicited by administration of methacholine hydrochloride (10 µg/kg base weight i.v.). In vehicle-treated control animals, methacholine-induced bronchoconstriction ranges from 70 to 90 percent of its own maximum response (about 40 to 65 percent of maximum possible bronchoconstriction obtained by tracheal occlusion).

Compounds of the invention are also tested via intratracheal (IT) route of administration. In this other experiment, compound of the invention, reference compound or vehicle is administered IT 10 (5 min for experiment 1 and 2) minutes before methacholine chloride (10 µg/kg IV) induced bronchoconstriction. Tracheal pressure (ITP), blood pressure and heart rate are measured immediately as indicated in the material and methods sections.

MED (medium effective dose) is measure. A 50 percent or greater ($\geq 50\%$) inhibition of the induced broncho-constriction relative to vehicle treated control animals is considered significant.

Compounds of the invention are administered i.v. (10 mg/kg) 5 minutes before the methacholine challenge in 3 guinea pigs. A 50 percent or more ($\geq 50$) inhibition of the induced bronchoconstriction relative to vehicle treated control animals is considered significant.

The calculated effective dose ($ED_{50}$) was 0.2 mg/kg for compound 3 and 0.4 mg/kg for compound 22 by IT route.

Example 73

In Vivo Inhibition of LPS-induced TNFα Release in Mice

Prostaglandin E2 is suggested to be an endogenous inhibitor of inflammation through the EP4 receptor. Therefore EP2 and/or EP4 agonists are supposed to have an anti-inflammatory activity.

Endotoxins are the lipopolysaccharides (LPS) constituents of the outer membrane of Gram negative bacteria. Response to LPS has been shown to involve the activation of different cell populations and to lead to the expression of various inflammatory cytokines that include tumor necrosis factor-alpha (TNFα) and interferon gamma (IFN-γ).

The anti-inflammatory activity of compounds of the invention may be assessed after a LPS challenge using the following protocol:

Eight weeks old C3H/H mice (IFFA-CREDO, L'arbresle, France) receive an oral treatment with compounds of the invention 6 different doses (0.001, 0.01, 0.1, 1 or 3 and 10 mg/kg in 0.5% CMC/0.25% tween-20). Six mice are used by group. Fifteen minutes later, endotoxins (O111:B4 Sigma, 0.3 mg/kg) are intraperitoneally injected. Heparinized whole blood is collected by decapitation. TNFα level is determined in plasma by ELISA (R & D Systems, Abdingdon, UK). Control animals receive 0.5% CMC/0.25% tween-20 (10 ml/kg) as vehicle. Data obtained from experiments are expressed as the mean±SEM and analysed using one-way analysis of variance (ANOVA) followed by Dunnett's t-test.

The activity of the compounds of the invention is expressed as a percentage of inhibition of TNF release and the Inhibitory Dose at 50% of the maximum effect (ID50) is calculated in mg/kg. Data are presented in Table 3 below.

TABLE 3

| Example number | Dose (mg/kg) | % of Inhibition of TNF Release Mean ± SEM |
|---|---|---|
| 3 | 0.001 | 41 ± 5 |
|   | 0.01 | 43 ± 7 |
|   | 0.1 | 63 ± 3 |
|   | 1 | 68 ± 3 |
|   | 10 | 83 ± 3 |
| 22 | 0.001 | 46 ± 2 |
|   | 0.01 | 49 ± 4 |
|   | 0.1 | 59 ± 2 |
|   | 1 | 70 ± 4 |
|   | 10 | 87 ± 2 |

The data show that the compounds of the invention are able to inhibit the release of TNF alpha in a LPS-challenge model.

Example 74

In Vivo Inhibition of Aspirin-induced Gastric Ulceration

The activity of compounds of the invention as protective agents against gastric ulceration can be assayed as follows and as described in Guth et al., 1979.

Compounds of the invention are administered p.o. (100 mg/kg) to a group of 3 Wistar derived male or female overnight fasted rats weighing 200±20 g, 60 minutes before oral gavage with aspirin (150 mg/kg).

Four hours later, animals are sacrificed and gastric ulceration is scored for degree of hemorrhage and severity of ulcerative lesions as follows: 0=no hyperemia or bleeding, 1=hyperaemia, 2=slight spot bleeding, 3=hyperemia plus slight spot bleeding, 4=hyperemia plus spot bleeding within entire stomach. Reduction of concurrent control score values by 50 percent or more ($\geq 50\%$) is considered significant.

Ulceration scores decreased in a dose-dependent manner with the administration of Compound of Example 3. For example, a percentage of protection of 65% was obtained at a dose of 10 mg/kg of Compound of Example 3 administered orally.

Example 75

In Vivo Inhibition of Dextran Sodium Sulfate-induced Colitis

The anti-inflammatory activity of compounds of the invention in colitis can be assayed as follows.

Within 6-10 days after ingesting Dextran Sodium Sulfate (DSS) mice show sign of diarrhea, rectal bleeding and weight loss and colonic mucosal lesions include multiple erosion, ulceration, and marked inflammatory cell infiltration.

Ulcerative colitis (UC) was induced in female mice (Balb/c, 20-22 g, Elevage Janvier) by Dextran Sodium Sulfate (DSS 4%) administered in drinking water. The mice had free access to DSS during 5 days.

The compounds of the invention were solubilized in 0.25% CMC/0.5% Tween 20 and administered by gavage at days 3, 4, 5 and 6 after the induction of the UC.

The Animals are Divided in Three Groups:

The "treated group" wherein the animals have free access to DDS and are treated each day with compounds of the invention.

The "Dextran 4%" group wherein the animals have free access to DDS 4% and 0.5% CMC/O0.25% tween (vehicle) and are not treated.

The "control" group or "sham" group that do not receive DDS 4%.

The Following Parameters were Recorded:

The body weight was determined daily.

The severity of the UC was assessed by a clinical score estimating the constituency of the stool (0=firm, 1=loose, 2=diarrhea) and the presence of blood (0=no blood, 1=occult blood, 2=gross rectal bleeding).

Seven days after the induction of the disease, the animals were sacrificed. The length and the weight of the colon were determined and the ratio Length/Weight/100 g body weight was calculated.

The percentages of inhibition of weight loss, of clinical scores and of increase in the ratio colon length/weight, are calculated as follows:

% inhibition=(1−("value for treated group"−"value for control group"/"value for Dextran 4% group"−"value for control group))*100.

The percentages of inhibition are calculated for each days 5, 6 and 7 for each parameter.

Animals receiving compound of Example 3 (daily at days 3, 4, 5 and 6) at a concentration at 0.1 mg/kg, p.o. showed reduced dose-dependent loss of body-weight (39% inhibition compared to non-treated animals), improved clinical score (40% increase compared to non-treated animals) and increased colon weight/length (36% increase compared to non-treated animals).

Example 76

In Vivo Inhibition of Tobacco Smoke-induced COPD

The anti-inflammatory activity of compounds of the invention in respiratory diseases such pulmonary inflammation as observed in emphysema and Chronic Obstructive Pulmonary Diseases (COPD) can be tested as follows.

Female A/J mice (5 per exposure chamber) are exposed daily to Tobacco smoke (TS) generated from cigarettes or air for 11 consecutive days. Initial exposure is to 2 cigarettes on day 1 increasing to a maximum of 6 cigarettes by day 6/7. Exposure thereafter to Day 11 is 6 cigarettes. The rate of increase is regulated with regard to the daily observed tolerance of the mice.

Tobacco smoke exposed animals (n=60, 10/group) are orally dosed twice daily (−1 h and +6 h; 5 ml/kg) with either vehicle (methyl cellulose 0.5%) or compounds of the invention at doses at or about 1, 5, 10, 15 and 20 mg/kg.

Air exposed animals (n=10) are treated with vehicle.

Animals are killed by anaesthetic overdose (pentobarbitone Na, 100 mg/kg i.p.) 24 h following the 11$^{th}$ and final TS exposure. Blood is collected by cardiac puncture for preparation of plasma which is stored frozen at −20° C.

Broncho-alveolar lavage (BAL) is performed using 0.4 ml of heparinised phosphate buffered saline (PBS).

Cells recovered from the BAL are used for total and differential cell counts (cytospin preparation). BAL supernatants are frozen for subsequent analysis of protein levels. The remaining BAL fluid is analyzed for KC levels or for mucin.

Groups:
A. Vehicle p.o. twice daily (vehicle 5 ml/kg; −1 h & +6 h)/Air exposure
B. Vehicle p.o. twice daily (vehicle 5 ml/kg; −1 h & +6 h)/TS exposure
C. Compounds of the invention p.o. twice daily (1-20 mg/kg; −1 h & +6 h)/TS exposure The percentage of inhibition induced by compounds of the invention is calculated. The mean value for the sham controls is substracted from all the TS groups and the new value for the drug group is divided by the new value for the control TS group.

The invention has been described in detail with reference to preferred embodiments thereof. However, it will be appreciated that those skilled in the art, upon consideration of this disclosure, may make modifications and improvements within the spirit and scope of the invention.

REFERENCES

Abramowitz et al. 2000, Biochimica et Biophysica Acta 1483, 285-293;
Benoit et al., 2002, Expert Opinion in Therapeutical Patents, 12 (8)1225-1235;
Choung et al., 1998, Journal of Cellular Biochemistry 71:254:263;
Coleman et al. 1989, Prostanoids and their Receptors. In Comprehensive Medicinal Chemistry, The rational Design, Machanistic Study and Therapeutic Application Of Chemical Compounds vol. 3, Ed Hansch et al., 643-714, Pergamon Press, Oxford, UK;
Coleman et al. 1994, Pharmacological Reviews 46 (2), 205-229;
Guth et al., 1979, Gastroenterology 76: 88-93;
Hundertmark et al., 2000, Org. Lett., 2, 1729-1731;
Fleisch, et al., 1985 K. Pharmacol. Exp. Ther. 233: 148-157;
Langlois et al., 2000, Tetrahedron Letters, 41, 8285-8288;
Levi et al., 1998 Biochimie 80(11): 899-904;
Miyaura C., 2001, Nippon Yakurigaku Zasshi 117(4):293-7;
Nair et al., 1989, J. Med. Chem., 32, 1277-1283;
Negishi et al., 1979, Synthesis, 501-502;
Shen et al., 1999, J. Org. Chem., 64, 8873-8879
Shimamoto, 1991, Tetrahedrom Letters, 32, 1379-1380;
Uenishi et al., 1998 J. Org. Chem. 1998, 63, 8965-8975;
Ushikubi et al., 2000, Jpn J Pharmacol 83(4):279-85;
Watanabe et al., 1989, J. Org. Chem., 54, 4088-4097;
EP 1114816 Ono Pharmaceuticals
U.S. Pat. No. 6,235,780 Ono Pharmaceuticals
WO 9933794 Ono Pharmaceuticals
US 20010056060 Pfizer
WO 0242268 Pfizer
WO 0146140 Pfizer
WO 9902164 Synphora
WO 0224647 Ono Pharmaceuticals
US 20020004495 Merck
WO 0003980 Ono Pharmaceuticals
WO 8807537 Chinoin Gyogyszer

The invention claimed is:

1. A gamma-lactam diene of Formula I:

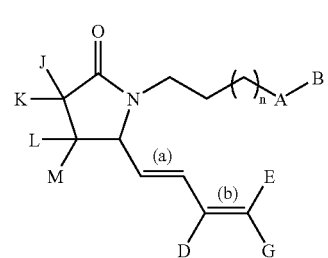

(I)

wherein A is selected from the group consisting of $C_1$-$C_4$ alkyl, aryl, heteroaryl, $C_3$-$C_6$ cycloalkyl and $C_3$-$C_6$ heterocycloalkyl;
B is C(O)Z wherein Z is selected from the group consisting of hydroxy, alkoxy, $C_1$-$C_6$ alkyl, $C_1$-$C_6$ heteroalkyl and $NR^1R^2$, wherein $R^1$ and $R^2$ are independently selected from the group consisting of H, $C_3$-$C_6$ cycloalkyl, $C_3$-$C_6$ heterocycloalkyl, aryl $C_1$-$C_6$ alkyl and heteroaryl $C_1$-$C_6$ alkyl;
D is selected from the group consisting of H, halogen and $C_1$-$C_6$ alkyl;
E is selected from the group consisting of H and $C_1$-$C_6$ alkyl;
G is selected from the group consisting of H, $C_1$-$C_6$ alkyl, $C_2$-$C_6$ alkenyl, $C_2$-$C_6$ alkynyl, $C_3$-$C_6$ cycloalkyl $C_1$-$C_6$ alkyl, $C_3$-$C_6$ cycloalkyl, $C_3$-$C_6$ heterocycloalkyl, aryl $C_1$-$C_6$ alkyl, heteroaryl $C_1$-$C_6$ alkyl, aryl and heteroaryl; or E and G form, together with the carbon atom they are attached to, a $C_3$-$C_6$ cycloalkyl ring;
J, K and L are independently selected from the group consisting of H, halogen, $C_1$-$C_6$ alkyl, aryl and heteroaryl;
M is selected from the group consisting of OR and H,
n is 0 or 1;
wherein the (a) and (b) double bonds can be independently in Z or E conformation.

2. A gamma-lactam diene of claim 1 having the following Formula II:

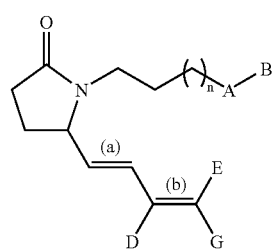

(II)

wherein A is selected from the group consisting of $C_1$-$C_4$ alkyl, aryl, heteroaryl, $C_3$-$C_6$ cycloalkyl and $C_3$-$C_6$ heterocycloalkyl;
B is C(O)Z wherein Z is selected from the group consisting of hydroxy, alkoxy, $C_1$-$C_6$ alkyl, $C_1$-$C_6$ heteroalkyl and NR¹R², wherein R¹ and R² are independently selected from the group consisting of H, $C_3$-$C_6$ cycloalkyl, $C_3$-$C_6$ heterocycloalkyl, aryl $C_1$-$C_6$ alkyl and heteroaryl $C_1$-$C_6$ alkyl;

D is selected from the group consisting of H, halogen and $C_1$-$C_6$ alkyl;

E is selected from the group consisting of H and $C_1$-$C_6$ alkyl;

G is selected from the group consisting of H, $C_1$-$C_6$ alkyl, $C_2$-$C_6$ alkenyl, $C_2$-$C_6$ alkynyl, $C_3$-$C_6$ cycloalkyl $C_1$-$C_6$ alkyl, $C_3$-$C_6$ cycloalkyl, $C_3$-$C_6$ heterocycloalkyl, aryl $C_1$-$C_6$ alkyl, heteroaryl $C_1$-$C_6$ alkyl, aryl and heteroaryl; or E and G form, together with the carbon atom they are attached to, a $C_3$-$C_6$ cycloalkyl ring;

n is 0 or 1; and wherein the (a) and (b) double bonds can be independently in Z or E conformation.

3. A gamma-lactam diene according to claim 1, wherein A is selected from the group consisting of aryl and heteroaryl.

4. A gamma-lactam diene according to claim 1, wherein A is phenyl.

5. A gamma-lactam diene according to claim 1, wherein A is thiophenyl.

6. A gamma-lactam diene according to claim 1, wherein A is furanyl.

7. A gamma-lactam diene according to claim 1, wherein B is C(O)Z, wherein Z is selected from the group consisting of hydroxy, alkyloxy and $C_1$-$C_6$ alkyl.

8. A gamma-lactam diene according to claim 1, wherein D is H.

9. A gamma-lactam diene according to claim 1, wherein D is methyl.

10. A gamma-lactam diene according to claim 1, wherein D is fluorine.

11. A gamma-lactam diene according to claim 1, wherein G is selected from the group consisting of $C_1$-$C_6$ alkyl, $C_2$-$C_6$ alkenyl, $C_2$-$C_6$ alkynyl and $C_3$-$C_6$ cycloalkyl $C_1$-$C_6$ alkyl.

12. A gamma-lactam diene according to claim 1, wherein G is selected from the group consisting of $C_3$-$C_6$ cycloalkyl, $C_3$-$C_6$ heterocycloalkyl, aryl $C_1$-$C_6$ alkyl, heteroaryl $C_1$-$C_6$ alkyl, aryl and heteroaryl.

13. A gamma-lactam diene according to claim 1, wherein E and G form, together with the carbon atom they are attached to, an optionally substituted $C_3$-$C_6$ cycloalkyl ring.

14. A gamma-lactam diene according to claim 1, wherein the bond (a) is in the "Z" conformation.

15. A gamma-lactam diene according to claim 1, wherein A is phenyl, thiophenyl or furanyl, B is COOH, and bond (a) is in the "Z" conformation.

16. A gamma-lactam diene according to claim 1, wherein A is phenyl, thiophenyl or furanyl, B is COOH, D is selected from the group consisting of H, methyl and fluorine, and bond (a) is in the "Z" conformation.

17. A gamma-lactam diene according to claim 1, wherein A is phenyl or thiophenyl, B is COOH, and D is H.

18. A gamma-lactam diene according to claim 1, wherein A is phenyl or thiophenyl, B is COOH, D is H, and E is selected from the group consisting of H and methyl.

19. A gamma-lactam diene according to claim 1, wherein A is phenyl or thiophenyl, B is COOH, D is H, E is selected from the group consisting of H and methyl, and G is selected from the group consisting of $C_1$-$C_6$ alkyl and $C_2$-$C_6$ alkenyl.

20. A gamma-lactam diene according to claim 1, wherein A is phenyl or thiophenyl, B is COOH, D is H, E is selected from the group consisting of H and methyl, and G is selected from the group consisting of $C_3$-$C_6$ cycloalkyl $C_1$-$C_6$ alkyl, $C_3$-$C_6$ cycloalkyl, $C_3$-$C_6$ heterocycloalkyl, aryl $C_1$-$C_6$ alkyl, heteroaryl $C_1$-$C_6$ alkyl, aryl and heteroaryl.

21. A gamma-lactam diene according to claim 1, wherein A is phenyl or thiophenyl, B is COOH, D is H, and E and G form, together with the carbon atom they are attached to, a $C_3$-$C_6$ cycloalkyl ring.

22. A gamma-lactam diene according to claim 1 selected from the group consisting of:

4-(2-{(2R)-2-[(1Z,3E)-octa-1,3-dienyl]-5-oxopyrrolidin-1-yl}ethyl)benzoic acid;

4-(2-{(2R)-2-[(1E,3E)-octa-1,3-dienyl]-5-oxopyrrolidin-1-yl}ethyl)benzoic acid;

4-(2-{(2R)-2-[(1Z,3E)-4-methylocta-1,3-dienyl]-5-oxopyrrolidin-1-yl}ethyl)benzoic acid;

4-(2-{(2R)-2-[(1E,3E)-4-methylocta-1,3-dienyl]-5-oxopyrrolidin-1-yl}ethyl)benzoic acid;

4-(2-{(2R)-2-[(1Z)-4-methylpenta-1,3-dienyl]-5-oxopyrrolidin-1-yl}ethyl)benzoic acid;

4-(2-{(2R)-2-[(1E)-4-methylpenta-1,3-dienyl]-5-oxopyrrolidin-1-yl}ethyl)benzoic acid;

4-(2-{(2R)-2-[(1Z,3E)-hexa-1,3-dienyl]-5-oxopyrrolidin-1-yl}ethyl)benzoic acid;

4-(2-{(2R)-2-[(1E,3E)-hexa-1,3-dienyl]-5-oxopyrrolidin-1-yl}ethyl)benzoic acid;

4-(2-{(2R)-2-[(1Z,3E)-hepta-1,3-dienyl]-5-oxopyrrolidin-1-yl}ethyl)benzoic acid;

4-(2-{(2R)-2-[(1E,3E)-hepta-1,3-dienyl]-5-oxopyrrolidin-1-yl}ethyl)benzoic acid;

4-(2-{(2R)-2-[(1Z,3E)-4,8-dimethylnona-1,3,7-trienyl]-5-oxopyrrolidin-1-yl}ethyl)benzoic acid;

4-(2-{(2R)-2-[(1E,3E)-4,8-dimethylnona-1,3,7-trienyl]-5-oxopyrrolidin-1-yl}ethyl)benzoic acid;

5-(3-{(2R)-2-[(1Z,3E)-4-methylocta-1,3-dienyl]-5-oxopyrrolidin-1-yl}propyl)thiophene-2-carboxylic acid;

5-(3-{(2R)-2-[(1E,3E)-4-methylocta-1,3-dienyl]-5-oxopyrrolidin-1-yl}propyl)thiophene-2-carboxylic acid;

4-(2-{(2R)-2-[(1Z,3Z)-hepta-1,3-dienyl]-5-oxopyrrolidin-1-yl}ethyl)benzoic acid;

4-(2-{(2R)-2-[(1Z and 1E,3Z)-hexa-1,3-dienyl]-5-oxopyrrolidin-1-yl}ethyl)benzoic acid;

5-(3-{(2R)-2-[(1Z,3E)-octa-1,3-dienyl]-5-oxopyrrolidin-1-yl}propyl)thiophene-2-carboxylic acid, 5-(3-{(2R)-2-[(1E,3E)-octa-1,3-dienyl]-5-oxopyrrolidin-1-yl}propyl)thiophene-2-carboxylic acid;

5-(3-{(2R)-2-[(1Z,3E)-octa-1,3-dienyl]-5-oxopyrrolidin-1-yl}propyl)thiophene-2-carboxylic acid;

5-(3-{(2R)-2-[(1E,3E)-3-methylocta-1,3-dienyl]-5-oxopyrrolidin-1-yl}propyl)thiophene-2-carboxylic acid;

4-(2-{(2R)-2-[(1Z,3E)-3-methylocta-1,3-dienyl]-5-oxopyrrolidin-1-yl}ethyl)benzoic acid;

4-(2-{(2R)-2-[(1E,3E)-3-methylocta-1,3-dienyl]-5-oxopyrrolidin-1-yl}ethyl)benzoic acid;

5-(3-{(2R)-2-[(1E,3E)-3-methylocta-1,3-dienyl]-5-oxopyrrolidin-1-yl}propyl)thiophene-2-carboxylic acid;

5-(3-{(2R)-2-[(1Z,3E)-3-methylocta-1,3-dienyl]-5-oxopyrrolidin-1-yl}propyl)-2-furoic acid;

5-(3-{(2R)-2-[(1E,3E)-3-methylocta-1,3-dienyl]-5-oxopyrrolidin-1-yl}propyl)-2-furoic acid;

4-(2-{(2R)-2-[(1Z,3E)-6-cyclopropyl-4-methylhexa-1,3-dienyl]-5-oxopyrrolidin-1-yl}ethyl)benzoic acid;

4-(2-{(2R)-2-[(1E,3E)-6-cyclopropyl-4-methylhexa-1,3-dienyl]-5-oxopyrrolidin-1-yl}ethyl)benzoic acid;

4-(2-{(2R)-2-[(1Z,3E)-4,7-dimethylocta-1,3-dienyl]-5-oxopyrrolidin-1-yl}ethyl)benzoic acid;

4-(2-{(2R)-2-[(1E,3E)-4,7-dimethylocta-1,3-dienyl]-5-oxopyrrolidin-1-yl}ethyl)benzoic acid;

4-(2-{(2R)-2-[(1Z,3E)-5-cyclopentyl-4-methylpenta-1,3-dienyl]-5-oxopyrrolidin-1-yl}ethyl)benzoic acid;
4-(2-{(2R)-2-[(1E,3E)-5-cyclopentyl-4-methylpenta-1,3-dienyl]-5-oxopyrrolidin-1-yl}ethyl)benzoic acid;
4-(2-{(2R)-2-[(1Z,3E)-4-phenylpenta-1,3-dienyl]-5-oxopyrrolidin-1-yl}ethyl)benzoic acid;
4-(2-{(2R)-2-[(1E,3E)-4-phenylpenta-1,3-dienyl]-5-oxopyrrolidin-1-yl}ethyl)benzoic acid;
4-(2-{(2R)-2-[(1Z,3Z)-4-phenylpenta-1,3-dienyl]-5-oxopyrrolidin-1-yl}ethyl)benzoic acid;
4-(2-{(2R)-2-[(1E,3Z)-4-phenylpenta-1,3-dienyl]-5-oxopyrrolidin-1-yl}ethyl)benzoic acid;
5-(3-{(2R)-2-[(1Z,3E)-octa-1,3-dienyl]-5-oxopyrrolidin-1-yl}propyl)-2-furoic acid;
5-(3-{(2R)-2-[(1E,3E)-octa-1,3-dienyl]-5-oxopyrrolidin-1-yl}propyl)-2-furoic acid;
4-(3-{(2R)-2-[(1Z,3E)-octa-1,3-dienyl]-5-oxopyrrolidin-1-yl}propyl)benzoic acid;
4-(3-{(2R)-2-[(1E,3E)-octa-1,3-dienyl]-5-oxopyrrolidin-1-yl}propyl)benzoic acid;
4-(2-{(2R)-2-[(1Z,3Z)-3-fluoro-4-methylocta-1,3-dienyl]-5-oxopyrrolidin-1-yl}ethyl)benzoic acid;
4(2-{(2R)-2-[(1E,3Z)-3-fluoro-4-methylocta-1,3-dienyl]-5-oxopyrrolidin-1-yl}ethyl)benzoic acid;
4(2-{(2R)-2-[(1Z,3E)-3-fluoro-4-methylocta-1,3-dienyl]-5-oxopyrrolidin-1-yl}ethyl)benzoic acid;
4(2-{(2R)-2-[(1E,3E)-3-fluoro-4-methylocta-1,3-dienyl]-5-oxopyrrolidin-1-yl}ethyl)benzoic acid;
4(2-{(2R)-2-[(1Z,3E)-4-methylhepta-1,3-dienyl]-5-oxopyrrolidin-1-yl}ethyl)benzoic acid;
4(2-{(2R)-2-[(1E,3E)-4-methylhepta-1,3-dienyl]-5-oxopyrrolidin-1-yl}ethyl)benzoic acid;
4(2-{(2R)-2-[(1Z,3E)-4-methylhexa-1,3-dienyl]-5-oxopyrrolidin-1-yl}ethyl)benzoic acid;
4-(2-{(2R)-2-[(1E,3E)-4-methylhexa-1,3-dienyl]-5-oxopyrrolidin-1-yl}ethyl)benzoic acid;
6-(3-{(2R)-2-[(1Z,3E)-4-methylocta-1,3-dienyl]-5-oxopyrrolidin-1-yl}propyl)pyridine-2-carboxylic acid;
6-(3-{(2R)-2-[(1E,3E)-4-methylocta-1,3-dienyl]-5-oxopyrrolidin-1-yl}propyl)pyridine-2-carboxylic acid;
4(2-{(2R)-2-[(1Z,3E)-4,6-dimethylhepta-1,3-dienyl]-5-oxopyrrolidin-1-yl}ethyl)benzoic acid;
4-(2-{(2R)-2-[(1E,3E)-4,6-dimethylhepta-1,3-dienyl]-5-oxopyrrolidin-1-yl}ethyl)benzoic acid;
4(2-{(2R)-2-[(1Z,3E)-4,7,7-trimethylocta-1,3-dienyl]-5-oxopyrrolidin-1-yl}ethyl)benzoic acid;
4-(2-{(2R)-2-[(1E,3E)-4,7,7-trimethylocta-1,3-dienyl]-5-oxopyrrolidin-1-yl}ethyl)benzoic acid;
4-(2-{(2R)-2-[(1Z,3E)-4,5-dimethylhexa-1,3-dienyl]-5-oxopyrrolidin-1-yl}ethyl)benzoic acid;
4-(2-{(2R)-2-[(1E,3E)-4,5-dimethylhexa-1,3-dienyl]-5-oxopyrrolidin-1-yl}ethyl)benzoic acid;
4-(2-{(2R)-2-[(1Z,3E)-4-cyclohexylbuta-1,3-dienyl]-5-oxopyrrolidin-1-yl}ethyl)benzoic acid;
4-(2-((2R)-2-[(1E,3E)-4-cyclohexylbuta-1,3-dienyl]-5-oxopyrrolidin-1-yl}ethyl)benzoic acid;
4-(2-{(2R)-2-[(1Z,3E)-4-phenyl-4-triflurobuta-1,3-dienyl]-5-oxopyrrolidin-1-yl}ethyl)benzoic acid;
4-(2-{(2R)-2-[(1E,3E)-4-phenyl-4-triflurobuta-1,3-dienyl]-5-oxopyrrolidin-1-yl}ethyl)benzoic acid;
4-(2-{(2R)-2-[(1Z,3Z)-4-phenyl-4-triflurobuta-1,3-dienyl]-5-oxopyrrolidin-1-yl}ethyl)benzoic acid;
4(2-{(2R)-2-[(1E,3Z)-4-phenyl-4-triflurobuta-1,3-dienyl]-5-oxopyrrolidin-1-yl}ethyl)benzoic acid;
4-(2-{(2R)-2-[(1Z,3E)-4-cyclopropylpenta-1,3-dienyl]-5-oxopyrrolidin-1-yl}ethyl)benzoic acid;
4-(2-{(2R)-2-[(1E,3E)-4-cyclopropylpenta-1,3-dienyl]-5-oxopyrrolidin-1-yl}ethyl)benzoic acid;
5-(3-{(2R)-2-[(1Z,3E)-4-methylocta-1,3-dienyl]-5-oxopyrrolidin-1-yl}propyl)nicotinic acid; and
5-(3-{(2R)-2-[(1E,3E)-4 methylocta-1,3-dienyl]-5-oxopyrrolidin-1-yl}propyl)nicotinic acid.

23. A method for treating a disease in a mammal selected from the group consisting of dysmenorrheal, undesired bone loss, inflammation resulting from Chronic Obstructive Pulmonary Disorder, a gastric ulcer, asthma, and an ovulatory disorder in a female undergoing ovulation induction or ART treatment, comprising:
administering to the mammal an effective amount of a compound of claim 1.

24. The method according to claim 23 wherein the mammal is suffering from dysmenorrheal.

25. The method according to claim 23 wherein the mammal is suffering from a gastric ulcer.

26. The method according to claim 23 wherein the mammal is suffering from asthma.

27. The method according to claim 23 wherein the mammal is suffering from inflammation resulting from Chronic Obstructive Pulmonary Disorder.

28. The method according to claim 23 wherein the mammal is suffering from an ovulatory disorder in a female undergoing ovulation induction or ART treatment.

29. The method according to claim 23 wherein the mammal is suffering from undesired bone loss.

30. A pharmaceutical composition comprising a pharmaceutically acceptable carrier and one or more compounds of claim 1.

31. A pharmaceutical composition of claim 30 wherein the compound is packaged together with instructions for use of the compound for the treatment of dysmenorrheal, undesired bone loss, inflammation resulting from Chronic Obstructive Pulmonary Disorder, a gastric ulcer, asthma, and an ovulatory disorder wherein the female is undergoing ovulation induction or ART treatment.

* * * * *